United States Patent
Fujihara et al.

(10) Patent No.: US 7,759,473 B2
(45) Date of Patent: Jul. 20, 2010

(54) NUCLEOTIDE OLIGOMER, NUCLEOTIDE POLYMER, METHOD FOR DETERMINING STRUCTURE OF FUNCTIONAL SUBSTANCE AND METHOD FOR MANUFACTURING FUNCTIONAL SUBSTANCE

(75) Inventors: Tsuyoshi Fujihara, Kawasaki (JP); Shozo Fujita, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 1162 days.

(21) Appl. No.: 11/352,197

(22) Filed: Feb. 13, 2006

(65) Prior Publication Data

US 2008/0300393 A1    Dec. 4, 2008

(30) Foreign Application Priority Data

Feb. 14, 2005   (JP) .............................. 2005-035865

(51) Int. Cl.
 *C07H 21/02* (2006.01)
 *C07H 21/04* (2006.01)

(52) U.S. Cl. ..................... 536/23.1; 536/22.1; 536/24.3

(58) Field of Classification Search ........................ None
See application file for complete search history.

(56) References Cited

FOREIGN PATENT DOCUMENTS

| JP | 10-508304 | 8/1998 |
|---|---|---|
| JP | 2002-291491 | 10/2002 |
| JP | 2004-337022 | 12/2004 |

OTHER PUBLICATIONS

Catherine M. McKeen et al.; "Synthesis of fluorophore and quencher monomers for use in Scorpion primers and nucleic acid structural probes"; Organic & Biomolecular Chemistry; vol. 1; No. 13; Jul. 7, 2003; pp. 2217-2404.
First Page of Japanese Office Action dated Nov. 11, 2008.
Mohammad Ahmadian et al.; "A comparative study of the thermal stability of oligodeoxyribonucleotides containing 5-substituted 2'-deoxyuridines"; Nucleic Acids Research; 1998; vol. 26; No. 13; pp. 3127-3135.
First Page of Japanese Office Action dated Jul. 29, 2008.

*Primary Examiner*—Patrick T Lewis
(74) *Attorney, Agent, or Firm*—Kratz, Quintos & Hanson, LLP

(57) ABSTRACT

A modified nucleotide n-mer (where n is an integer of 2 or more) is used which comprises a nucleoside unit with a substituent group introduced into the base, wherein the substituent group is bound to the base via a triple bond. Novel nucleotide oligomers, nucleotide polymers, and nucleosides which can be used as raw materials or intermediates in the synthesis of this nucleotide oligomer and nucleotide polymer, as well as novel techniques for structural determination and manufacture of a functional substance having high affinity for a target, are provided.

8 Claims, 9 Drawing Sheets

...(24)

...(25)

(74)

(75)

(76)

(77)

(78)

(79)

(80)

(81)

(82)

(83)

Base=

NUCLEOTIDE OLIGOMER, NUCLEOTIDE POLYMER, METHOD FOR DETERMINING STRUCTURE OF FUNCTIONAL SUBSTANCE AND METHOD FOR MANUFACTURING FUNCTIONAL SUBSTANCE

The attached Sequence Listing, in both hard copy and electronic form, submitted herewith is incorporated herein by reference in its entirety.

CROSS-REFERENCE TO RELATED APPLICATIONS

This application is based upon and claims the benefit of priority from the prior Japanese Patent Application No. 2005-35865, filed on Feb. 14, 2005, the entire contents of which are incorporated herein by reference.

BACKGROUND OF THE INVENTION

1. Field of the Invention

The present invention relates to a novel nucleotide oligomer and nucleotide polymer, to nucleosides which can be used as raw materials or intermediates in the synthesis of this nucleotide oligomer and nucleotide polymer, and to functional substances (in the present invention, a functional substance is one having affinity for a target) which exhibit high affinity and/or recognition specificity for a variety of targets and which are applicable to drugs, drug delivery, biosensors, controlling the expressed amounts of genes, curing diseases caused by genetic abnormalities, elucidating the functions of proteins translated by genes, developing reaction catalysts and the like, and which are particularly suited to analysis, screening and the like of proteins, and to a manufacturing method therefor.

2. Description of the Related Art

As biotechnology advances, the focus of interest among researchers and scientists is shifting from genes to analysis of proteins which are the product of genes. Proteins are often analyzed by analyzing substances which have affinity for the proteins.

Consequently, it could be said that a protein can only be analyzed if there is a substance having affinity for that protein. A very large number of proteins to be analyzed are present in cells, and most of their amino acid sequences, structures and the like are unknown, so a variety of substances are needed for analyzing proteins.

At present, however, no efficient method for preparing or obtaining the aforementioned substances for analyzing proteins has been established. The most common method of obtaining a substance having affinity for a specific protein is a method of selecting affinity antibodies using the immune system of an animal. However, because animals are used in this method a large volume of proteins are needed, increasing the number of steps and the costs. Moreover, the affinity antibodies selected and obtained by this method cannot be amplified (that is, replicated). Another problem is that only affinity antibodies having affinity for the same target can be selected. As a result, it is extremely difficult to select individual affinity antibodies having affinity for most types of proteins in cells, and to obtain them in sufficient quantities.

Research has been done into introducing puromycin into the 3' end of mRNA as a means of synthesizing proteins with genetic information (see for example Japanese Patent Application Laid-open No. 2002-291491 (Claims)). This exploits the fact that puromycin is easily incorporated into proteins because it is mistaken for an amino acid by the translation system. At present, however, incorporation efficiency of puromycin is poor, and only selection of a functional substance from a library of random amino acid 3 residues has been reported.

Meanwhile, methods such as the immunosensor amperometric method have been developed for identifying proteins using antibodies. With this method, as little as 2 ng/L of protein can be measured. However, in such a low-concentration protein solution most of the antibodies are not bound to proteins, and many non-specific reactions occur in solutions (such as serum) containing many impurities, detracting from measurement precision.

Although viral and other coatable supermolecular assemblies have been proposed (see for example Japanese Patent Publication No. H10-508304 (Claims)), the structures in this case are complex, and none with higher affinity than antibodies for a variety of targets can be efficiently manufactured.

SUMMARY OF THE INVENTION

In one method of manufacturing a substance having affinity for a target, a mixture is synthesized containing tiny quantities of each of numerous candidates for the substance, a substance having affinity for the target is selected from these candidate substances, the selected substance is amplified by some method, the structure is analyzed using the amplified substance, and the target substance is selectively synthesized based on the analyzed structure (see for example Japanese Patent Publication Laid-open No. 2004-337022, paragraph 0040).

Specifically, when the target is a certain protein and the aforementioned functional substance is a nucleotide sequence, a mixture is synthesized comprising a number of candidate nucleotide substances, a nucleotide sequence having affinity for the protein which is the target is selected from the mixture and amplified, the base sequence of the amplified nucleotide sequence is determined, and the nucleotide sequence having affinity for the target protein is manufactured based on the determined sequence (that is, the determined structure).

It is thus possible to determine a target functional substance from small amounts of functional substance candidates and use it in manufacture, thus allowing the rapid development of novel functional substances in adequate quantities.

If a functional substance can be obtained in adequate quantities, analysis and screening methods and the like can be developed for the structure of the target (such as the sequence structure of a protein) through its structure determination, and these results can be applied to drugs, drug delivery, biosensors, control of expressed amounts of genes, cures for diseases caused by genetic abnormalities, elucidating the functions of proteins encoded by genes and development of reaction catalysts.

Consequently, there is a great need for novel raw materials and intermediates for synthesizing candidate nucleotide sequences.

One problem is that PCR (polymerase chain reaction) is often used in this amplification, and because modifying groups are not included in the nucleotide sequences after the amplification it must be identified solely by the four bases adenine, guanine, cytosine and thymine, so there is great need for nucleotide sequences which can be identified based on differences other than these four after amplification.

One way to meet these needs is through the use of modified nucleotide n-mers, for example. Thus for example if only combinations of dimers (n=2) are used nucleotide sequences can be distinguished from each other based on the combinations of dimers in the nucleotide sequences.

Consequently, there is a great need for novel raw materials and intermediates for synthesizing nucleotide sequences which are adapted to such techniques.

Another problem is that such amplification may not be possible depending on the selected functional substance, so that adequate quantities of functional substance cannot be obtained. For example, amplification may be impeded by the selected functional substance. This occurs when the selected functional substance has a strong positive charge for example. If amplification is impeded the structure cannot be determined and the functional substance cannot then be manufactured.

One reason for this is that the PCR or other amplification reaction is impeded by substituent groups introduced with the aim of improving affinity of the functional substance for the protein or the like, for example.

In light of these problems, it is an object of the present invention to develop a novel nucleotide oligomer, a novel nucleotide polymer, novel nucleosides as raw materials or intermediates for synthesizing this nucleotide oligomer and nucleotide polymer, and novel techniques which permit the structural determination and manufacture of a functional substance having high affinity for a target. Other objects and advantages will be clarified in the following descriptions.

In one aspect of the present invention, a modified nucleotide n-mer (where n=1) is provided with a structures represented by Formula 18 below, comprising a nucleoside unit with a substituent group introduced into the base, wherein the substituent group is bound to the base via a triple bond:

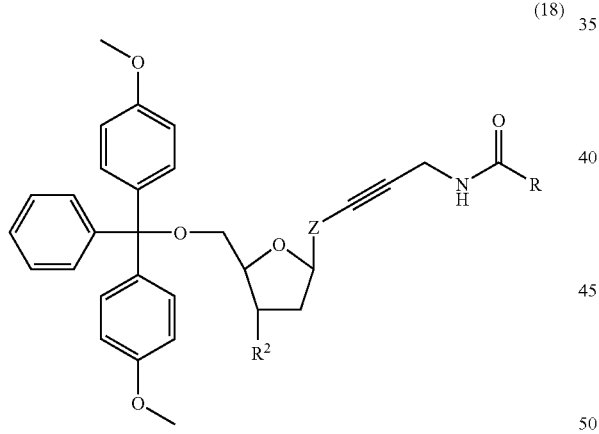

(18)

(where Z represents a group comprising a 7-deazaadenine skeleton, 7-deazaguanine skeleton, cytosine skeleton or uracil skeleton independently of the other formulae, R represents hydrogen or a functional group having 0 to 100 carbon atoms independently of the other formulae, and $R^2$ represents a hydroxy group, O-β-cyanoethoxy-diisopropylaminophosphine group, O-methoxy-diisopropylaminophosphine group or H-phosphonate group independently of the other formulae). A novel nucleotide monomer is obtained by this aspect of the present invention.

In another aspect of the present invention, a modified nucleotide m-mer (where m represents an integer of 2 or more) comprising the aforementioned nucleotide n-mer as a constituent element is provided. A novel nucleotide oligomer is obtained by this aspect of the present invention.

In another aspect of the present invention, a modified nucleotide n-mer (where n represents an integer of 2 or more) is provided comprising a nucleoside unit having a substituent group introduced into the base, wherein the substituent group is bound to the base via a triple bond. A novel nucleotide oligomer is obtained by this aspect of the present invention.

Preferable are that the aforementioned base be a purine or pyrimidine base, that the base have a 7-deazaadenine skeleton, 7-deazaguanine skeleton, cytosine skeleton or uracil skeleton, that the aforementioned substituent group have at least one group selected from a group consisting of the natural or artificial amino acid groups, metal complex groups, fluorescent pigment groups, oxidation-reduction pigment groups, spin labelable groups, alkyl groups with 1 to 100 carbon atoms and the groups represented by Formulae 1 through 10, any of which may have a substituent group:

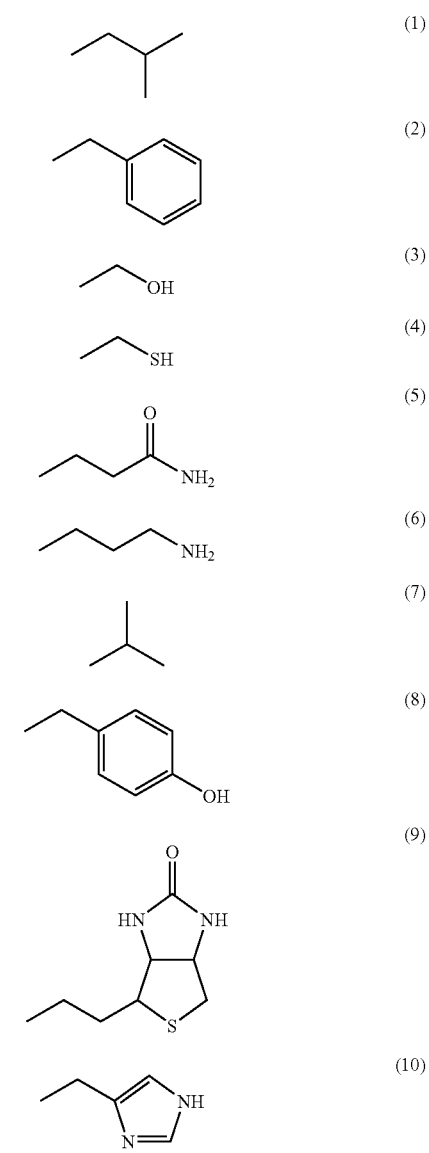

that the aforementioned substituent group be the group represented by Formula 11:

(11) 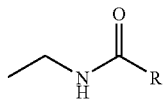

(where R represents hydrogen or a functional group having 0 to 100 carbon atoms independently of the other formulae), and that the aforementioned substituent group be a group selected from a group consisting of the groups represented by Formulae 12-17:

(12) 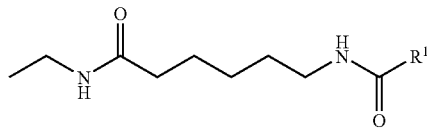

(13) 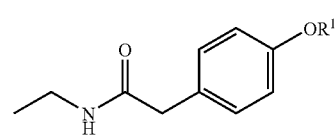

(14) 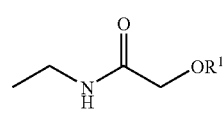

(15) 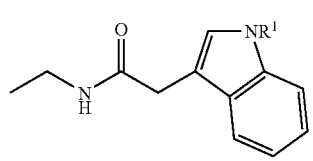

(16) 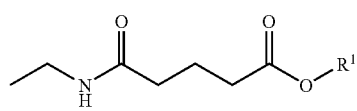

(17) 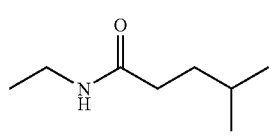

(where in Formulae 12-16, each $R^1$ independently represents a trifluoromethyl group, t-butyldimethylsilyl group, methyl group, t-butyldiphenylsilyl group, 2-benzenesulfonic acid ethoxy group or 9-fluorenylmethyl group), and that n be an integer from 2 to 4.

In another aspect of the present invention nucleosides are provided having a structure represented by one of Formulae 19-23 below. Novel nucleosides are obtained by this aspect of the present invention.

(19) 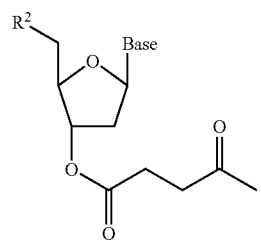

(In Formula 19, $R^2$ represents a hydroxy group, O-β-cyano-ethoxy-diisopropylaminophosphine group, O-methoxy-di-isopropylaminophosphine group or H-phosphonate group independently of the other formulae).

(20) 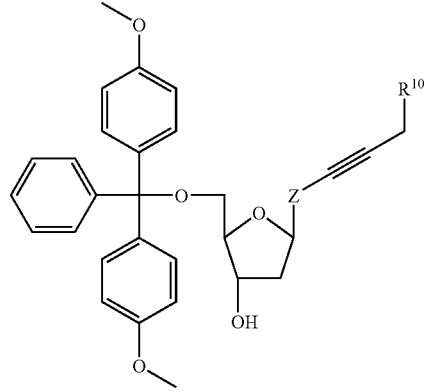

(In Formula 20, Z represents a 7-deazaadenine skeleton, 7-deazaguanine skeleton, cytosine skeleton or uracil skeleton independently of the other formulae, and $R^{10}$ represents $NH_2$ or NH—(CO)—R, where this R represents hydrogen or a functional group with 0 to 100 carbon atoms independently of the other formulae).

(21) 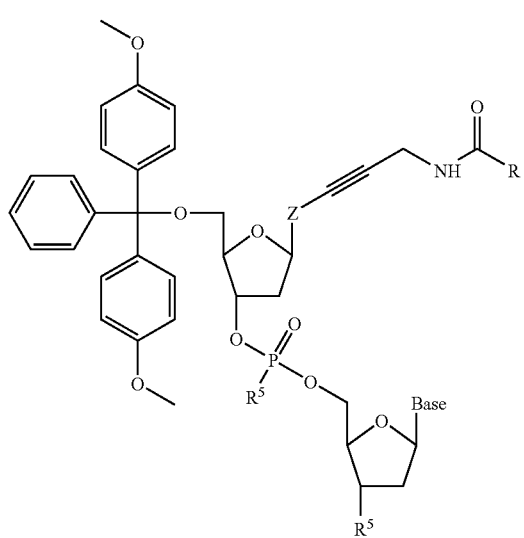

(In Formula 21, $R^5$ represents a hydroxy group or O—(CO)CH$_2$CH$_2$(CO)CH$_3$ independently of the other formulae, $R^6$ represents a hydroxy group or 2-cyanoethoxy group independently of the other formulae, Z represents a group comprising a 7-deazaadenine skeleton, 7-deazaguanine skeleton, cytosine skeleton or uracil skeleton independently of the other formulae, and R represents hydrogen or a functional group with 0 to 100 carbon atoms independently of the other formulae).

(22)

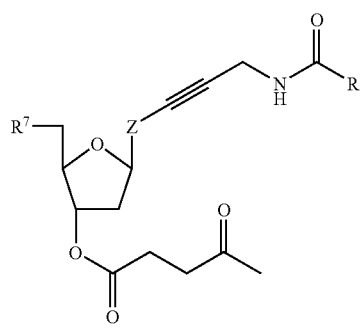

(In Formula 22, $R^7$ represents a hydroxy group or dimethyltrityl group, Z represents a group comprising a 7-deazaadenine skeleton, 7-deazaguanine skeleton, cytosine skeleton or uracil skeleton independently of the other formulae, and R represents hydrogen or a functional group with 0 to 100 carbon atoms independently of the other formulae).

(23)

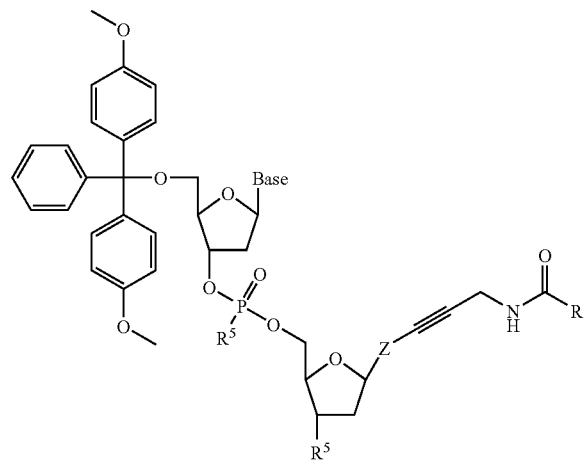

(In Formula 23, $R^5$ represents a hydroxy group or O—(CO)CH$_2$CH$_2$(CO)CH$_3$ independently of the other formulae, $R^6$ represents a hydroxy group or 2-cyanoethoxy group independently of the other formulae, Z represents a group comprising a 7-deazaadenine skeleton, 7-deazaguanine skeleton, cytosine skeleton or uracil skeleton independently of the other formulae, and R represents hydrogen or a functional group with 0 to 100 carbon atoms independently of the other formulae).

Another aspect of the present invention provides a manufacturing method for a modified nucleotide n-mer (wherein n is an integer of 1 or more) in which the aforementioned nucleosides are used as raw materials or intermediates. The modified nucleotide n-mer thus manufactured is preferably the aforementioned modified nucleotide n-mer. A novel nucleotide monomer or oligomer is obtained by this aspect of the present invention.

Other aspects of the present invention provide a modified nucleotide sequence comprising the structure of the aforementioned modified nucleotide n-mer, and a modified nucleotide sequence comprising the structure of a modified nucleotide n-mer manufactured by the aforementioned manufacturing method for a modified nucleotide n-mer. A novel modified nucleotide sequence is obtained by these aspects of the present invention.

Other aspects of the present invention provide a substance (functional substance) comprising the aforementioned modified nucleotide sequence and having affinity for a target, and constituent elements thereof. A novel functional substance is obtained by these aspects of the present invention.

Another aspect of the present invention provides a structural determination method for a functional substance, in which candidates for a substance (functional substance) having affinity for a target are synthesized, a functional substance having affinity for the target is selected from those functional substance candidates, a specific substituent group is removed or not removed from the selected functional substance, the selected functional substance or the functional substance with the specific substituent group removed is amplified, and the structure of the amplified functional substance is determined, wherein the functional substance candidates are synthesized using the aforementioned modified nucleotide n-mer. A novel functional substance structural determination method is obtained by this aspect of the present invention.

Other aspect of the present invention provide a method for manufacturing a functional substance, in which candidates for a substance (functional substance) having affinity for a target are synthesized, a functional substance having affinity for the target is selected from those functional substance candidates, a specific substituent group is removed or not removed from the selected functional substance, the selected functional substance or the functional substance with the specific substituent group removed is amplified, the structure of the amplified functional substance is determined, and the functional substance is manufactured based on that structure, wherein the functional substance candidates are synthesized using the aforementioned modified nucleotide n-mer, as well as a method for manufacturing constituent elements of that functional substance. A novel method for manufacturing a functional substance is obtained by these aspects of the present invention.

In all of these cases, the aforementioned target is preferably at least one substance selected from a group consisting of proteins, lipoproteins, glycoproteins, polypeptides, lipids, polysaccharides, lipopolysaccharides, nucleic acids, environmental hormones, drugs, composite materials thereof, and materials obtained by decomposing these materials.

A novel nucleotide oligomer and nucleotide polymer, nucleosides which can be used as raw materials or intermediates in the synthesis of this nucleotide oligomer and nucleotide polymer, and novel techniques for structural determination and manufacture of a functional substance having strong affinity for a target are provided by the present invention.

DESCRIPTION OF THE PREFERRED EMBODIMENTS

Embodiments of the present invention are explained below using drawings, examples and the like. These drawings, examples and the like and explanations are meant to exemplify the present invention and not to limit its scope. Of course, other embodiments can be encompassed in the scope of the present invention as long as they are consistent with the gist of the present invention. In formulae of the present invention, a terminal solid line signifies a methyl group, while a broken line signifies the connection of a methylene group. R represents hydrogen or a functional group with 0 to 100 carbon atoms independently in each formula, while $R^1$ represents a trifluoromethyl group, t-butyldimethylsilyl group, methyl group, t-butyldiphenylsilyl group, 2-benzenesulfonic acid ethoxy group, 9-fluorenylmethyl group or other functional group which can be deprotected under conditions which do not break down oligo DNA independently in each formula, $R^2$ represents a hydroxy group, O-β-cyanoethoxy-diisopropylaminophosphine group, O-methoxy-diisopropylaminophosphine group or H-phosphonate group independently in each formula, $R^3$ represents hydrogen or an acetyl group, isobutyryl group, benzoyl group, phenoxyacetyl group or p-(i-propyl)phenoxyacetyl group independently in each formula, $R^4$ represents hydrogen or an acetyl group, isobutyryl group, benzoyl group, phenoxyacetyl group or p-(i-propyl)phenoxyacetyl group independently in each formula, and $R^5$ represents a hydroxy group or O—(CO)CH$_2$CH$_2$(CO)CH$_3$ independently in each formula. $R^6$ represents a hydroxy or 2-cyanoethoxy group independently in each formula. $R^7$ represents a hydroxy or dimethyltrityl group. $R^8$ represents the terminal group of the biotinylated SH terminal molecule of FIG. 7. $R^9$ represents the terminal group of X or Y in FIG. 6. $R^{10}$ represents NH$_2$ or NH—(CO)—R.

Figure 9:
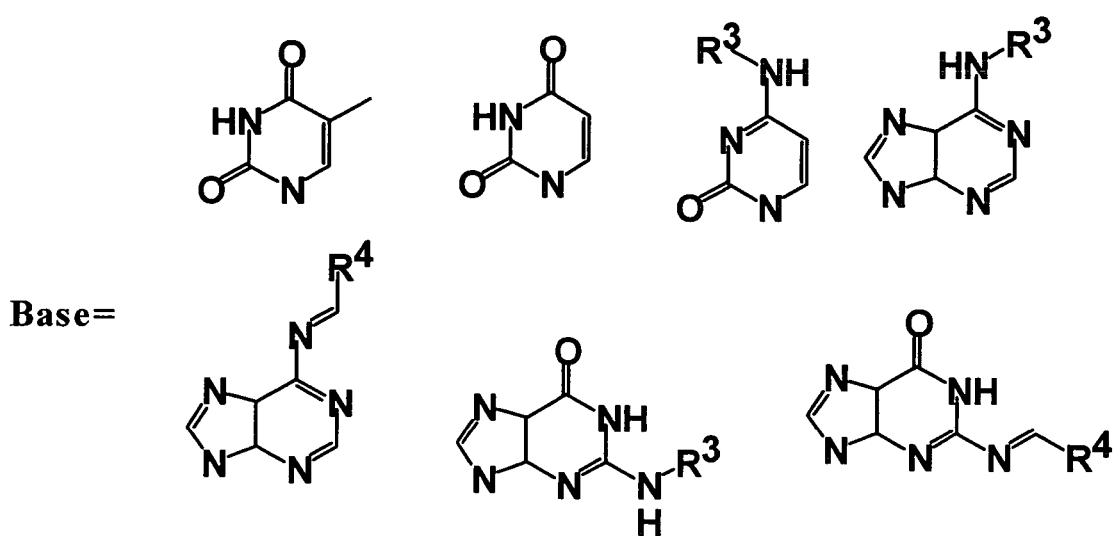
FIG. 9 shows Bases.

Unless otherwise limited, a "base" in the present is a base which may be the adenine, guanine, cytosine, thymine or uracil shown in FIG. 9, such a base with protection, or a base similar to the base of the modified nucleotide n-mer of the present invention.

First, some of the terms used in the present invention are defined.

(Nucleoside Unit)

The nucleoside units in the present invention each comprise a sugar and a base. They may also include phosphoric acid groups and phosphite groups.

(Nucleoside)

This signifies a structure comprising a sugar and a base. It may include a phosphoric acid group or phosphite group. It may include only one pair of a sugar and a base or two or more such pairs. It may be a nucleotide if it comprises a phosphoric acid group.

(Substituent Group Bound to a Base Via a Triple Bond)

There are no particular limits on this substituent group, which may be selected appropriately according to the object. Examples include natural or artificial amino acid groups, metal complex groups, fluorescent pigment groups, oxidation-reduction pigment groups, spin labelable groups, alkyl groups with 1 to 100 carbon atoms, and the groups represented by Formulae 1 through 10. These may also be further modified by substituent groups. One of or more than one of these may be used.

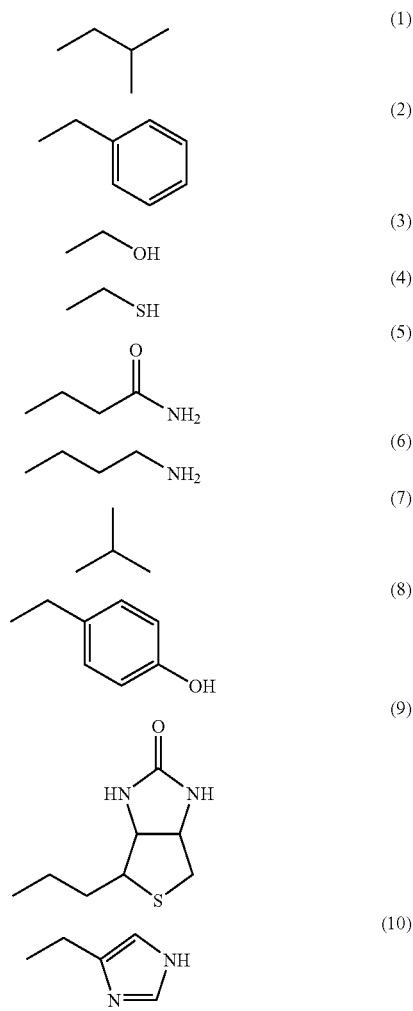

There are no particular limits on the aforementioned natural or artificial amino acid group, which can be selected according to the object, and examples include valine, leucine, isoleucine, alanine, arginine, glutamine, lysine, aspartic acid, glutamic acid, proline, cysteine, threonine, methionine, histidine, phenylalanine, tyrosine, tryptophan, asparagine, glycine, serine and groups derived from these.

There are no particular limits on the aforementioned metal complex group as long as it is a group derived from a compound having ligands arranged on metal ions, and it can be selected appropriately depending on the object, with examples including groups derived from ruthenium bipyridyl complexes, ferrocene complexes and nickel imidazole complexes.

There are no particular limits on the aforementioned fluorescent pigment group, which may be selected appropriately according to the object, and examples include groups derived from fluorescein series, rhodamine series, eosin series, NBD series and other fluorescent pigments.

There are no particular limits on the aforementioned oxidation-reduction pigment group, which may be selected appropriately according to the object, and examples include groups derived from leucoaniline, leuco-anthocyanin and other leuco pigments and the like.

There are no particular limits on the aforementioned spin labelable group, which may be selected appropriately according to the object, and examples include groups derived from iron N-(dithiocarboxy)sarcosine, TEMPO (tetramethylpiperidine) derivatives and the like.

There are no particular limits on the aforementioned alkyl group with 1 to 100 carbon atoms, which may be selected appropriately according to the object, and examples include methyl, ethyl, propyl, isopropyl, butyl, isobutyl, tert-butyl, pentyl, neopentyl, hexyl, cyclohexyl, octyl, nonyl and decyl groups and the like.

The group represented by Formula II is also desirable.

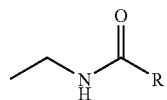

(11)

In Formula II, R represents hydrogen or a functional group with 0 to 100 carbon atoms independently of the other formulae.

It is still more desirable that the group represented by Formula II be a group selected from a group consisting of the groups represented by Formulae 12 through 17.

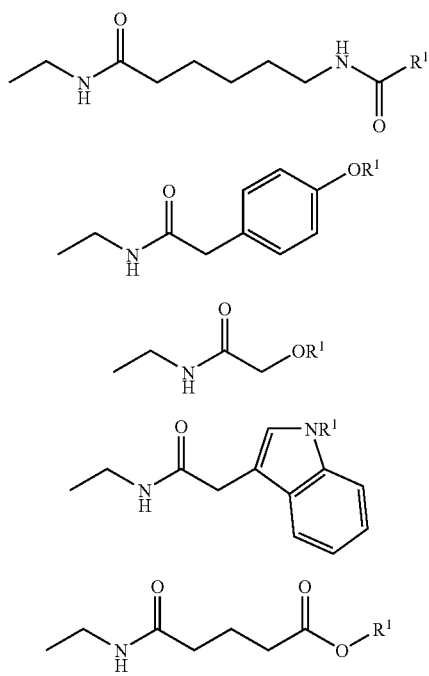

-continued

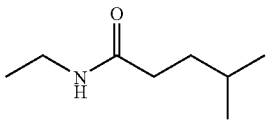

(17)

In Formulae 12 through 16, each $R^1$ independently represents a trifluoromethyl group, t-butyldimethylsilyl group, methyl group, t-butyldiphenylsilyl group, 2-benzenesulfonic acid ethoxy group, 9-fluorenylmethyl group or other functional group which can be deprotected under conditions which do not break down oligo DNA.

(Modified Nucleotide n-mer).

A nucleotide n-mer is a nucleotide oligomer which comprises 1 or more nucleoside units. That is, n is an integer of 1 or more. The number of phosphoric acid groups per molecule may be smaller than the number of nucleoside units. When counting the number of nucleoside units (that is, n) in a nucleotide n-mer of the present invention, the number is determined by the number of pairs of sugar and base, without considering the number of phosphoric acid groups or whether or not other substituent or protective groups or the like are present or differ from one another. "Modified" signifies that the base has a substituent group. However, other substituent groups may also be present in the nucleoside units or in other positions.

(Modified Nucleotide Sequence)

A modified nucleotide sequence is a nucleotide oligomer or polymer having modifying groups. A modified nucleotide sequence comprising the structure of the modified nucleotide n-mer of the present invention generally has a much larger molecular weight than the aforementioned nucleotide n-mer even if it is an oligomer. The modifying groups include modifying groups derived from the modified nucleotide n-mer of the present invention but may also include other modifying groups in some cases. "Comprising the structure of the modified nucleotide n-mer of the present invention" signifies that the modified nucleotide sequence may have structural parts other than the structure of the modified nucleotide n-mer of the present invention. Consequently, "a modified nucleotide sequence compose of the modified nucleotide n-mer of the present invention polymerized with a nucleotide oligomer other than the modified nucleotide n-mer of the present invention" could also be encompassed by the scope of the present invention. Of course, the scope of the aforementioned modified nucleotide sequence also includes those obtained by polymerizing only the modified nucleotide n-mer of the present invention.

A novel modified nucleotide n-mer ("n-mer" is used in various contexts below but in all cases n is an integer of 2 or more unless otherwise specified) is provided by the present invention. A feature of this modified nucleotide n-mer is that it comprises nucleoside units with substituent groups introduced into the base, with these substituent groups being bound to the base via triple bonds.

By adopting triple bonds it is possible to prevent the occurrence of structural changes during processing when the modified nucleotide n-mer is used as a functional substance or the like. That is, this prevents the problem of structural changes such as typically occur in the conventional procedures when a trans double bond previously introduced into a base changes into a cis double bond.

In the nucleoside units of the modified nucleotide n-mer of the present invention not all bases need have substituent groups bound via triple bonds, and there may be bases having other substituent groups or bases with no substituent groups.

The modified nucleotide n-mer of the present invention may be selected from any as long as it includes a nucleoside unit in which a substituent group is bound to a base via a triple bond, but from the standpoint of ease of synthesis and chemical stability it is desirable that the base be a purine base or a pyrimidine base. "Purine base" here is a general term for purine and derivatives having substitutions in various parts of the purine core, while "pyrimidine base" is a general term for pyrimidine and derivatives having substitutions in various parts of the pyrimidine core. More specifically, those having a 7-deazaadenine skeleton, 7-deazaguanine skeleton, cytosine skeleton or uracil skeleton are desirable.

There are no particular limits on the position where the triple bond is formed as long as it is consistent with the gist of the present invention, but considering ease of synthesis, the binding is preferably formed onto the 7 position of a purine base or the 5 position of a pyrimidine base. More specifically, the triple bond is preferably located at the 7 position in the case of 7-deazaadenine and 7-deazaguanine skeletons and at the 5 position in the case of cytosine and uracil skeletons.

Figure 1:
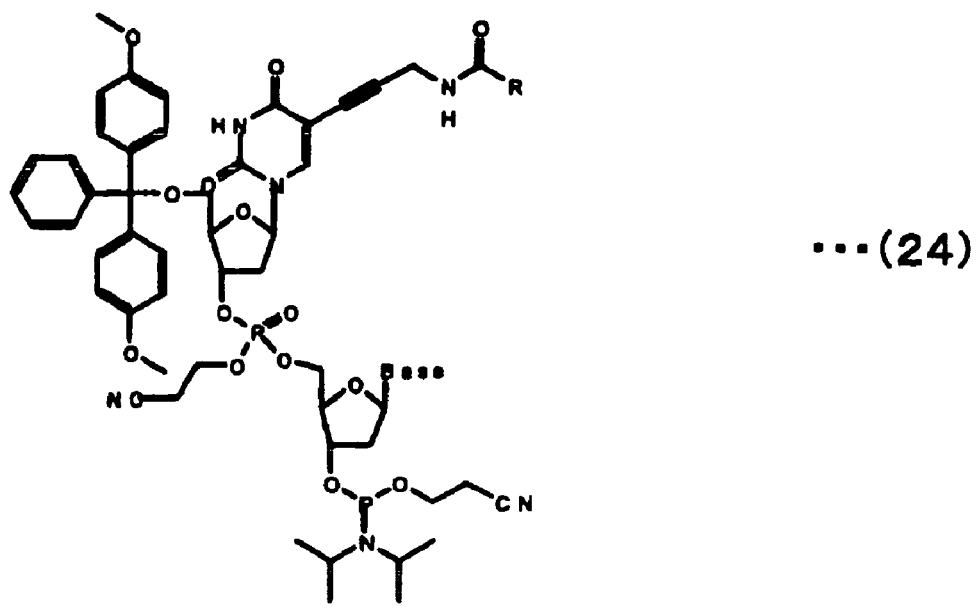
FIG. 1 shows examples of modified nucleotides including a triple bond.
Figure 1:
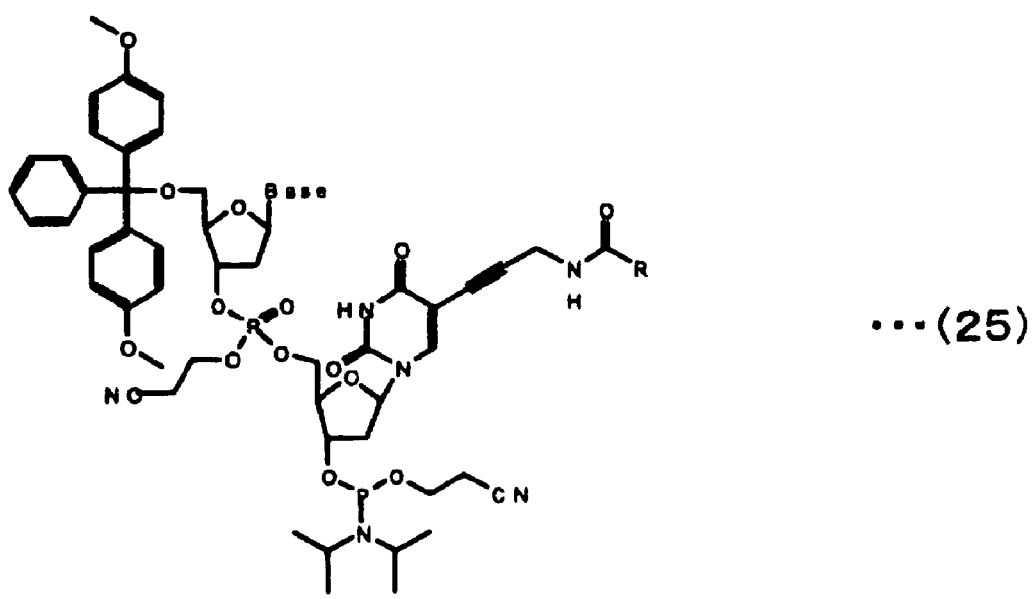
Figure 2:
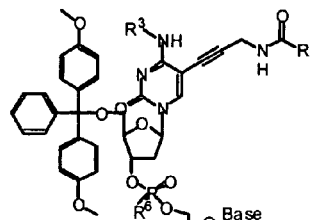
FIG. 2 shows examples of modified nucleotide dimers.
Figure 2:
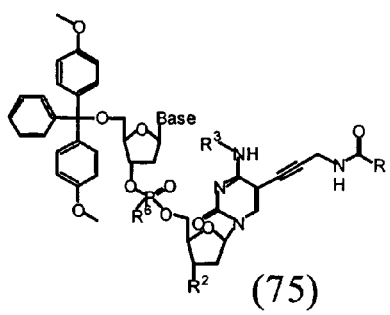
Figure 2:
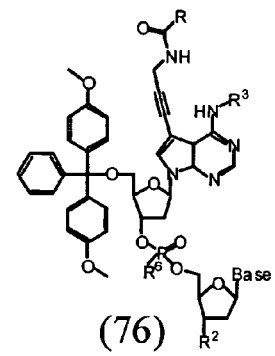
Figure 2:
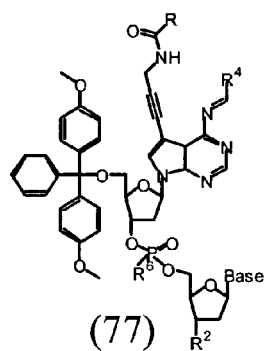
Figure 2:
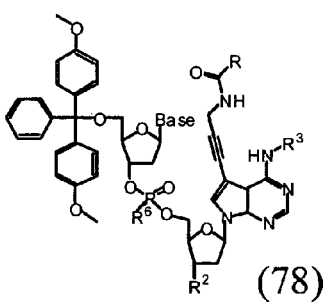
Figure 2:
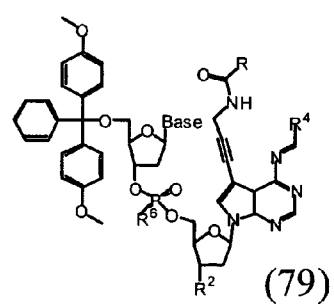
Figure 2:
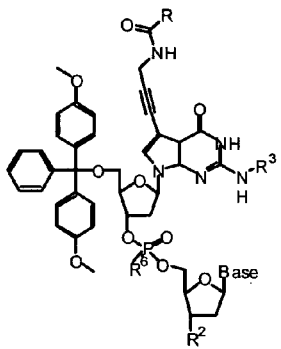
Figure 2:
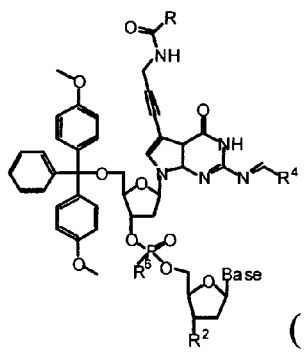
Figure 2:
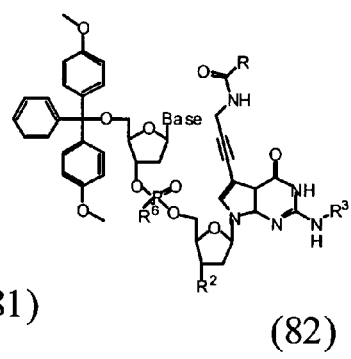
Figure 2:
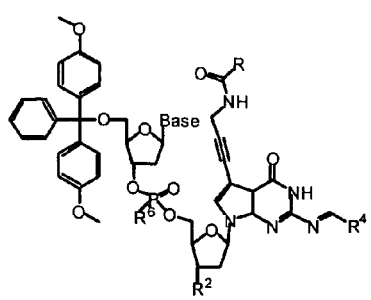

These examples are shown in Formulae 24 and 25 of FIG. 1. Formulae 24 and 25 are both examples of modified nucleotide dimers having uracil skeletons. Examples of modified nucleotide dimers with 7-deazaadenine, 7-deazaguanine and cytosine skeletons are shown in Formulae 74 through 83 of FIG. 2. R, $R^2$, $R^3$, $R^4$, $R^6$ and other symbols in FIG. 2 are defined as in other cases. In FIG. 1, $R^2$ represents an O-β-cyanoethoxy-diisopropylaminophosphine group and $R^6$ a 2-cyanoethoxy group.

From the standpoint of preventing structural changes, introduction of a triple bond of the present invention is useful not only in the case of dimers and other higher n-mers but also in the case of monomers, that is, in the case of modified nucleotide n-mers (where n=1) comprising a nucleoside unit having a substituent group introduced into a base where the substituent group is bound to the base via a triple bond. Such a case would have a structure such as that represented by Formula 18 for example:

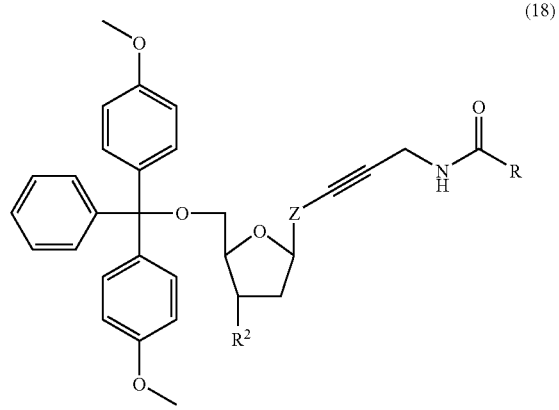

(18)

Figure 8:
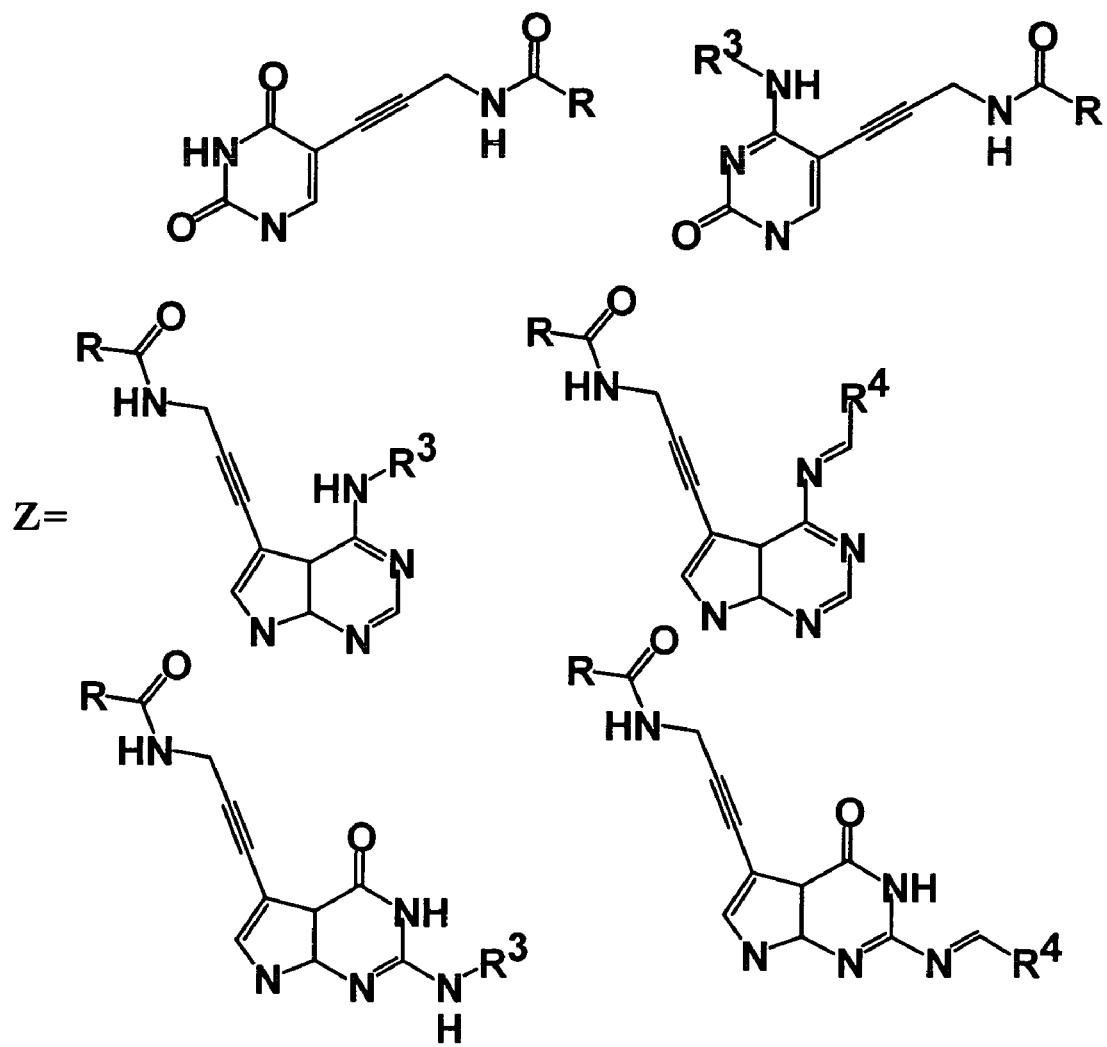
FIG. 8 shows examples of combinations of Z and R.

(where in Formula 18, Z represents a group comprising a 7-deazaadenine skeleton, 7-deazaguanine skeleton, cytosine skeleton or uracil skeleton independently of the other formulae, R represents hydrogen or a functional group having 0 to 100 carbon atoms independently of the other formulae, and $R^2$ represents a hydroxy group, O-β-cyanoethoxy-diisopropylaminophosphine group, O-methoxy-diisopropylaminophosphine group or H-phosphonate group independently of the other formulae.) Examples of combinations of Z and R are shown in FIG. 8. R, $R^3$, $R^4$ and other symbols in FIG. 8 are defined as in other cases. These combinations of Z and R can also be applied to other formulae (Formulae 20 through 23) of the present invention.

Moreover, it is possible and sometimes desirable to synthesize a modified nucleotide m-mer (where m is an integer of 2 or more) with this modified nucleotide n-mer as a constituent element. m is preferably 2 to 4.

The modified nucleotide n-mer (n=1 or more) of the present invention, including those described below, can be used favorably to synthesize a modified nucleotide sequence (that is, a modified nucleotide sequence comprising the structure of the modified nucleotide n-mer), and can be used favorably in the development of new drugs and the like as a substance comprising the modified nucleotide sequence and having affinity for a target (functional substance), or constituent elements thereof. Of course, it can also be used for other purposes. n is preferably an integer from 2 to 4 because this allows relatively easy purification.

In the present invention, the term "functional substance" is used at various stages including the stage of synthesizing functional substance candidates, the stage of selecting a functional substance, the stage of removing a specific substituent group from the functional substance, the stage of amplifying the functional substance, the stage of determining the structure of the functional substance, the stage of manufacturing the functional substance and the like, and the idea is that a functional substance comprising a modified nucleotide sequence synthesized using the aforementioned modified nucleotide n-mer (n=1 or more) can be applied to any of these stages.

There are no particular limits on the means of synthesis of the aforementioned modified nucleotide n-mer (n=1 or more) or on the means of introduction of triple bonds and substituent groups, which can be selected appropriately according to the object. For example, a dimer, trimer or other oligomer can be synthesized by the diester method, triester method, phosphite method, phosphoramidite method, H-phosphonate method, thiophosphite method or the like. Of these, the phosphoramidite method is preferred.

Figure 3:
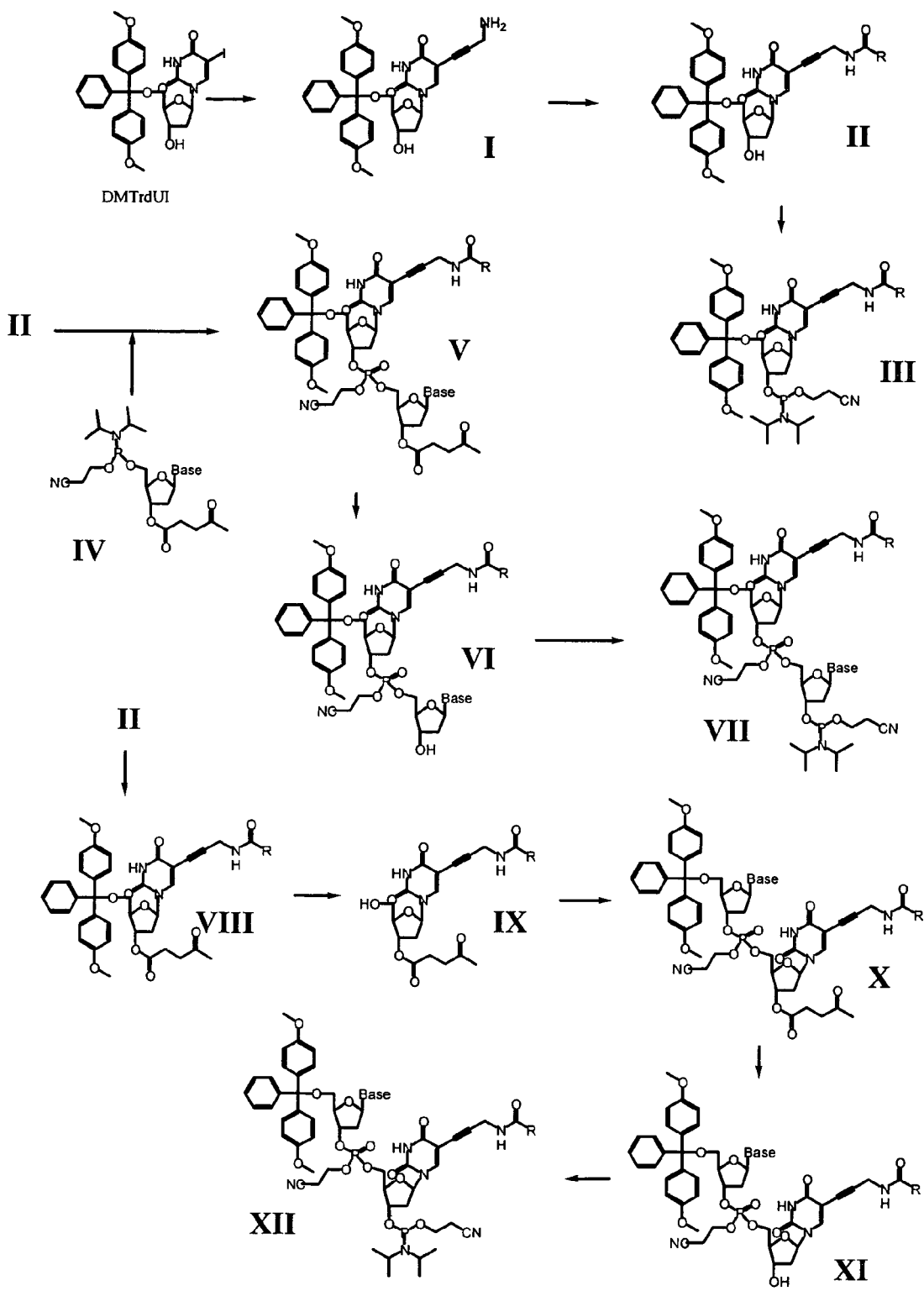
FIG. 3 shows synthesis routes for modified nucleotide n-mers.

Taking a system using a uracil skeleton as an example, selection of raw materials or intermediates such as those shown in the synthesis routes of FIG. 3 is preferable for their ease of synthesizing, for the purposes of synthesis of a modified nucleotide n-mer (n=1 or more) as well as introduction of a triple bond and a substituent group. The same is thought to apply when using other skeleton systems.

Manufacturing methods using these raw materials or intermediates are particularly suitable for synthesizing the various modified nucleotide n-mers described above. In more ordinary terms, it is desirable to use the nucleosides represented by the following Formulae 19 through 23 as raw materials or intermediates.

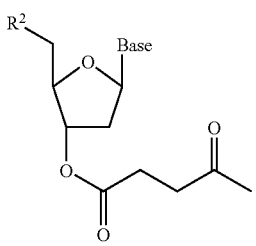
(19)

(In Formula 19, $R^2$ represents a hydroxy group, O-β-cyano-ethoxy-diisopropylaminophosphine group, O-methoxy-diisopropylaminophosphine group or H-phosphonate group independently of the other formulae).

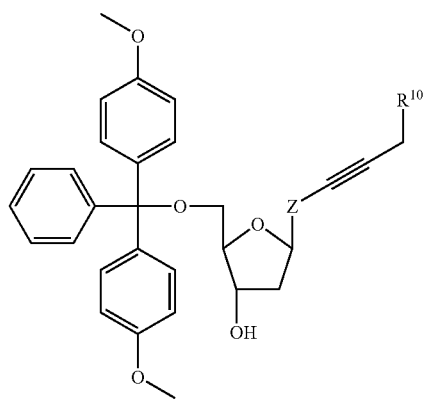
(20)

(In Formula 20, Z represents a 7-deazaadenine skeleton, 7-deazaguanine skeleton, cytosine skeleton or uracil skeleton independently of the other formulae, and $R^{10}$ represents $NH_2$ or NH—(CO)—R, where this R represents hydrogen or a functional group with 0 to 100 carbon atoms independently of the other formulae).

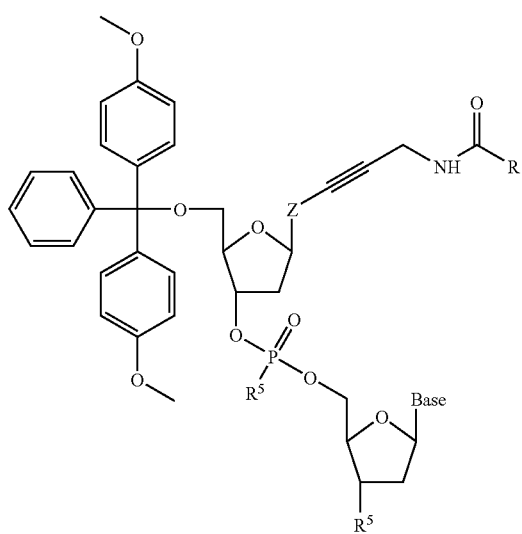
(21)

(In Formula 21, $R^5$ represents a hydroxy group or O—(CO)$CH_2CH_2(CO)CH_3$ independently of the other formulae, $R^6$ represents a hydroxy group or 2-cyanoethoxy group independently of the other formulae, Z represents a group comprising a 7-deazaadenine skeleton, 7-deazaguanine skeleton, cytosine skeleton or uracil skeleton independently of the other formulae, and R represents hydrogen or a functional group with 0 to 100 carbon atoms independently of the other formulae).

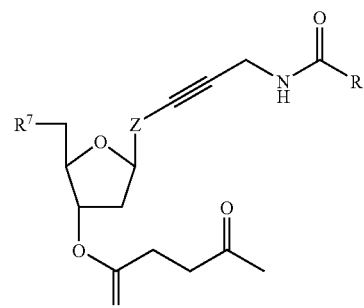
(22)

(In Formula 22, $R^7$ represents a hydroxy group or dimethyltrityl group, Z represents a group comprising a 7-deazaadenine skeleton, 7-deazaguanine skeleton, cytosine skeleton or uracil skeleton independently of the other formulae, and R represents hydrogen or a functional group with 0 to 100 carbon atoms independently of the other formulae).

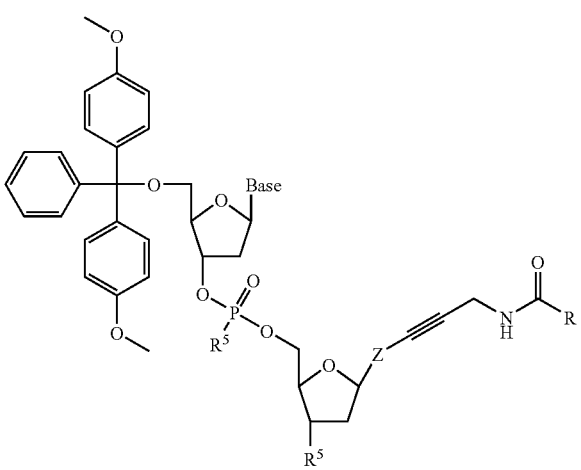
(23)

(In Formula 23, $R^5$ represents a hydroxy group or 0-(CO)$CH_2CH_2(CO)CH_3$ independently of the other formulae, $R^6$ represents a hydroxy group or 2-cyanoethoxy group independently of the other formulae, Z represents a group comprising a 7-deazaadenine skeleton, 7-deazaguanine skeleton, cytosine skeleton or uracil skeleton independently of the other formulae, and R represents hydrogen or a functional group with 0 to 100 carbon atoms independently of the other formulae).

There are no particular limits on the method of polymerizing the aforementioned oligomer, which can be selected appropriate according to the object from known methods, and desirable methods include a method using a DNA synthesizer (automatic DNA synthesizer) and a method in which monomer blocks are arranged onto random oligonucleotide sequences that have been produced beforehand, and they are subjected to annealing for the bonding to occur by the action of a DNA ligase or RNA ligase.

Figure 4:
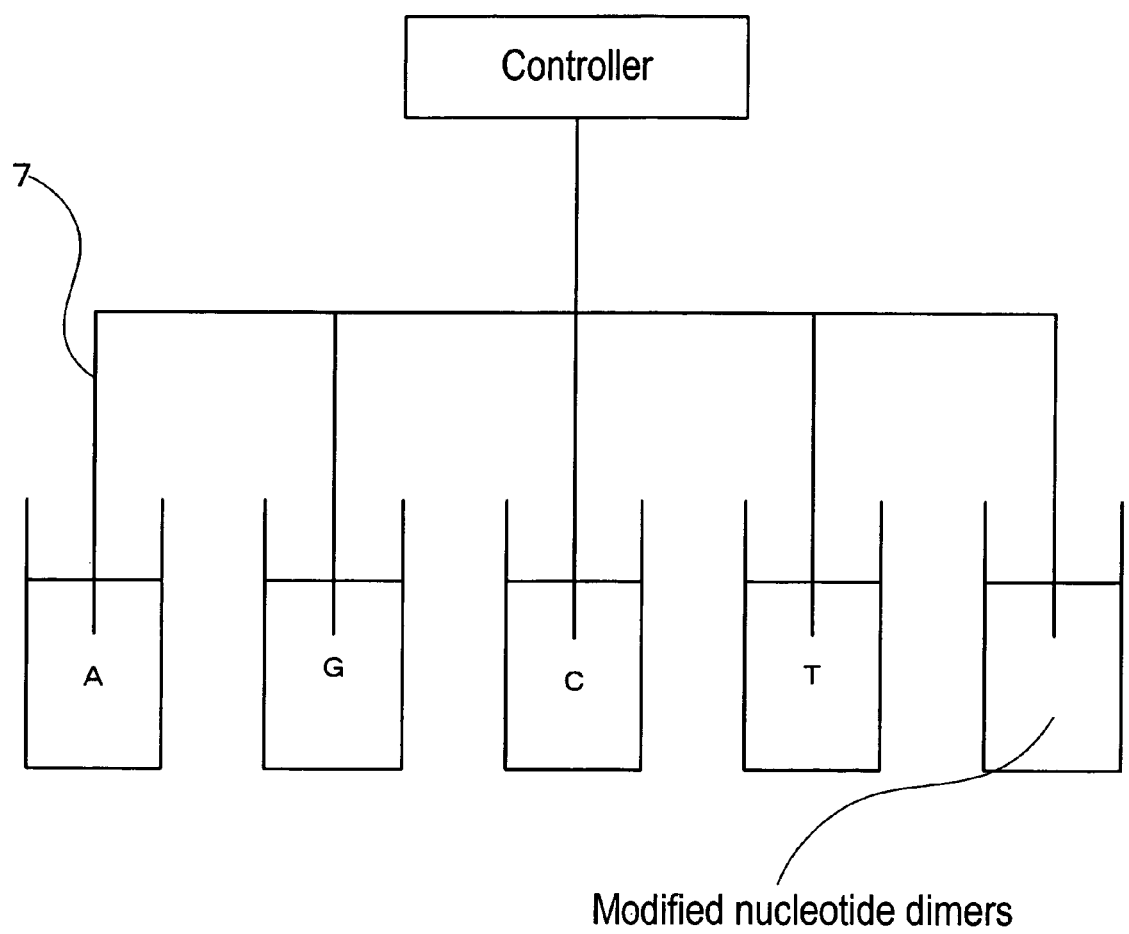
FIG. 4 shows a model view of a DNA synthesizer.

There are no particular limits on the aforementioned method using a DNA synthesizer, which can be selected appropriately according to the object. For example, a method in which a DNA synthesizer such as shown in FIG. 4 is used, reagents obtained by mixing plural types of modified nucleotide dimers that have been synthesized are used, and functional substance candidates that comprise modified nucleotide sequences with all possible and random sequencings, are produced by polymerizing the reagents taken up by suction nozzles 7 on commands from a controller, or the like is preferable. This method is advantageous, since it is possible to produce functional substance candidates efficiently.

In the structural determination method for functional substances of the present invention, modified nucleotide sequences prepared using the aforementioned nucleotide n-mer (n=1 or more) are used as functional substances or candidates therefor. In this structural determination method, functional substance candidates are synthesized, a functional substance having affinity for a target is selected from those functional substance candidates, a specific substituent group is removed or not removed from the selected functional substance, the selected functional substance or functional substance with the specific substituent group removed is amplified and the structure of the amplified functional substance is determined.

Moreover, in the functional substance manufacturing method of the present invention a functional substance is manufactured based on the structure of a functional substance obtained in this way. It is also possible and useful to manufacture constituent elements of a functional substance.

(Target)

There are no particular limits on the target in the present invention, which can be selected appropriately depending on the object, but examples include proteins, lipoproteins, glycoproteins, polypeptides, lipids, polysaccharides, lipopolysaccharides, nucleic acids, environmental hormones, drugs, composite materials thereof, etc. Materials obtained by decomposing these materials are also included.

One of these can be used independently or two or more may be used in combination. Of these, favorable examples include blood plasma proteins, tumor markers, apoproteins, viruses, autoantibodies, coagulation and fibrinolytic factors, hormones, drugs in blood, HLA antigens, environmental hormones, nucleic acids and the like.

Examples of the aforementioned blood plasma proteins include immunoglobulin (IgG, IgA, IgM, IgD, IgE), complement components (C3, C4, C5, C1q), CRP, $\alpha_1$-antitrypsin, $\alpha_1$-microglobulin, $\beta_2$-microglobulin, haptoglobin, transferrin, ceruloplasmin, ferritin and the like.

Examples of the aforementioned tumor markers include α-fetoproteins (AFP), carcinoembryonic antigens (CEA), CA19-9, CA125, CA15-3, SCC antigen, prostatic acid phosphatases (PAP), PIVKA-II, γ-seminoproteins, TPA, elastase I, neuron specific enolases (NSE), immunosuppressive acidic proteins (IAP) and the like.

Examples of the aforementioned apoproteins include apo A-I, apo A-II, apo B, apo C-II, apo C-III, apo E and the like.

Examples of the aforementioned viruses included hepatitis B virus (HBV), hepatitis C virus (HBC), HTLV-I, HIV and the like. Examples of infectious agents other than viruses include ASO, *toxoplasma, mycoplasma*, STD and the like. These pathogens and the proteins they produce may also be targets.

Examples of the aforementioned autoantibodies include anti-microsome antibodies, anti-thyroglobulin antibodies, antinuclear antibodies, rheumatic factors, anti-mitochondrial antibodies, myelin antibodies and the like.

Examples of the aforementioned coagulation and fibrinolytic factors include fibrinogens, fibrin degradation products (FDP), plasminogens, $\alpha_2$-plasmin inhibitors, antithrombin III, β-thromboglobulins, factor VIII, protein C, protein S and the like.

Examples of hormones include pituitary hormones (LH, FSH, GH, ACTH, TSH, prolactins), thyroid hormones ($T_3$, $T_4$, thyroglobulins), calcitonins, parathyroid hormones (PTH), adrenocortical hormones (aldosterone, cortisol), gonadal hormones (hCG, estrogen, testosterone, hPL), pancreatic and gastrointestinal hormones (insulin, C-peptide, glucagon, gastrin) and others (renin, angiotensin I & II, encephalin, erythropoietin) and the like.

Environmental hormones are exogenous endocrine-disrupting chemicals which are widely present in the environment and are incorporated into the body in the course of everyday activity, affecting reproduction, development, activity and other physiological endocrine functions. Examples of the aforementioned environmental hormones include nonylphenol, octylphenol, bisphenol A, butylbenzyl phthalate, tributyl tin, PCBs, poly(dibenzodioxin chloride), poly(dibenzofuran chloride), dioxins, DDT, DDE, DDD, endosulfan, methoxychlor, heptachlor, toxaphene, dieldrin, lindane, diethylstilbestrol (DES), ethynyl estradiol (in birth control pills), coumestrol, formononetein, genistein and the like.

Examples of the aforementioned drugs in blood include carbamazepine, primidone, valproic acid and other anti-epileptic drugs, digoxin, quinidine, digitoxin, theophylline and other circulatory disease drugs, gentamicin, kanamycin, streptomycin and other antibiotics and the like.

Examples of the aforementioned nucleic acids include cancer-related genes, hereditary disease-related genes, viral and bacterial genes and genes exhibiting polymorphisms which are called disease risk factors.

Examples of cancer-related genes include the k-ras gene, N-ras gene, p53 gene, BRCA1 gene, BRCA2 gene, src gene, ros gene, APC gene and the like.

Examples of hereditary disease-related genes include various genes for various hereditary metabolic disorders including phenylketonuria, alkaptonuria, cystinuria, Huntington's disease, Down's syndrome, Duchenne's muscular dystrophy, hemophilia and the like.

Examples of viral and bacterial genes include hepatitis C virus, hepatitis B virus, influenza virus, measles virus, HIV virus, *mycoplasma, Rickettsia, streptococcus* and *salmonella* bacillus genes and the like.

A gene exhibiting polymorphism is a gene having a base sequence which differs from individual to individual without necessarily having a direct association with a disease or the like, and examples include the PS1 (presenilin 1) gene, PS2 (presenilin 2) gene, APP (beta amyloid precursor protein) gene, lipoprotein genes, genes related to HLA (human leukocyte antigen) and blood type, and genes associated with the occurrence of high blood pressure, diabetes and the like.

These targets are often contained in specific test analytes. Examples of test analytes include bacteria, viruses and other pathogens, blood, sputum, tissue fragments and the like isolated from the body, and excreta such as urine, feces and the like. Moreover, in the case of pre-natal testing they may include fetal cells in amniotic fluid or a portion of divided egg cells in vitro. These analytes may also be first subjected to cell disruption by treatment with enzymes, heat, surfactants, ultrasound or a combination of these either directly or after being concentrated as sediments by centrifugation or the like as necessary.

(Functional Substance)

The functional substance of the present invention is a substance having affinity for a target. A functional substance to be amplified is a functional substance selected as having affinity for a target or a selected functional substance from which a specific substituent group has been removed. It is useful to include this substituent group removal when the selected functional substance has a substituent group which would impede amplification. The specific substituent group in this case is a substituent group which would impede amplification of the selected functional substance. This removal operation is unnecessary when there is no substituent group which would impede amplification. The functional substance manufactured by the present invention is a functional substance to be amplified or decomposition product thereof, or a substance comprising the functional substance to be amplified or decomposition product thereof.

These functional substances of the present invention are obtained by synthesizing functional substance candidates using the aforementioned modified nucleotide n-mer.

There are no particular limits on the number of nucleotide sequence connections in this case, which can be selected appropriately according to the object. For example a 10- to 100-mer is desirable and a 10- to 50-mer is more desirable.

There are no particular limits on the kind of affinity for the target, which can be biological adsorption, physical adsorption, electrical attraction, chemical adsorption or chemical bonding. For ease of selection a small dissociation constant (Kd) is desirable. For example, Kd is preferably $10^{-9}$ or less.

The affinity of the functional substance of the present invention for a target is preferably specific affinity, such as affinity only for a single specific target or specific affinity for targets having a specific structure (for example, affinity only for proteins having a specific base sequence or affinity only for proteins having a specific spatial arrangement).

(Specific Substituent Group)

A variety of substituent groups are introduced into functional substances for a variety of purposes including improving affinity for a target, increasing stability, facilitating synthesis and the like. Substituent groups bound to a base via a triple bond according to the present invention and the specific substituent groups are of this type.

A specific substituent group in the present invention is a substituent group included in a functional substance, and may be any substituent group as long as amplification of the functional substance can proceed when the substituent group is removed.

In a typical case of such a substituent group amplification does not progress when the substituent group is present but progresses when it is absent, but a substituent group is acceptable even if amplification progresses when it is present. This is because the object of the present invention, which is to analyze the structure of a specific substance, is achieved as long as amplification progresses once the specific substituent group is removed whether or not it impedes the progress of amplification. In some cases another type of substituent group may appear in place of the specific substituent group which is removed, but occurrence of such a different type of substituent group is acceptable as long as amplification progresses.

(Functional Substance Candidates)

There are no particular limits on the functional substance candidates in the present invention, and any which are obtained using the aforementioned modified nucleotide n-mer may be selected. There are no particular limits on the number of functional substance candidates, and a single functional substance could be selected from among thousands or tens of thousands of functional substance candidates.

(Selection)

There are no particular limits on the means of selection in the present invention, which may be chosen appropriately according to the object. In the case of a functional substance containing a modified nucleotide sequence, examples include affinity chromatography, filter binding, liquid-liquid separation, filtration, gel shift, density gradient centrifugation and various other methods. One or two or more of these may be used. Of these, affinity chromatography is desirable. Multiple functional substances may also be selected rather than one.

Affinity chromatography is a means of separation and purification using biological affinity in which specific components bind favorable to one another, and specifically when a functional substance contains a modified nucleotide sequence the target is fixed in a resin or other column packing material and equilibrated with a binding buffer, after which when a solution comprising functional substance candidates is poured into the column and left under fixed conditions a modified nucleotide sequence having affinity for the target is adsorbed by the column, and components other than the remaining modified nucleotide sequence can be removed by thorough washing with binding buffer. After that the functional substance comprising the aforementioned modified nucleotide sequence can be collected and selected by passing pure water or the aforementioned solution comprising the target through the column.

When the target itself is unknown and two or more are present (for example, in the case of organs or serum), the targets can be compartmentalized and fixed by mapping on a matrix with a one-dimensional to three-dimensional spatial arrangement, functional substance candidates can then be applied to the matrix in which the targets are compartmentalized and fixed, and functional substances which bind to the targets can be selected.

There are no particular limits on the method of fixing the target to the matrix, which can be selected appropriately according to the object, but when the target is a protein examples include the western blot method in which the target is treated by polyacrylamide electrophoresis (SDS-PAGE or the like) and transferred to a membranous matrix, and the dot blot and slot blot methods, in which a membranous matrix is directly impregnated with the target or a diluted solution thereof. Of these, the western blot method is preferred because it is capable of clearly detecting even proteins contained in minute quantities in cell extracts and other solutions with complex compositions. The western blot method combines the excellent separation ability of electrophoresis with the high specificity of an antigen-antibody reaction to detect specific proteins in protein mixtures, and is a method in which proteins are electrically moved and fixed from gel to a membranous matrix following SDS-PAGE, isoelectric focusing electrophoresis, two-dimensional electrophoresis or the like.

There are no particular limits on the membranous matrix, which can be selected appropriately according to the object, but highly hydrophobic nitrocellulose membranes to which proteins bind easily and highly hydrophobic PVDF (polyvinylidene difluoride) membranes and the like are desirable.

A pre-purification operation in which the synthesized functional substance candidates are separated from other substances can be added before the aforementioned selection step. The pre-purification operation can be performed by the same techniques used in the aforementioned separation, under conditions which are favorable for functional substances having affinity for a target and other functional substance candidates but not for other substances.

The functional substance may also be purified during the aforementioned selection step. Purification is preferably accomplished by liberating the functional substance from the target while monitoring the dissociation constant between the target and functional substance. This method is useful because it can efficiently select a functional substance having a desired dissociation constant in one initial operation. The dissociation constant can be set appropriately depending on the target, and can be measured for example by a measurement device using surface plasmon resonance.

In the selection step it is also possible to use the interactions of two or more substances with different dissociation constants, to select a functional substance by performing a washing operation adapted to a smaller dissociation constant, and to regenerate the support by performing a washing operation adapted to a larger dissociation constant. Even if there are two or more targets the support can be regenerated and multiple types of functional substances can be efficiently selected all at once with one support.

(Removal of Specific Substituent Group)

When it is difficult or impossible to amplify the selected functional substance as it is, it is useful to remove the specific substituent group that is the cause. There are no particular limits on the means of removal of the specific functional group in the present invention, and any known method may be adopted. Examples include cis-diol cleavage by periodic acid, silyl group cleavage by fluorine ions, and cleavage by photoreaction.

Figure 5:
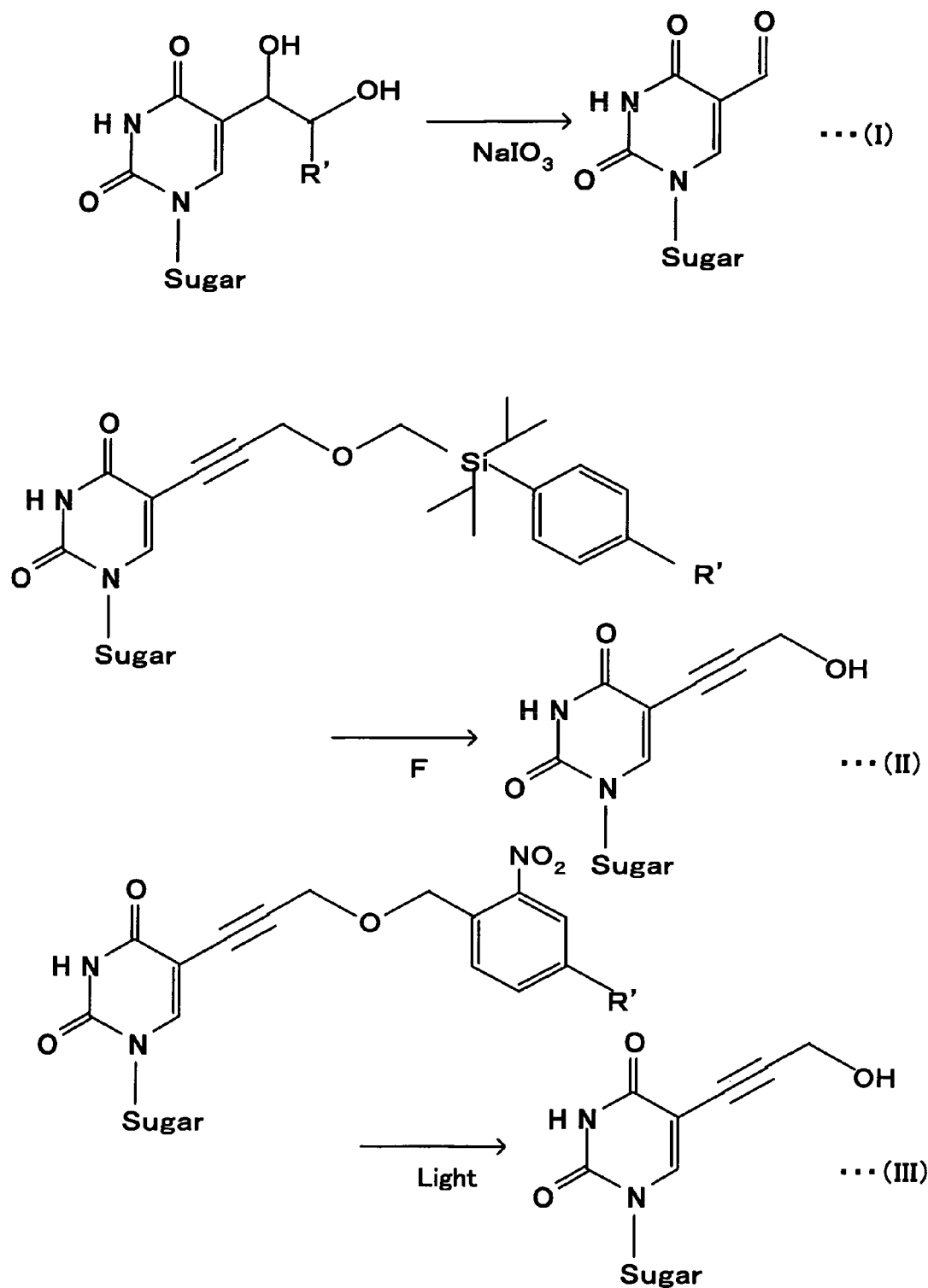
FIG. 5 shows examples of the reactions of cis-diol cleavage by means of periodic acid oxidation, silyl group cleavage by fluorine ions, and cleavage by a photoreaction.

In FIG. 5 cis-diol cleavage by periodic acid is shown by (I), silyl group cleavage by fluorine ions by (II), and cleavage by a photoreaction by (III). In each case, part of the substituent group of deoxy-5-substituted uridine is replaced with OH as a result of the cleavage.

Thus, in the present invention "removal of a specific substituent group" also includes such cases in which part of substituent groups is replaced. In other words, whether "removal of a specific substituent group" is achieved in the present invention is determined by whether subsequent amplification is possible.

A specific substituent group in the present invention may be a substituent group bound to a base via a triple bond of the present invention. Moreover, when using functional substances or candidates therefor in the present invention substituent groups (protective groups) may be introduced for such purposes as preventing side reactions during synthesis or conferring solubility in an organic solvent, and these protective groups may be identical to or different from the specific substituent groups of the present invention, or one may constitute part of the other.

The aforementioned protective groups are normally removed before determining the structure of the functional substance. Known methods can be used for this removal. Removal of protective groups is often performed before selection of the functional substance because this facilitates removal of substances other than the functional substance, but it may also be performed afterwards. The protective groups and specific substituent groups may also be removed in the same operation.

(Amplification)

Amplification in the present invention may be by any method capable of amplifying a selected functional substance either after or without removal of a specific group, and a known method can be selected as appropriate, but when the functional substance comprises a nucleotide sequence examples include PCR, LCR (ligase chain reaction), 3SR (self-sustained sequence replication), SDA (strand displacement amplification), RT-PCR, ICAN, LAMP and the like. One or two or more of these can be used. Of these, PCR is preferred.

PCR is explained simply here. PCR is a method which can amplify a specific oligonucleotide region hundreds of thousands of times by a repeated DNA synthesis reaction using a DNA replication enzyme in a test tube. In PCR, primers are elongated by a reaction in which four nucleotide triphosphates (deoxyadenosine triphosphate, deoxyguanosine triphosphate, deoxycytidine triphosphate and thymidine triphosphate or deoxyuridine triphosphate (a mixture thereof being sometimes called dNTP) are incorporated into the primers as substrates.

DNA replication enzymes which can be used for this elongation reaction include *E. coli* DNA polymerase I, *E. coli* DNA polymerase I Klenow fragment, T4 DNA polymerase and any other DNA polymerases, Taq DNA polymerase, Tth DNA polymerase, Vent DNA polymerase and the like.

(Determining the Structure of the Functional Substance)

There are no particular limits on the method of determining the structure of a functional substance in the present invention, and known methods can be adopted. "Structural determination" in determining the structure of a functional substance in the present invention may include determination of any kind of structure including molecular sequences and the like, but typically it means determining the nucleotide sequencing.

For the determination of the nucleotide sequences, DNA sequencers (automatic DNA base sequence determining apparatus) or the like using a method by gene cloning, a chain terminator method, the Sanger method, a dideoxy method, or the like, may be utilized, for example. One or two or more of these may be used.

In the aforementioned genetic cloning, host cells are genetically transformed by an expression vector into which the amplified nucleotide sequence has been incorporated, and this transformant is then prepared by culture or the like.

Examples of the aforementioned expression vector include plasmid vectors, phage vectors, plasmid-phage chimera vectors and the like. Examples of the aforementioned host cells include *E. coli, B. subtilis* and other prokaryotic microorganisms, yeasts and other eukaryotic microorganisms, animal cells and the like.

(Manufacture of Functional Substance)

When the aforementioned structural determination methods have been used for the functional substance, it can then be easily manufactured. There are no particular limits on the method used in this manufacturing stage, and any known method may be adopted. In this case, the functional substance can be manufactured efficiently by selecting the raw material composition.

Thus, the present invention permits easy structural determination and manufacture of a functional substance having high affinity for a target. This structural determination method and manufacturing method are applicable even to functional substances which cannot be amplified as they are.

Moreover, it is possible in many cases to simultaneously select and determine the structures of multiple functional substances and to simultaneously select multiple functional substances using multiple targets at the same time, and determine their structures. Selection and structural determination are also possible in many cases even if a target contains impurities.

Using the nucleoside, nucleotide n-mer, modified nucleotide sequence, substance having affinity for a target and constituent elements thereof of the present invention according to the aspects of the present invention described above, it is possible, for example, to promote screening and analysis of target structures (such as the structure of a protein sequence), and to apply the results to drugs, drug delivery, biosensors, control of expressed amounts of genes, cures for diseases caused by genetic abnormalities, functional elucidation of proteins translated by genes and the development of reaction catalysts and the like.

Examples of the present invention are explained below. The following methods were used for evaluation. The abbreviations and the like used below are explained thereafter.

(Mass Spectrometry)

A Bruker Daltonics MALDI-TOF MS (matrix laser-assisted desorption-ionization time of flight mass spectrometry) Autoflex II was used. For fat-soluble compounds 2 μL of a diluted sample solution (about 20 pmol/L) was mixed with 8 μL of an acetone solution of dithranol (10 mg/mL), and 1 μL was developed on a massive target and measured. A dithranol matrix was used as the internal standard for the calibration curve.

For water-soluble oligonucleotides, a diluted solution of the sample was first treated with a hydrogen ion-type ion exchange resin. A 1 μL 1:1 mixed aqueous solution of diammonium hydrogen citrate (DAC) and 3-hydroxypicolinic acid (HPA) was developed separately in advance on an Anchor Chip which was the TOF-MS target, and 1 μL of the sample solution was mixed in, slowly air dried and measured. A specified amount of a peptide mix sample for calibration curves was used as the standard substance for the calibration curve.

(NMR Analysis)

$^1$H-NMR measurement was done with about 10 mg of the sample dissolved in a deuterium solvent. The solvent peak was the basis for the internal standard. $^{31}$P-NMR measurement was done with PPh$_3$ as the external standard with a basis of 6.2 ppm. Measurement was carried out with a BCM (beam charge monitor).

Substance codes: the following roman numerals for substances match the roman numerals in the figures and formulae. Subsequent subscripts correspond to R in the figures and formulae. Subsequently, "base=A" and the like indicate types of bases. Lys signifies a lysine type, Tyr a tyrosine type, Ser a serine type, Typ a tryptophan type, Glu a glutamine type, Leu a leucine type and Phe a phenylalanine type. For example substance $V_{Lys}$base=A means that the substance has the structure indicated by V in FIG. 3, with R being the lysine type and the base being a group with an adenine skeleton.

Ph: Phenyl group

Pph$_3$: Triphenylphosphine

Et: Ethyl group

Me: Methyl group

Bt: Butyl group iPr: Isopropyl group

Bz Benzoyl group r.t.: Room temperature

Et$_3$N: triethylamine

Pyr: Pyridine

AcOH: Acetic acid

A: Group with adenine skeleton

G: Group with guanine skeleton

C: Group with cytosine skeleton

U: Group with uracil skeleton

DMTr: dimethyltrityl group

DMTrdU$^I$: Substance with structure at left of Formula 26. Superscript I indicates iodine.

P DMTrdNOH: Substance with structure at left of Formula 27

DIMAP Dimethylaminopyridine

TFA: Trifluoracetic acid

4-DMAP: 4-dimethylaminopyridine

DCC: Dicyclohexylcarbodiimide

TLC: Thin layer chromatography

HPLC: High performance liquid chromatography

THF: Tetrahydrofuran

DMF: Dimethylformamide

TBDMS: t-butyldimethylsilyl group

TBDPS: t-butyldiphenylsilyl group

HOBT: Hydroxybenzotriazole

DBU: Diazabicycloundecene

FMOC group: Fluorenylmethoxy group

Example 1

Synthesis of Substance I, Formula 26

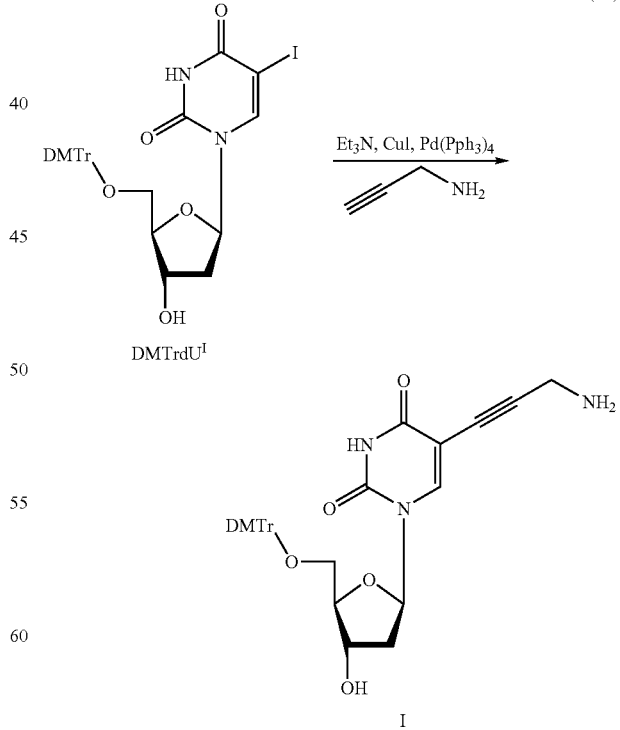

(26)

30.6 g (46.7 mmol) of DMTrdU$^I$ was dissolved in 470 mL of methylene chloride and substituted in argon atmosphere.

9.34 mL of Et₃N, 3.56 g of CuI, 10.8 g of Pd (Pph₃) and 4.81 mL of propagylamine were added to this solution, and agitated for 1 hour at room temperature. This reaction solution was directly loaded into silica gel and purified by chromatography (2% by volume Et₃N-containing dichloromethane-ethanol (volume ratio changed gradually from 1:0 to 9:1)) to obtain 29.3 g (purity 80% by weight according to NMR) of the target substance (yield 86%). The following reactions were accomplished using this crude product. A small amount was also purified by HPLC. The following data were obtained.

¹H-NMR (DMSO-d6) δ: 2.21 (1H, m), 3.10 (1H, dd, J=2.9, 10.4 Hz), 3.14 (2H, dt, J=10.6, 2.9 Hz), 3.21 (3H, m), 3.73 (6H, s), 3.91 (1H, m), 4.27 (1H, m), 5.32 (1H, br·d, J=2.9 Hz), 6.11 (1H, dd, J=6.4, 6.9 Hz), 6.88 (4H, d, J=8.8 Hz), 7.19-7.42 (9H, m), 7.89 (1H, s)

MALDI-TOF MS: Calculated value (C₃₃H₃₃N₃O₇Na)= 606.222 (M+Na)⁺, measured value=606.275

Example 2

Synthesis of Substance XIII, Formula 27

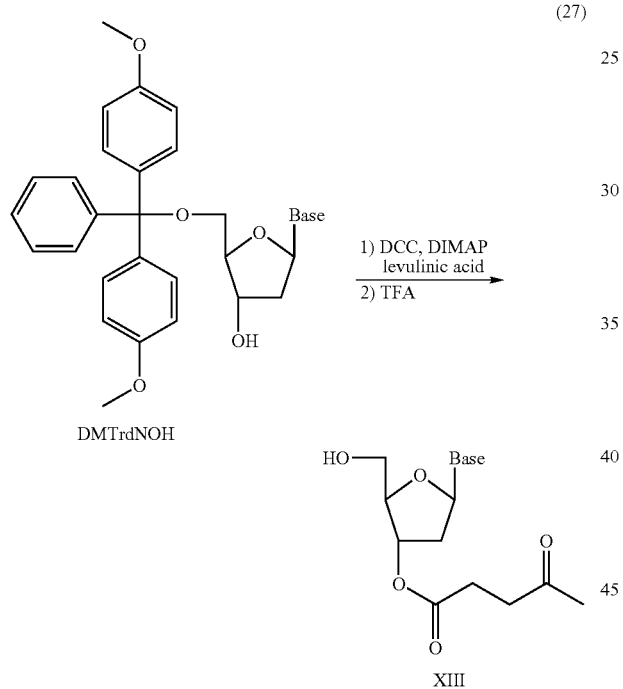

(27)

10 mmol of DMTrdNOH was dissolved in 50 mL of dehydrated dioxane, and 98 mg (0.8 mmol) of DIMAP, 4.12 g (20 mmol) of DCC and 2.06 mL (20 mmol) of levulinic acid were added and agitated at room temperature for 30 minutes. Next 5 mL of methanol was added and agitated for 15 minutes. The insoluble matter was filtered out and the filtrate was concentrated and dried. This residue was dissolved in 70 mL of dry methylene chloride and ice cooled, and 1.4 mL of trifluoracetic acid was added and agitated for 30 minutes at 0° C. This reaction solution was directly loaded onto silica gel and purified by chromatography (dichloromethane-ethanol, volume ratio varied from 1:0 to 9:1) to obtain substance XIII.

<In the case where Base=A>
Yield 3.86 g (85%)
¹H-NMR (DMSO-d6) δ: 2.13 (3H, s), 2.54 (3H, m), 2.77 (2H, t, J=6.4 Hz), 3.04 (1H, ddd, J=14.5, 8.9, 6.1 Hz), 3.63 (2H, m), 4.10 (1H, ddd, J=6.1, 2.8, 1.5 Hz), 5.20 (1H, t, J=5.3 Hz), 5.37 (1H, m), 6.49 (1H, dd, J=8.9, 6.2 Hz), 7.54 (2H, dd, J=7.5, 7.1 Hz), 7.64 (1H, tt, J=7.5, 2.0 Hz), 8.03 (2H, dt, J=7.1, 2.0 Hz), 8.71 (1H, s), 8.76 (1H, s), 11.23 (1H, s).

<In the case where Base=G>
Yield 3.77 g (87%)
¹H-NMR (DMSO-d6) δ: 1.11 (3H, d, J=6.8 Hz), 2.18 (3H, s), 2.48 (3H, m), 2.75 (3H, m), 2.82 (1H, m), 3.57 (2H, m), 4.01 (1H, ddd, J=5.9, 2.8, 1.6 Hz), 5.11 (1H, br·t, J=4.6 Hz), 5.29 (1H, m), 6.20 (1H, dd, J=9.0, 65.5 Hz), 8.26 (1H, s), 8.71 (1H, s), 11.69 (1H, br·s), 12.07 (1H, s).

<In the case where Base=C>
Yield 3.80 (89%)
¹H-NMR (DMSO-d6) δ: 2.12 (3H, s), 2.21 (1H, m), 2.47 (3H, m), 2.74 (2H, t, J=6.4 Hz), 3.64 (2H, m), 3.63 (2H, m), 4.10 (1H, m), 5.20 (2H, m), 6.16 (1H, dd, J=7.7, 6.0 Hz), 7.37 (1H, d, J=7.4 Hz), 7.50 (2H, dd, J=7.5, 7.1 Hz), 7.62 (1H, t, J=7.1 Hz), 8.00 (2H, d, J=7.5 Hz), 8.36 (1H, d, J=7.4 Hz), 11.23 (1H, s)

<In the case where Base=T>
Yield 3.14 g (92%)
¹H-NMR (DMSO-d6) δ: 1.76 (3H, d, J=1.2 Hz), 2.10 (3H, s), 2.16 (1H, ddd, J=14.4, 6.0, 2.0 Hz), 2.16 (1H, ddd, J=14.4, 9.0, 6.2 Hz), 2.48 (2H, m), 2.73 (2H, t, J=6.3 Hz), 3.64 (2H, m), 3.63 (2H, m), 3.93 (1H, m), 5.20 (2H, m), 6.16 (1H, dd, J=9.0, 6.0 Hz), 7.72 (1H, d, J=1.2 Hz), 11.35 (1H, s).

Example 3

Synthesis of Substance IV, Formula 28

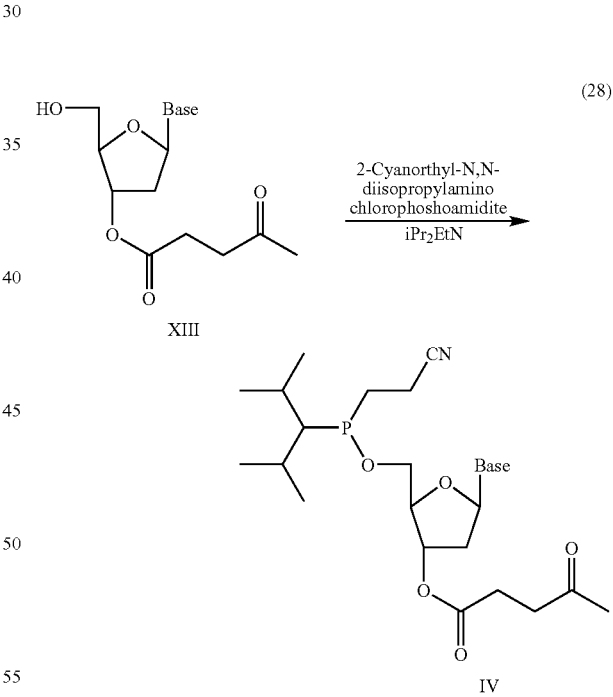

(28)

Substance XIII (5 mmol) was azeotropically dehydrated 3 times with dry methylene chloride and dried. This was dissolved in 20 mL of dry methylene chloride and cooled to 0° C. after addition of diisopropylethylamine (1.31 mL, 7.5 mmol). A dry methylene chloride solution (5.0 mL) of diisopropylchlorophosphoramidite (1.34 mL, 6.0 mol) was then dripped in. After 1 hour of agitation, methanol was added to inactivate the excess amidite-forming reagent, and this was diluted with methylene chloride, and washed with a saturated aqueous sodium bicarbonate solution and a saturated aqueous sodium chloride solution. It was then purified by intermediate pressure chromatography (2% by volume Et$_3$N-containing dichloromethane-EtOH (volume ratio gradually changed from 1:0 to 9:1) to obtain substance IV.

<In the case where Base=A>

Yield 2.67 g (82%)

$^1$H-NMR (DMSO-d6) δ: 1.08 (12H, m), 2.13 (3H, s), 2.56 (1H, m), 2.74 (3H, m), 3.13 (1H, m), 3.51 (2H, m), 3.92-3.65 (4H, m), 4.23 (1H, m), 5.43 (1H, m), 6.51 (1H, m), 7.54 (2H, dd, J=7.5, 7.1 Hz), 7.64 (1H, tt, J=7.5, 2.0 Hz), 8.03 (2H, dt, J=7.1, 2.0 Hz), 8.63 (1/2H, s), 8.64 (1/2H, s), 8.74 (1H, s), 11.21 (1H, s).

$^{31}$P-NMR (120 MHz, DMSO-d6) δ: 148.02

MALDI-TOF MS: Calculated value (C$_{31}$H$_{41}$N$_7$O$_7$P)= 654.2805 [M+H]$^+$, measured value=654.112

<In the case where Base=G>

Yield 2.93 g (92%)

$^1$H-NMR (DMSO-d6) δ: 1.08 (18H, m), 2.12 (3H, s), 2.47 (1H, m), 2.75 (5H, m), 2.86 (1H, m), 3.53 (2H, m), 3.74 (4H, m), 4.17 (1H, m), 5.31 (1H, m), 6.24 (1H, m), 8.18 (1/2H, s), 8.19 (1/2H, s), 11.71 (1H, br·s), 12.04 (1H, br·s)

$^{31}$P-NMR (120 MHz, DMSO-d6) δ: 148.14, 147.47

MALDI-TOF MS: Calculated value (C$_{28}$H$_{43}$N$_7$O$_8$P)= 636.2911 [M+H]$^+$, measured value=636.133

<In the case where Base=C>

Yield 2.45 g (78%)

$^1$H-NMR (DMSO-d6) δ: 1.12 (12H, m), 2.15 (3H, s), 2.26 (1H, m), 2.51 (1H, m), 2.77 (4H, m), 3.55 (2H, m), 3.80 (4H, m), 4.27 (1H, m), 5.22 (1H, m), 6.15 (1H, m), 7.37 (1H, br·d, J=7.4 Hz), 7.50 (2H, dd, J=7.5, 7.2 Hz), 7.62 (1H, tt, J=7.5, 1.3 Hz), 8.00 (2H, dt, J=7.2, 1.3 Hz), 8.21 (1/2H, d, J=7.4 Hz), 8.22 (1/2H, d, J=7.4 Hz), 11.29 (1H, s)

$^{31}$P-NMR (120 MHz, DMSO-d6) δ: 148.33, 147.08

MALDI-TOF MS: Calculated value (C$_{30}$H$_{41}$N$_5$O$_8$P)= 630.2693 [M+H]$^+$, measured value=630.130

<In the case where Base=T>

Yield 2.47 g (92%)

$^1$H-NMR (DMSO-d6) δ: 1.12 (12H, m), 1.77 (3/2H, d, J=1.1 Hz), 1.78 (3/2H, d, J=1.1 Hz), 2.10 (3H, s), 2.26 (2H, m), 2.50 (2H, m), 2.76 (4H, m), 3.56 (2H, m), 3.77 (4H, m), 4.10 (1H, m), 5.15 (1/2H, m), 5.21 (1/2H, m), 6.14 (1/2H, dd, J=7.5, 7.0 Hz), 6.20 (1/2H, dd, J=7.9, 6.2 Hz), 7.50 (1/2H, d, J=1.1 Hz), 7.60 (1/2H, d, J=1.1 Hz), 11.38 (1H, s)

$^{31}$P-NMR (120 MHz, DMSO-d6) δ: 148.33, 147.08

Example 4

Synthesis of trifluoroacetylaminocaproic Acid, Formula 29

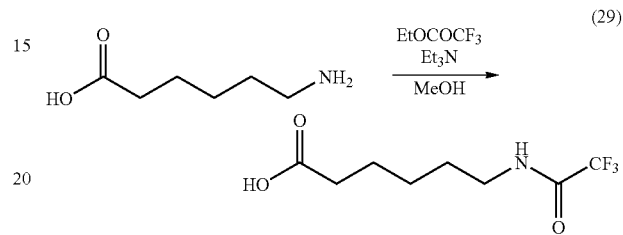

ω-aminocaproic acid (2.59 g, 19.7 mol) was dissolved in 100 mL methanol, and triethylamine (4.2 mL, 29.9 mmol) and ethyl trifluoroacetate (3.5 mL, 29.5 mmol) were added and agitated for a day and night at room temperature. The reaction solution was poured into 1% by weight hydrochloric acid (100 mL), and extracted once with methylene chloride. The methylene chloride layer was washed once with water and once with a saturated aqueous sodium chloride solution, and then dried and concentrated with anhydrous sodium sulfate to obtain 2.78 g of a crude product.

$^1$H-NMR (CDCl$_3$) δ: 1.39 (2H, m), 1.63 (4H, m), 2.36 (2H, t, J=7.3 Hz), 3.36 (2H, q, J=6.8 Hz), 6.42 (1H, br·s)

Example 5

Monomer: Synthesis of Substance II$_{Lys}$, Formula 30

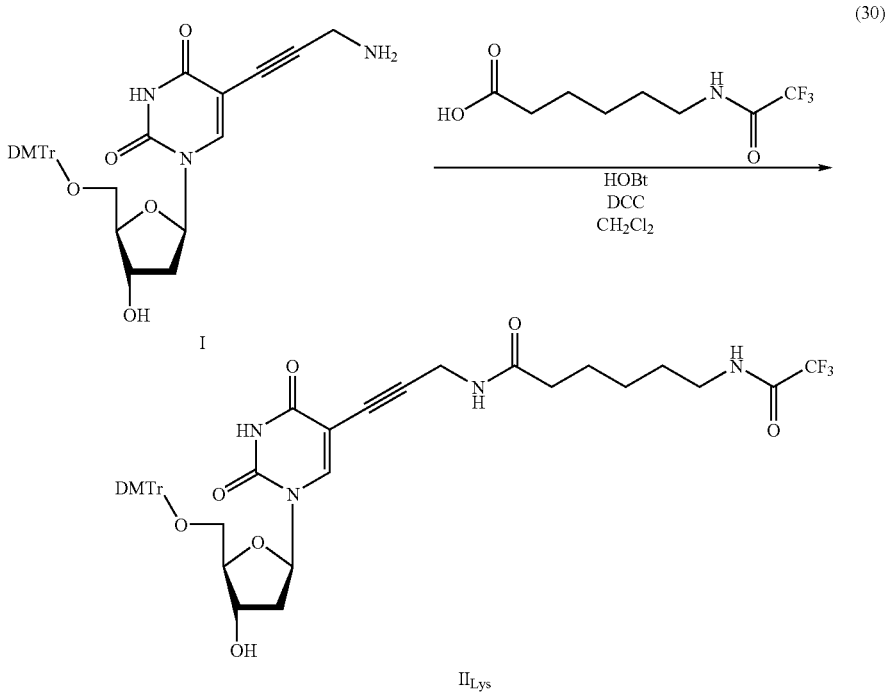

1.23 g (5.41 mmol) of crude ω-trifluoroacetylaminocaproic acid product and 0.92 g (6.01 mmol) of hydroxybenzotriazole monohydrate were dissolved in 54 mL of dry methylene chloride. 1.16 g (5.76 mmol) of dicyclohexylcarbodiimide was added to this solution, which was agitated for 35 minutes at room temperature and cooled to 0° C., and 10 mL of a dehydrated methylene chloride solution of substance I (3.65 g, 80% by weight, 5.00 mmol) was dripped in over the course of 5 minutes. After 1 hour of agitation at 0° C., this was warmed to roomed temperature. The sediment was filtered and extracted 3 times with ethyl acetate after addition of a saturated aqueous sodium bicarbonate solution. After the combined organic layer had been washed with a saturated aqueous sodium chloride solution the organic layer was dried with sodium sulfate, and concentrated. The residue was purified by intermediate pressure chromatography (dichloromethane-ethanol, volume ratio raised gradually from 1:0 to 9:1) to obtain 3.40 g (yield 86%) of the target product, $II_{Lys}$.

$^1$H-NMR (DMSO-d6) δ: 1.21 (2H, m), 1.45 (4H, m), 2.06 (2H, t, J=7.4 Hz), 2.18 (1H, m, C(2)'H), 2.28 (1H, dd, J=6.8, 13.5 Hz), 3.06 (1H, dd, J=2.9, 10.4 Hz), 3.14 (2H, dt, J=6.0, 6.7 Hz), 3.25 (1H, dd, J=5.4, 10.4 Hz), 3.73 (3H, s), 3.73 (3H, s), 3.88 (2H, d, J=5.3 Hz), 3.89 (1H), 4.26 (1H, m), 5.33 (1H, d, J=4.6 Hz), 6.09 (1H, dd, J=6.4, 7.0 Hz), 6.88 (2H, d, J=9.0 Hz), 6.89 (2H, d, J=9.0 Hz), 7.15-7.35 (7H, m), 7.39 (2H, d, J=7.2 Hz), 7.90 (1H, s), 8.17 (1H, t, J=5.3 Hz), 9.39 (1H, t, J=6.0 Hz), 11.66 (1H, br)

MALDI-TOF MS: Calculated value $(C_{41}H_{44}F_3N_4O_9)$= 793.306 $[M+H]^+$, measured value=793.297 $[M+H]^+$ Example 6

Monomer Amidite: Synthesis of Substance $III_{Lys}$, Formula 31

Substance $II_{Lys}$ (0.517 g, 0.655 mol) was azeotropically dehydrated 3 times with 1 mL dry acetonitrile and dried. This was dissolved in 2.3 mL of dry acetonitrile, and cooled to 0° C. after addition of diisopropylethylamine (167 μL, 0.982 mmol). A dry acetonitrile solution (1.0 mL) of diisopropylchlorophosphoramidite (0.199 g, 0.841 mol) was dripped in. After 1 hour of agitation, methanol was added to inactivate the excess amidite-forming reagent, and this was diluted with methylene chloride, and washed with a saturated aqueous sodium bicarbonate solution and a saturated aqueous sodium chloride solution. This was purified by intermediate pressure chromatography (2% by volume $Et_3N$-containing dichloromethane:hexane, volume ratio changed gradually from 1:1 to 1:0, followed by 2% by volume $Et_3N$-containing dichloromethane:ethanol, volume ratio changed gradually from 1:0 to 19:1) to obtain 0.586 g of the substance $III_{Lys}$ (yield 87%).

$^1$H-NMR (300 MHz, DMSO-d6) δ: 0.97 (3H, d, J=6.6 Hz), 1.10 (9H, m), 1.21 (2H, m), 1.44 (4H, m), 2.05 (2H, t, J=7.1 Hz), 2.30 (1H, m), 2.41 (1H, m), 2.64 (2H×1/2, t, J=5.7 Hz), 2.75 (2H×1/2, t, J=5.8 Hz), 3.13 (2H, m), 3.13 (1H, m), 3.28 (1H, m), 3.50 (2H, m), 3.61 (2H×1/2, m), 3.70 (2H×1/2, m), 3.72 (6H, s), 3.89 (2H×1/2, d, J=5.1 Hz), 3.92 (2H×1/2, d, J=5.3 Hz), 4.01 (1H×1/2, br), 4.05 (1H×1/2, br), 4.48 (1H, br), 6.08 (1H, m), 6.07 (1/2H, m) 6.09 (1/2H, m), 6.86 (2H, d, J=8.8 Hz), 6.88 (2H, d, J=8.8 Hz), 7.15-7.35 (7H, m), 7.39 (2H, br·d, J=7.3 Hz), 7.94 (1/2H, s), 7.95 (1/2H, s), 8.18 (1/2H, br), 8.20 1/2H, br), 9.39 (1H, br), 11.67 (1H, br)

$^{31}$P-NMR (120 MHz, DMSO-d6) δ: 147.62, 148.02

MALDI-TOF MS: Calculated value $(C_{50}H_{61}F_3N_6O_{10}P^+)$= 993.413 $[M+H]^+$, measured value=993.400 $[M+H]^+$ (31)

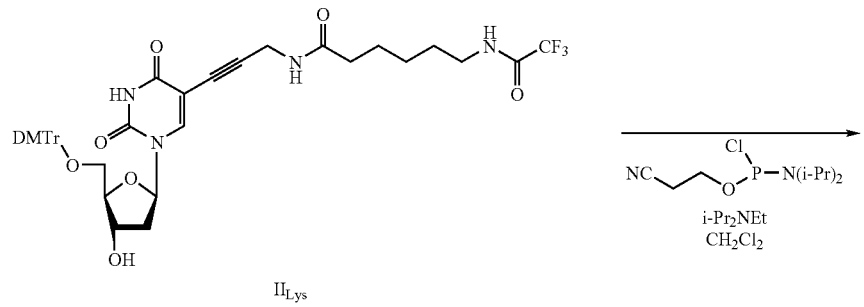

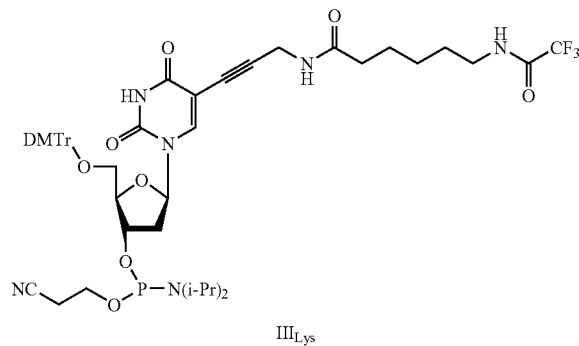

Example 7

Dimer: Synthesis of substance V$_{Lys}$base=A,
Formula 32

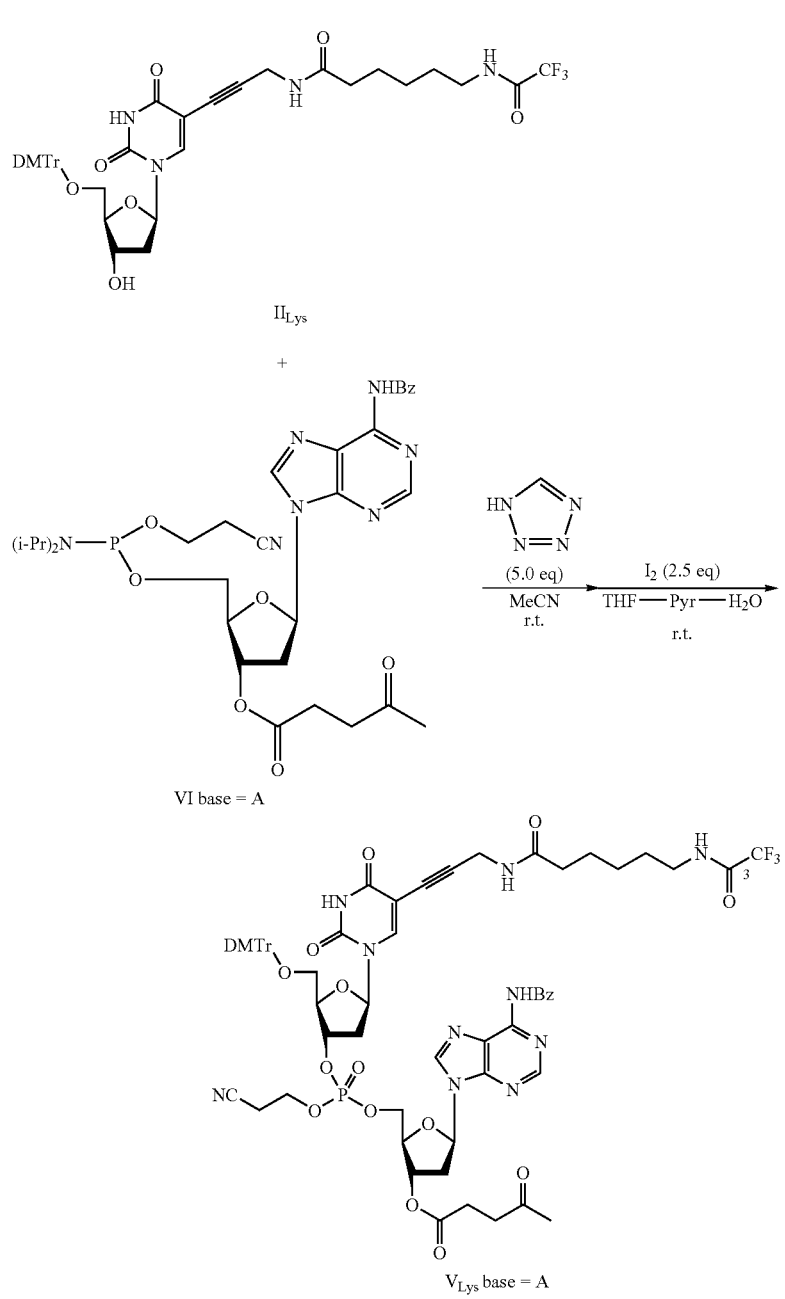

(32)

Substance II$_{Lys}$ (2.24 g, 2.83 mmol) and N-benzoyl-3'-levuloyladenosine 5'-(diisopropylamino) cyanoethylphosphoramidite (substance VIbase=A, 2.22 g, 3.40 mmol) were measured in a 200 mL pear-shaped flask, azeotroped 3 times with dry acetonitrile and dried with a vacuum pump. 31.5 mL (tetrazole 15.8 mmol) of an 0.45 mol/L tetrazole/acetonitrile solution was added and agitated for 30 minutes at room temperature. Saturated aqueous sodium bicarbonate solution was added to neutralize the reaction system, which was then extracted 3 times with methylene chloride. The combined methylene chloride layer was washed with a saturated aqueous sodium chloride solution and dried and concentrated with anhydrous sodium sulfate.

The resulting residue was dissolved in 42 mL THF, 14 mL pyridine and 7 mL water, and 2.16 g (8.50 mmol) of iodine was added and agitated for 30 minutes at room temperature. The reaction system was then diluted with methylene chloride, a 5% by weight aqueous sodium sulfite solution was added to reduce the excess iodine, and the water layer was then extracted twice with methylene chloride. The combined methylene chloride layer was dried with anhydrous sodium sulfate, and purified by intermediate pressure chromatography (dichloromethane-ethanol, volume ratio changed gradually from 1:0 to 9:1) to obtain 3.24 g (yield 84%) of the target product, $V_{Lys}$base=A.

$^1$H-NMR (DMSO-d6) δ: 1.21 (2H, m), 1.45 (4H, m), 2.05 (2H, t, J=7.4 Hz), 2.10 (3H×1/2, s), 2.10 (3H×1/2, s), 2.40-2.55 (6H, m), 2.74 (2H, m), 2.82 (2H, t, J=5.9 Hz), 3.05-3.20 (4H, m), 3.28 (1H, m), 3.89 (2H, br), 4.09 (3H, m), 4.27 (3H, m), 4.98 (1H, m), 6.09 (1H, dd, J=5.9, 6.8 Hz), 6.50 (1H, m), 6.86 (4H, d, J=7.0 Hz), 7.20-7.40 (9H, m), 7.53 (2H, dd, J=7.0, 7.3 Hz)), 7.64 (1H, J=7.0 Hz), 7.89 (1/2H, s), 7.90 (1/2H, s), 8.02 (2H, d, J=7.3 Hz), 8.17 (1H, m), 8.63 (1/2H, s), 8.63 (1/2H, s), 8.72 (1H, s), 9.38 (1H, s), 11.20 (1H, br), 11.69 (1H, br)

$^{31}$P-NMR (120 MHz, DMSO-d6) δ: −2.16, −2.06

MALDI-TOF MS: Calculated value ($C_{66}H_{68}F_3N_{10}NaO_{17}P^+$)=1383.4346 [M+Na]$^+$, measured value=1383.200 [M+Na]$^+$, Example 8

Dimer Levuloyl Removal: Synthesis of Substance $VI_{Lys}$base=A, Formula 33

The substance $V_{Lys}$base=A (3.24 g, 2.38 mol) was dissolved in 64 mL of a mixed pyridine-acetic acid solvent (volume ratio 8:2), and hydrazine monohydrate (1.10 mL, 22.63 mol) was added and agitated for 10 minutes at room temperature. After addition of a suitable amount of acetone at 0° C. to convert excess hydrazine to azone, this was diluted with methylene chloride, and the excess acetic acid was neutralized with a saturated aqueous sodium bicarbonate solution. After three extractions with methylene chloride, the combined methylene chloride layer was washed with a saturated aqueous sodium chloride solution, dried with anhydrous sodium sulfate and concentrated. The resulting residue was purified by intermediate pressure chromatography (dichloromethane:ethanol, volume ratio changed gradually from 1:0 to 9:1) to obtain 2.23 g (yield 74%) of the target product, $VI_{Lys}$base=A.

$^1$H-NMR (300 MHz, DMSO-d6) δ: 1.21 (2H, m), 1.45 (4H, m), 2.05 (2H, t, J=6.5 Hz), 2.40 (1H, m), 2.50 (2H, m), 2.82 (2H, br·t, J=5.5 Hz), 2.88 (1H, m), 3.13 (3H, m), 3.30 (1H, m), 3.70 (3H, s), 3.70 (3H, s), 3.89 (2H, br·m), 4.0-4.3 (6H, m), 4.50 (1H, m), 4.99 (1H, m), 5.59 (1H, d, J=4.2 Hz), 6.09 (1H, dd, J=6.8, 7.2 Hz), 6.48 (1H, m), 6.86 (4H, d, J=8.8 Hz), 7.15-7.30 (7H, m), 7.36 (2H, d, J=7.3 Hz), 7.53 (2H, dd, J=7.5, 7.2 Hz), 7.64 (1H, t, J=7.2 Hz), 7.89 (1/2H, s), 7.91

(33)

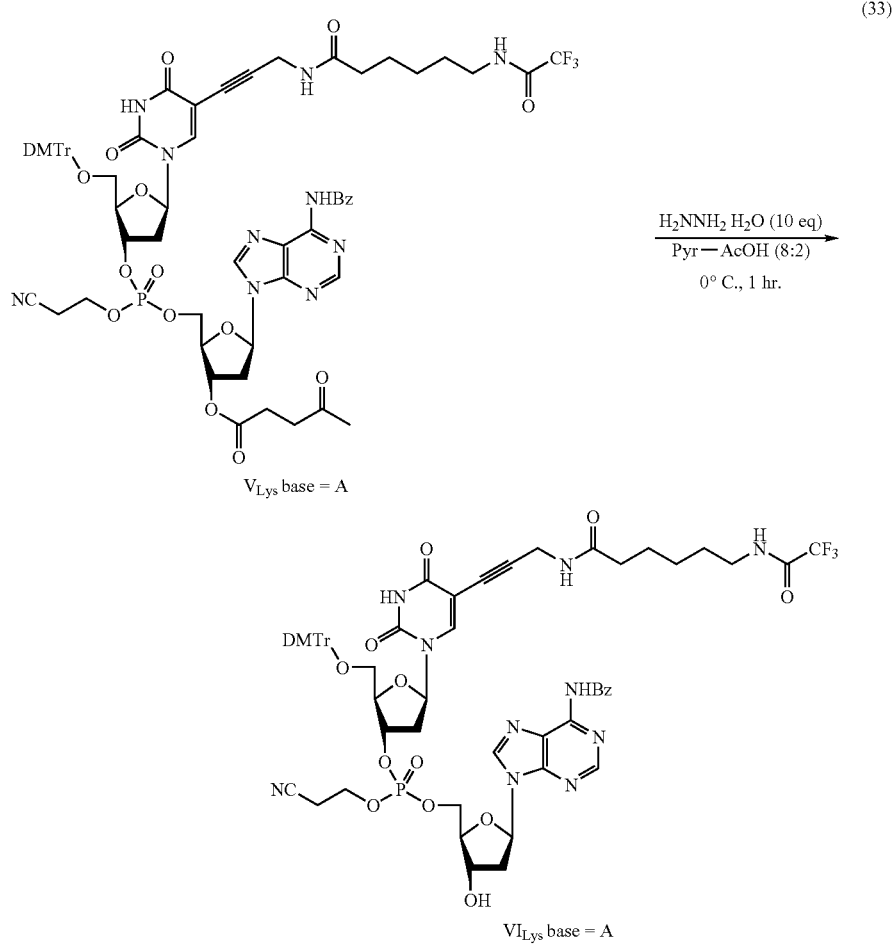

(1/2H, s), 8.02 (2H, d, J=7.5 Hz), 8.19 (1H, br), 8.59 (1/2H, s), 8.60 (1/2H, s), 8.71 (1H, m), 9.40 (1H, br), 11.19 (1H, s), 11.70 (1H, s)

$^{31}$P-NMR (120 MHz, DMSO-d6) δ: −2.14, −2.01

MALDI-TOF MS: Calculated value $(C_{61}H_{62}F_3N_{10}NaO_{15}P^+)$=1285.3978 [M+Na], measured value=1285.187 [M+Na]

Example 9

Dimer Amidite: Synthesis of Substance $V_{Lys}$base=A, Formula 34

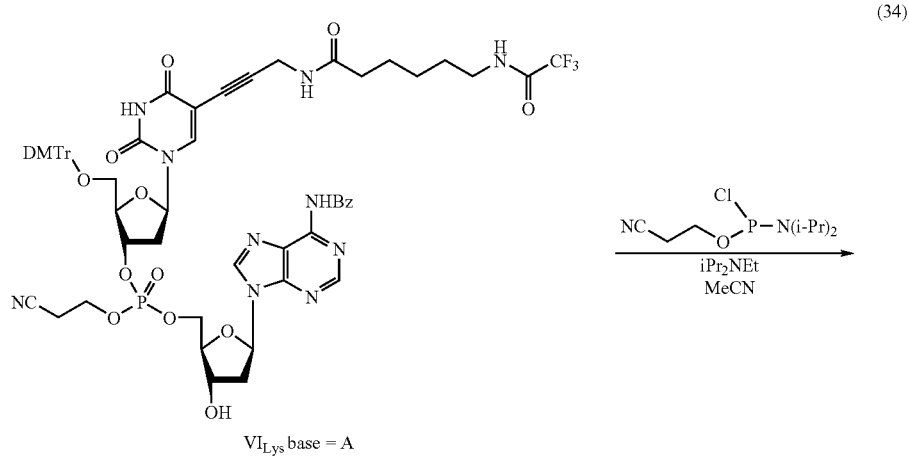

(34)

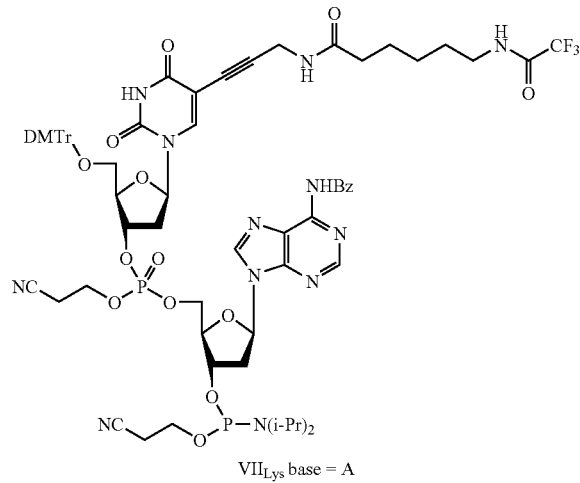

Substance $VI_{Lys}$base=A (1.66 g, 1.31 mmol) was azeotropically dehydrated three times with dry acetonitrile, and thoroughly dried with a vacuum pump. 13 mL of acetonitrile was added, followed by diisopropylethylamine (298 μL, 1.71 mmol), and the mixture was cooled to 0° C. and agitated for 1 hour at 0° C. after addition of diisopropylchlorophosphoramidite (0.35 mL, 1.58 mmol).

After addition of 1.3 mL methanol to inactivate the excess amidite-forming reagent, this was diluted with methylene chloride, and washed with a saturated aqueous sodium bicarbonate solution and a saturated aqueous sodium chloride solution. The solvent was removed under reduced pressure and the residue was purified by intermediate pressure chromatography (2% by volume Et$_3$N-containing dichloromethane:ethanol, volume ratio gradually changed from 1:0 to 9:1) to obtain 1.56 g of the target product, $VII_{Lys}$base=A (yield 81%).

$^1$H-NMR (300 MHz, DMSO-d6) δ: 1.16 (14H, m), 1.44 (4H, m), 2.05 (2H, m), 2.50 (2H, m), 2.52 (1H, m), 2.80 (4H, m), 3.00-3.20 (4H, m), 3.30 (1H, m), 3.60 (2H, m), 3.70 (6H, s), 3.77 (2H, m), 3.89 (2H, s), 4.00-4.35 (6H, m), 4.79 (1H, m), 4.98 (1H, m), 6.09 (1H, br·dd, J=6.4, 6.9 Hz), 6.49 (1H, m), 6.85 (4H, d, J=8.3 Hz), 7.10-7.30 (7H, m), 7.36 (2H, d, J=7.5 Hz), 7.56 (2H, dd, J=7.2, 7.5 Hz), 7.64 (1H, t, J=7.2 Hz), 7.90 (1H, s), 8.02 (2H, d, J=7.5 Hz), 8.17 (1H, br), 8.60 (1H, br), 8.71 (1H, br), 9.38 (1H, br), 11.19 (1H, s), 11.69 (1H, s)

$^{31}$P-NMR (120 MHz, DMSO-d6) δ: −2.14, −2.09, 148.35, 148.42

MALDI-TOF MS: Calculated value $(c_{70}H_{79}F_3N_{12}NaO_{16}P_2^+)$=1485.5057 [M+Na]$^+$, measured value=1485.376 [M+Na]$^+$

Example 10

Synthesis of Substance at Right of Formula 35

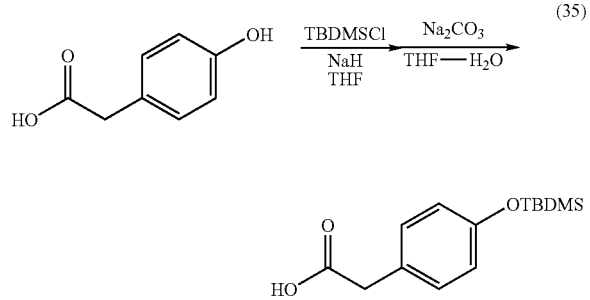

(35)

(4-hydroxyphenyl)acetic acid (2.25 g, 14.8 mmol) was added slowly as a solid at 0° C. to a THF suspension of sodium hydride (1.18 g, 29.6 mmol), and agitated. About 5 minutes later a THF solution of t-butyldimethylsilylchloride (4.45 g, 29.5 mmol) was added. Once the reaction had subsided, this was warmed to room temperature and agitated. Sodium carbonate (15.6 g, 147.4 mmol) was then added as a solid, and water was added and agitated. Once completion of the reaction had been confirmed by TLC, ammonium chloride (18.9 g, 354.0 mmol) was added as a solid, and water was added and agitated. After concentration under reduced pressure, the residue was washed with dichloromethane and the organic matter was removed. This solution was concentrated and purified by intermediate pressure column chromatography (hexane-dichloromethane, volume ratio changed gradually from 1:0 to 0:1, followed by dichloromethane-acetic acid 98:2) to obtain the target carboxylic acid (3.2638 g, yield 83%).

Example 11

Monomer: Synthesis of Substance $II_{Tyr}$, Formula 36

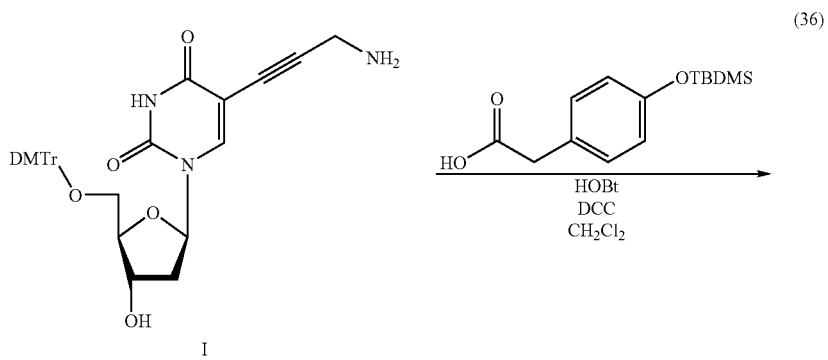

(36)

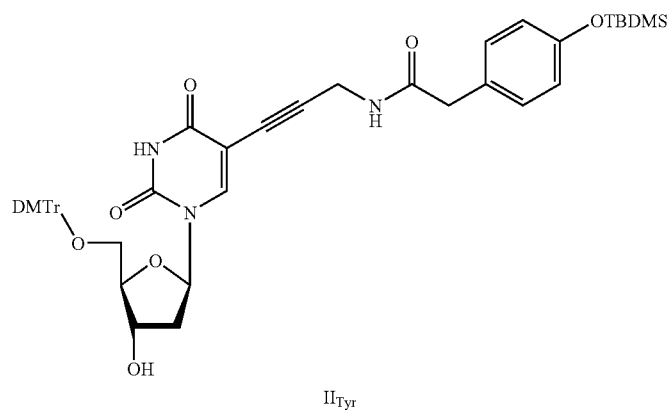

$II_{Tyr}$

A dichloromethane solution of (4-(t-butyldimethylsilyloxy)phenyl)acetic acid (1.61 g, 6.03 mmol) was added to 1.12 g (7.28 mmol) of N-hydroxybenzotriazole hydrate, and agitated. Next, a dichloromethane solution of dicyclohexylcarbodiimide (1.49 g, 7.23 mmol) was added and agitated for 30 minutes. This was cooled to 0° C., a dichloromethane solution of substance I (4.36 g, 80% by weight, 5.97 mmol) was added and the mixture was agitated for about 2 more hours at 0° C. After completion of the reaction had been confirmed by TLC, the dicyclohexylurea was removed by filtration. This was extracted as it was with dichloromethane after addition of water, washed with water once more, and dried with anhydrous sodium sulfate. Filtration of the drying agent was followed by concentration under reduced pressure. Purification by intermediate pressure column chromatography (dichloromethane-ethyl acetate, volume ratio changed slowly from 1:0 to 0:1) yielded 4.01 g of the target product, II$_{Tyr}$ (yield 80%).

$^1$H-NMR (300 MHz, DMSO-d6) δ: 0.15 (6H, s), 0.93 (9H, s), 2.18 (1H, m), 2.25 (1H, dd, J=6.6, 12.1 Hz), 3.07 (1H, m), 3.25 (1H, m), 3.33 (2H, s), 3.72 (6H, s), 3.88 (1H, m), 3.99 (2H, d, J=5.1 Hz), 4.27 (1H, m), 6.29 (1H, d, J=4.4 Hz), 6.09 (1H, dd, J=6.6, 6.8 Hz), 6.74 (2H, d, J=8.4 Hz), 6.87 (2H, d, J=8.8 Hz), 6.88 (2H, d, J=8.8 Hz), 7.10 (2H, d, J=8.4 Hz), 7.15-7.30 (7H, m), 7.38 (2H, d, J=7.2 Hz), 7.89 (1H, s), 8.37 (1H, br, t, J=5.1 Hz), 11.63 (1H, br·s)

MALDI-TOF MS: Calculated value (C$_{47}$H$_{54}$N$_3$O$_9$Si$^+$)= 832.3624 [M+H]$^+$, measured value=832.083 [M+H]$^+$ Example 12

Amidite: Synthesis of Substance III$_{Tyr}$, Formula 37

After removal of water from 0.334 g (0.402 mmol) of Substance II$_{Tyr}$ by azeotroping (3 times) with acetonitrile, it was dried with a vacuum pump. This amide was dissolved in 4 mL of acetonitrile in an argon atmosphere, and an 0.5 mL acetonitrile solution of 80 µL (0.470 mmol) diisopropylethylamine and an 0.5 mL acetonitrile solution of 0.109 g (0.461 mmol) 2-cyanoethyldiisopropyl chlorophosphoramidite were added and agitated for about 1 hour. After completion of the reaction had been confirmed by TLC, methanol was added and agitated for 30 minutes. After addition of water, this was extracted twice with dichloromethane, washed with an aqueous sodium chloride solution and dried with anhydrous sodium sulfate. After filtration of the drying agent this was concentrated under reduced pressure. Purification by intermediate pressure column chromatography (2% by volume Et$_3$N-containing dichloromethane:hexane, volume ratio changed gradually from 1:1 to 1:0, followed by 2% by volume Et$_3$N-containing dichloromethane-acetone, volume ratio changed gradually from 1:0 to 4:1) yielded 0.305 g of the target product, III$_{Tyr}$ (yield 74%).

$^1$H-NMR (300 MHz, DMSO-d6) δ: 0.16 (6H, s), 0.93 (9H, s), 0.98 (3H, d, J=7.3 Hz), 1.10 (3H, d, J=6.8 Hz), 1.11 (3H, d, J=6.8 Hz), 1.12 (3H, d, J=6.8 Hz), 2.32 (1H, m), 2.42 (1H, m), 2.64 (2H×1/2, t, J=5.7 Hz), 2.75 (2H×1/2, t, J=5.7 Hz), 3.15 (1H, m), 3.30 (1H, m), 3.33 (2H s), 3.48 (2H, m), 3.52 (2H, m), 3.72 (3H, s), 3.72 (3H, s), 3.91 (2H×1/2, d, J=5.1 Hz), 3.94 (2H×1/2, d, J=5.1 Hz), 4.03 (1/2H, m), 4.06 (1/2H, m), 4.48 (1H, m), 6.08 (1/2H, t, J=6.6 Hz), 6.10 (1/2H, t, J=6.6 Hz), 6.74 (2H, d, J=8.3 Hz), 6.86 (2H, d, J=8.7 Hz), 6.88 (2H, d, J=8.7 Hz), 7.11 (2H, d, J=7.9 Hz), 7.15-7.35 (7H, m), 7.39 (2H, br·d, J=7.7 Hz), 7.94 (1/2H, s), 7.94 (1/2H, s), 8.39 (1/2H, t, J=5.1 Hz), 8.40 (1/2H, t, J=5.1 Hz), 11.56 (1H, br)

$^{31}$P-NMR (120 MHz, DMSO-d6) δ: 147.62, 148.00

MALDI-TOF MS: Calculated value (C$_{56}$H$_{71}$N$_5$O$_{10}$PSi$^+$)= 1032.4702 [M+H]$^+$, measured value=1032.533 [M+H]$^+$ (37)

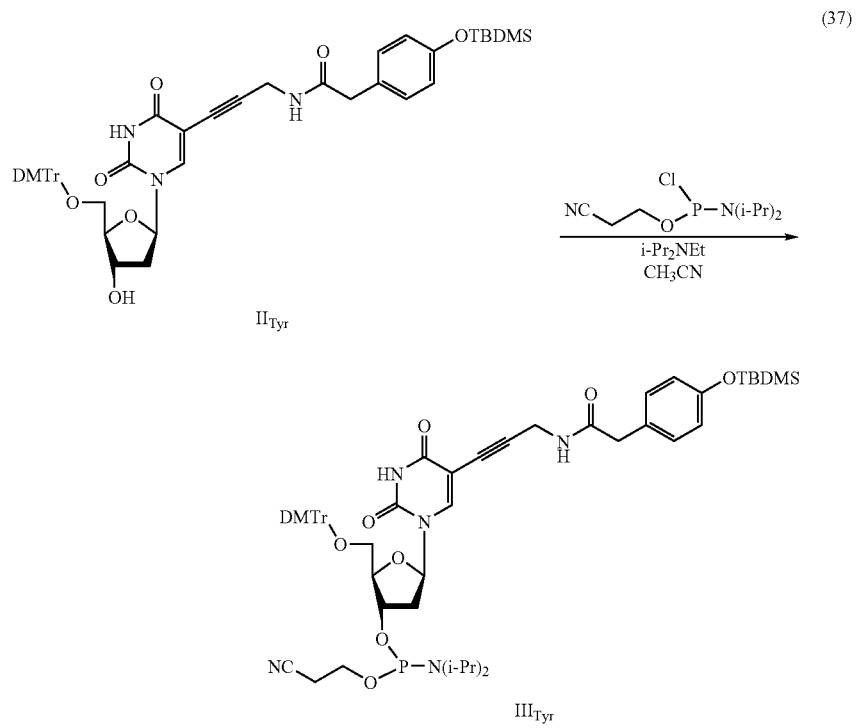

Example 13

Dimer: Synthesis of Substance $V_{Tyr}$base=G, Formula 38

(38)

Substance $II_{Tyr}$ (3.67 g, 4.41 mmol) and N-isobutylyl-3'-levuloylguanosine-5'-diisopropylaminocyanoethyl phosphoramidite (Substance IVbase=G, 3.36 g, 5.29 mmol) were measured in a 200 mL pear-shaped flask, azeotroped 3 times with dry acetonitrile, and dried with a vacuum pump. After dissolution in 25 mL of dry acetonitrile, 0.45 mol/L of tetrazole/acetonitrile solution (49 mL, tetrazole 22.1 mmol) was added and agitated for 30 minutes at room temperature. The reaction system was then neutralized by addition of a saturated aqueous sodium bicarbonate solution, and extracted 3 times with methylene chloride. The combined methylene chloride layer was washed with a saturated aqueous sodium chloride solution, dried with anhydrous sodium sulfate and concentrated.

The resulting residue was dissolved in 11.5 mL THF, and 0.12 mol/L of iodine/THF-pyridine-water (volume ratio 2:2:1, 11.5 mL, iodine 11.0 mmol) was added and agitated for 30 minutes at room temperature. The reaction system was diluted with methylene chloride, the excess iodine was reduced by addition of a 10% by weight aqueous sodium thiosulfate solution, and the water layer was extracted twice with methylene chloride. The combined methylene chloride layer was dried with anhydrous sodium sulfate, and purified by intermediate pressure chromatography (dichloromethane-ethanol, volume ratio changed gradually from 1:0 to 9:1) to obtain 5.62 g of the target product (yield 92%).

$^{1}$H-NMR (300 MHz, DMSO-d6) δ: 0.12 (6H, s), 0.89 (9H, s), 1.08 (6H, m), 2.06 (3H×1/2, s), 2.07 (3H×1/2, s), 2.47 (4H, m), 2.71 (2H, m), 2.75 (1H, m), 2.81 (2H, t, J=5.9 Hz), 2.81 (1H, m), 2.85 (1H, m), 3.08 (1H, m), 3.28 (1H, m), 3.31 (2H×1/2, s), 3.32 (2H×1/2, s), 3.68 (3H, s), 3.68 (3H, s), 3.89 (2H, d, J=4.8 Hz), 4.00-4.30 (6H, m), 5.00 (1H, m), 5.29 (1H, m), 6.08 (1H, m), 6.21 (1H, m), 6.71 (2H, d, J=8.2 Hz), 6.83 (2H, d, J=8.6 Hz), 6.83 (2H, d, J=8.6 Hz), 7.08 (2H, d, J=8.2 Hz), 7.15 (1H, m), 7.22 (4H, d, J=8.6 Hz), 7.22 (2H, m), 7.33 (2H, d, J=7.5 Hz), 7.89 (1/2H, s), 7.90 (1/2H, s), 8.17 (1/2H, s), 8.18 (1/2H, s), 8.41 (1H, t, J=4.8 Hz), 11.59 (1H, br·s), 11.69 (1H, br·s), 12.05 (1H, br·s)

$^{31}$P-NMR (BCM, 120 MHz, DMSO) δ: −2.19, −2.06

MALDI-TOF MS: Calculated value $(C_{69}H_{80}N_9NaO_{18}PSi^+)=1404.502$ $[M+Na]^+$, measured value=1404.632

Example 14

Dimer Levuloyl removal: Synthesis of Substance VI$_{Tyr}$base=G, Formula 39

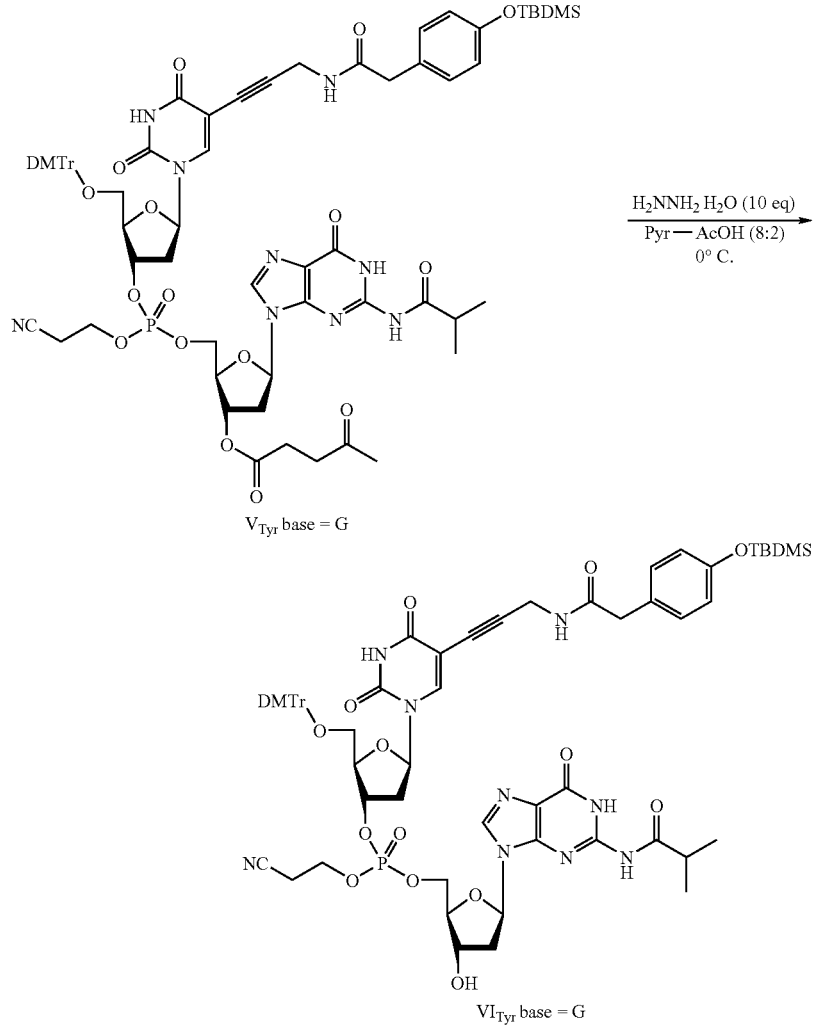

Substance VI$_{Tyr}$base=G (5.61 g, 4.06 mmol) was dissolved in 41 mL pyridine, and 41 mL of a mixed pyridine-acetic acid (volume ratio 3:2) solvent solution of hydrazine monohydrate (2.0 mL, 41.1 mmol) was added and agitated for 1 hour at 0° C. After addition of 4 mL acetone to convert the excess hydrazine to azone, this was diluted with methylene chloride and the excess acetic acid was neutralized with a saturated aqueous sodium bicarbonate solution. After three extractions with methylene chloride, the combined methylene chloride layer was washed with a saturated aqueous sodium chloride solution, dried with anhydrous sodium sulfate, and concentrated.

The resulting residue was purified by intermediate pressure chromatography (dichloromethane-ethanol, volume ratio changed gradually from 1:0 to 9:1) to obtain 4.65 g of the target product, VI$_{Tyr}$base=G (yield 90%).

$^{1}$H-NMR (300 MHz, DMSO) δ: 0.14 (6H, s), 0.92 (9H, s), 1.11 (6H, m), 2.33 (1H, m), 2.50 (2H, m), 2.61 (1H, m), 2.75 (1H, m), 2.84 (2H, m), 3.11 (1H, m), 3.29 (1H, m), 3.33 (2H, s), 3.70 (3H, s), 3.71 (3H, s), 3.92 (2H, br·d, J=5.1 Hz), 4.01 (1H, m), 4.11 (2H, m), 4.10-4.30 (3H, m), 4.40 (1H, m), 5.02 (1H, m), 5.53 (1H, d, J=3.9 Hz), 6.10 (1H, dd, J=6.4, 7.5 Hz), 6.23 (1H, m), 6.73 (2H, d, J=8.4 Hz), 6.86 (4H, br·d, J=7.5 Hz), 7.10 (2H, d, J=8.4 Hz), 7.15-7.30 (7H, m), 7.35 (2H, d, J=7.3 Hz), 7.91 (1/2H, s), 7.92-7.91 (1/2H, s), 8.14 (1/2H, s), 8.16 (1/2H, s), 8.44 (1H, br·t, J=5.1 Hz), 11.60 (1H, br), 11.72 (1H, br)

$^{31}$P-NMR (BCM, 120 MHz, DMSO) δ: −2.09, −1.94

MALDI-TOF MS: Calculated value (C$_{64}$H$_{74}$N$_{9}$NaO$_{16}$PSi$^{+}$)=1306.4653 [M+H], measured value=1306.375 [M+H]

Example 15

Dimer Amidite: Synthesis of Substance VII$_{Tyr}$base=G, Formula 40

Substance VI$_{Tyr}$base=G (1.44 g, 1.12 mmol) was azeotropically dehydrated 3 times with dry acetonitrile, and thoroughly dried with a vacuum pump. Following addition of 11 mL acetonitrile and 252 μL diisopropylethylamine (1.46 mmol), this was cooled to 0° C., and agitated for 1 hour at 0° C. after addition of diisopropylchlorophosphoramidite (300 μL, 1.35 mmol).

After the excess amidite-forming reagent had been inactivated by addition of 1.0 mL methanol, this was partitioned between water and methylene chloride, and the organic layer was concentrated and purified by intermediate pressure chromatography (2% by volume Et$_{3}$N-containing dichloromethane:ethanol, volume ratio changed gradually from 1:0 to 9:1) to obtain 0.99 g of the target product, VII$_{Tyr}$base=G (yield 60%).

$^{1}$H-NMR (300 MHz, DMSO-d6) δ: 0.14 (6H, s), 0.92 (9H, s), 1.14 (18H, m), 2.5 (3H, m), 3.11 (1H, m), 3.3 (1H, m), 3.58 (2H, m), 3.70 (3H, s), 3.71 (3H, s), 3.72 (2H, m), 3.91 (2H, br·d, J=4.8 Hz), 4.0-4.3 (6H, m), 4.61 (1H, m), 5.01 (1H, m), 6.10 (1H, m), 6.25 (1H, m), 6.73 (2H, d, J=8.3 Hz), 6.85 (2H, d, J=8.5 Hz), 6.86 (2H, d, J=8.5 Hz), 7.09 (2H, d, J=8.3 Hz),

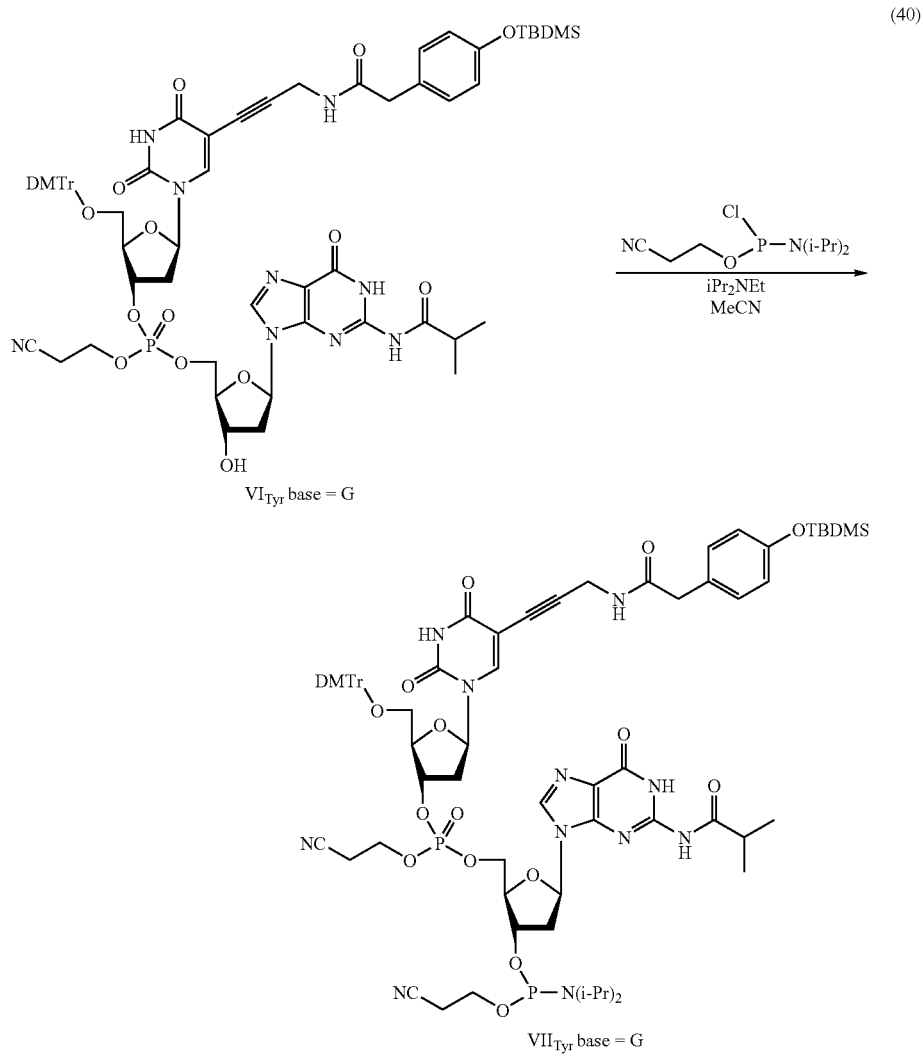

7.33 (2H, t, J=7.8 Hz), 7.15-7.3 (7H, m), 7.91 (1H, s), 8.17 (1H, s), 8.43 (1H, br), 11.55 (1H×1/2, s), 11.57 (1H×1/2, s), 11.71 (1H, s), 12.07 (1H s)

$^{31}$P-NMR (120 MHz, DMSO-d6) δ: −2.01, −1.89, 148.42, 148.70

MALDI-TOF MS: Calculated value $(C_{73}H_{91}N_{11}NaO_{17}P_2Si^+)$-1506.5731 [M+H]$^+$, measured value=1506.317 [M+H]$^+$ Example 16

Monomer: Synthesis of Substance II$_{Ser}$, Formula 41

(41)

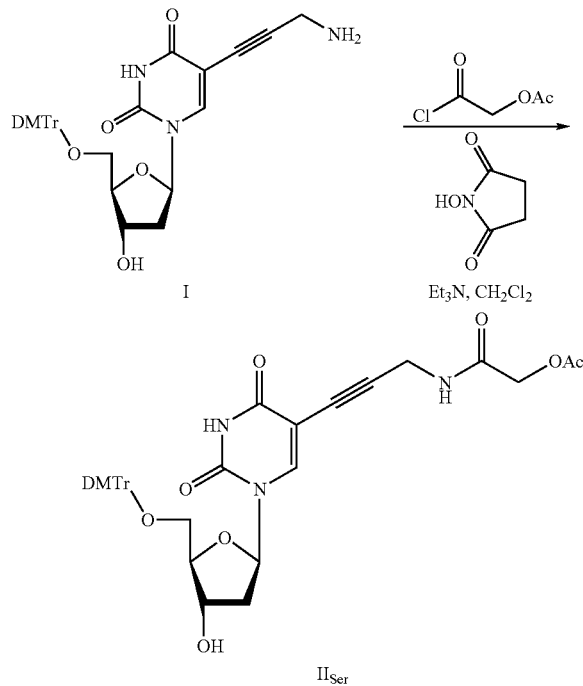

1.27 g (12.5 mmol) of N-hydroxysuccinic acid imide was dissolved in 30 mL dichloromethane, and agitated at room temperature. A dichloromethane solution (10 mL) of acetoxyacetylchloride (1.08 mL, 10.0 mmol) was added. Next a dichloromethane solution (10 mL) of triethylamine (1.66 mL, 12.0 mmol) was added and agitation was continued for about 40 minutes. A dichloromethane solution (10 mL) of substance I (5.68 g, 10.0 mmol) was added, followed by about 2 hours of agitation. After completion of the reaction had been confirmed by TLC, water was added and the mixture was extracted as it was with dichloromethane. Sodium chloride was added to salt out the organic layer, which was then dried with anhydrous sodium sulfate. After filtration of the drying agent, this was concentrated under reduced pressure. Purification by intermediate pressure column chromatography (dichloromethane-ethyl acetate, volume ratio changed gradually from 1:0 to 0:1) yielded 5.99 g of the target amide product (yield 88%).

$^1$H-NMR (300 MHz, DMSO-d6) δ: 2.07 (3H, s), 2.16 (1H, m), 2.26 (1H, m), 3.06 (1H, dd, J=2.6, 10.3 Hz), 3.25 (1H, dd, J=5.2, 10.3 Hz), 3.73 (6H, s), 3.91 (1H, m), 3.93 (2H, d, J=5.3 Hz), 4.25 (1H, m), 4.44 (2H, s), 5.32 (1H, d, J=4.4 Hz), 6.08 (1H, dd, J=6.6, 6.8 Hz), 6.88 (2H, d, J=8.8 Hz, DMTr), 6.89 (2H, d, J=8.8 Hz), 7.20-7.35 (7H, m), 7.39 (2H, d, J=7.3 Hz), 7.90 (1H, s), 8.47 (1H, t, J=5.3 Hz), 11.67 (1H, s)

MALDI-TOF MS: Calculated value $(C_{37}H_{38}N_3O_{10}+)$=684.2552 [M+H]$^+$, measured value=683.960 [M+H]$^+$ Example 17

Amidite: Synthesis of Substance III$_{Ser}$, Formula 42

(42)

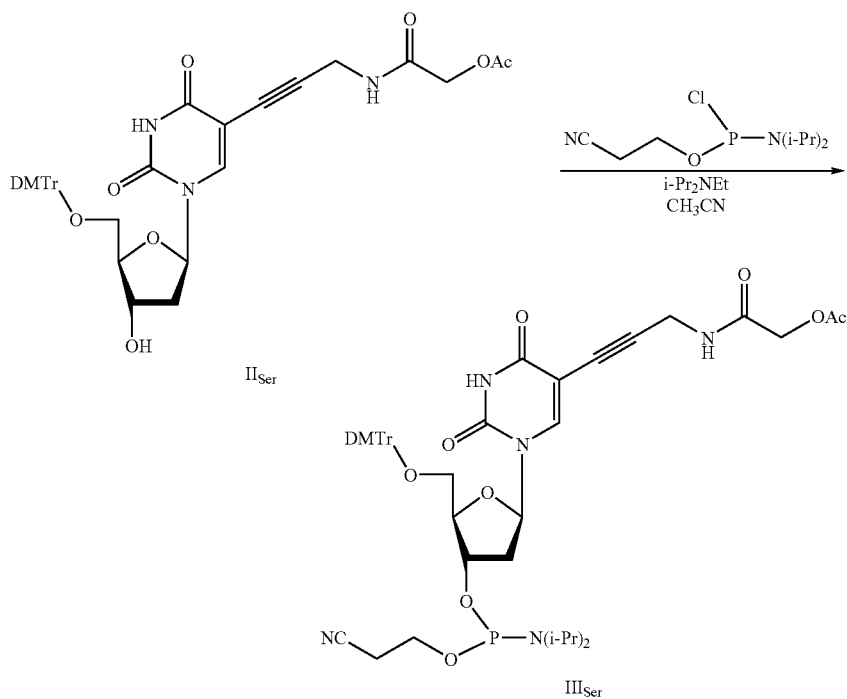

Substance II$_{Ser}$ (342 mg, 0.50 mmol) was azeotropically dehydrated 3 times with 5 mL dry acetonitrile and dried. This was dissolved in 10 mL dry acetonitrile, and after addition of 104 μL (0.60 mmol) diisopropylethylamine, diisopropylchlorophosphoramidite (122 μL, 0.55 mmol) was added under ice cooling. After 2 hours of agitation followed by addition of methanol to inactivate the excess amidite-forming reagent, this was diluted with methylene chloride, and washed with a saturated aqueous sodium bicarbonate solution and a saturated aqueous sodium chloride solution. Purification by intermediate pressure chromatography (2% by volume Et$_3$N-containing dichloromethane:hexane, volume ratio gradually changed from 1:1 to 1:0, followed by 2% by volume Et$_3$N-containing dichloromethane:ethanol, volume ratio gradually changed from 1:0 to 19:1) yielded 367 mg of Substance III$_{Ser}$ (yield 87%).

$^1$H-NMR (300 MHz, DMSO-d6) δ: 0.98 (3H, d, J=6.6 Hz), 1.10 (6H, d, J=6.6 Hz), 1.12 (3H, d, J=6.6 Hz), 2.07 (3H, s), 2.30 (1H, m), 2.43 (1H, m), 2.64 (2H×1/2, t, J=5.9 Hz), 2.74 (2H×1/2, t, J=5.9 Hz), 3.16 (1H, m), 3.28 (1H, m), 3.50 (2H, m), 3.65 (2H, m), 3.95 (2H×1/2, d, J=5.5 Hz), 3.98 (2H×1/2, d, J=5.5 Hz), 4.06 (1H, m), 4.44 (2H, s), 4.48 (1H, m), 6.07 (1/2H, dd, J=6.6, 7.0 Hz), 6.09 (1/2H, dd, J=6.6, 6.8 Hz), 6.87 (2H, d, J=7.9 Hz), 6.88 (2H, d, J=8.4 Hz), 7.20-7.35 (7H, m), 7.39 (2H, d, J=7.2 Hz), 7.94 (1H, s), 8.43 (1/2H, t, J=5.5 Hz), 8.45 (1/2H, t, J=5.5 Hz), 11.64 (1H, s)

$^{31}$P-NMR (BCM, 120 MHz, DMSO) δ: 147.62, 148.02

MALDI-TOF MS: Calculated value (C$_{46}$H$_{54}$N$_5$NaO$_{11}$P$^+$)=906.345 [M+Na]$^+$, measured value 905.857 [M+Na]+

Example 18

Levuloyl Group Introduction and DMTr Removal: Synthesis of Substance IX$_{xer}$, Formula 43

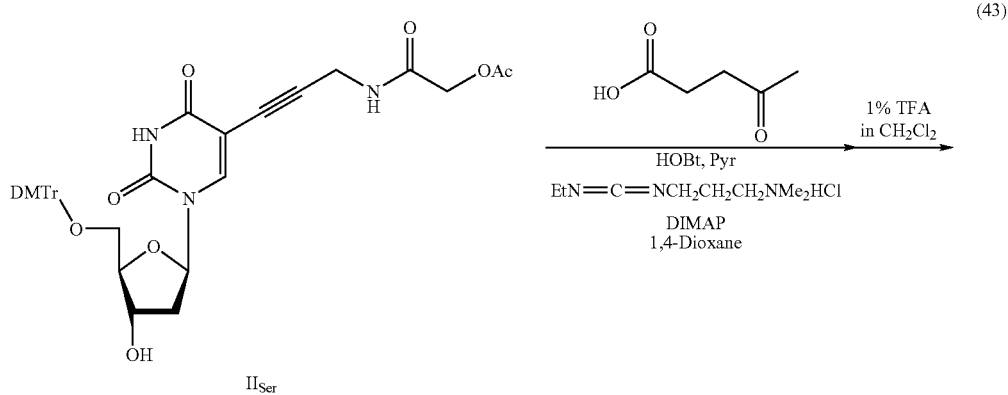

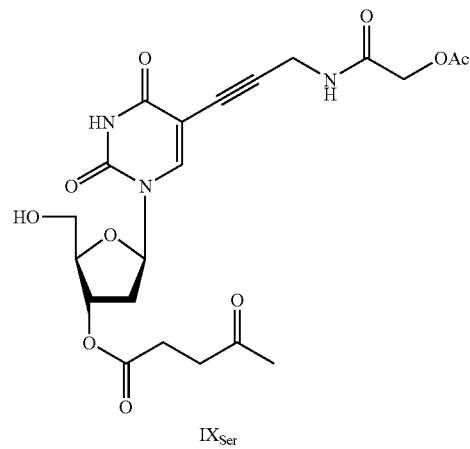

Substance II$_{Ser}$ (1.96 g, 2.87 mmol) was dissolved in 23 mL of 1,4-dioxane, and pyridine (0.58 mL), N-ethyl-N'-(dimethylaminopropyl)carbodiimide hydrochloride (1.38 g, 7.22 mmol), 4-dimethylaminopyridine (0.030 g, 0.25 mmol) and levulinic acid (0.60 mL, 5.84 mmol) were added successively at room temperature. After agitation for 5 hours and 20 minutes at room temperature, this was partitioned between methylene chloride and a saturated aqueous sodium bicarbonate solution, and then extracted twice with methylene chloride. The combined methylene chloride layer was washed with a saturated aqueous sodium chloride solution, dried with anhydrous sodium sulfate, and concentrated.

The concentrated residue was dissolved in 41 mL of methylene chloride, ice cooled, and agitated for 1 hour at 0° C. after addition of trifluoracetic acid (410 µL). After neutralization of most of the trifluoracetic acid by addition of a sodium bicarbonate powder, this was filtered and concentrated. Purification of the concentrated residue by intermediate pressure chromatography (dichloromethane-ethanol, volume ratio changed gradually from 1:0 to 9:1) yielded 1.16 g of the target product, IX$_{Ser}$ (yield 84%).

$^1$H-NMR (300 MHz, DMSO-d6) δ: 2.08 (3H, s), 2.11 (3H, s), 2.27 (2H, m), 2.49 (2H, t, J=6.3 Hz), 2.76 (2H, t, J=6.3 Hz), 3.62 (2H, m), 3.99 (1H, m), 4.11 (2H, d, J=5.4 Hz), 4.40 (2H, s), 5.19 (1H, m), 5.28 (1H, t, J=4.9 Hz), 6.13 (1H, dd, J=6.8, 7.5 Hz), 8.17 (1H, s), 8.58 (1H, t, J=5.4 Hz), 11.69 (1H, s)

MALDI-TOF MS: Calculated value $(C_{21}H_{26}N_3O_{10}^+)$= 480.1613 [M+H] H$^+$, measured value=480.234

Example 19

Dimer: Synthesis of Substance X$_{Ser}$base=T, Formula 44

(44)

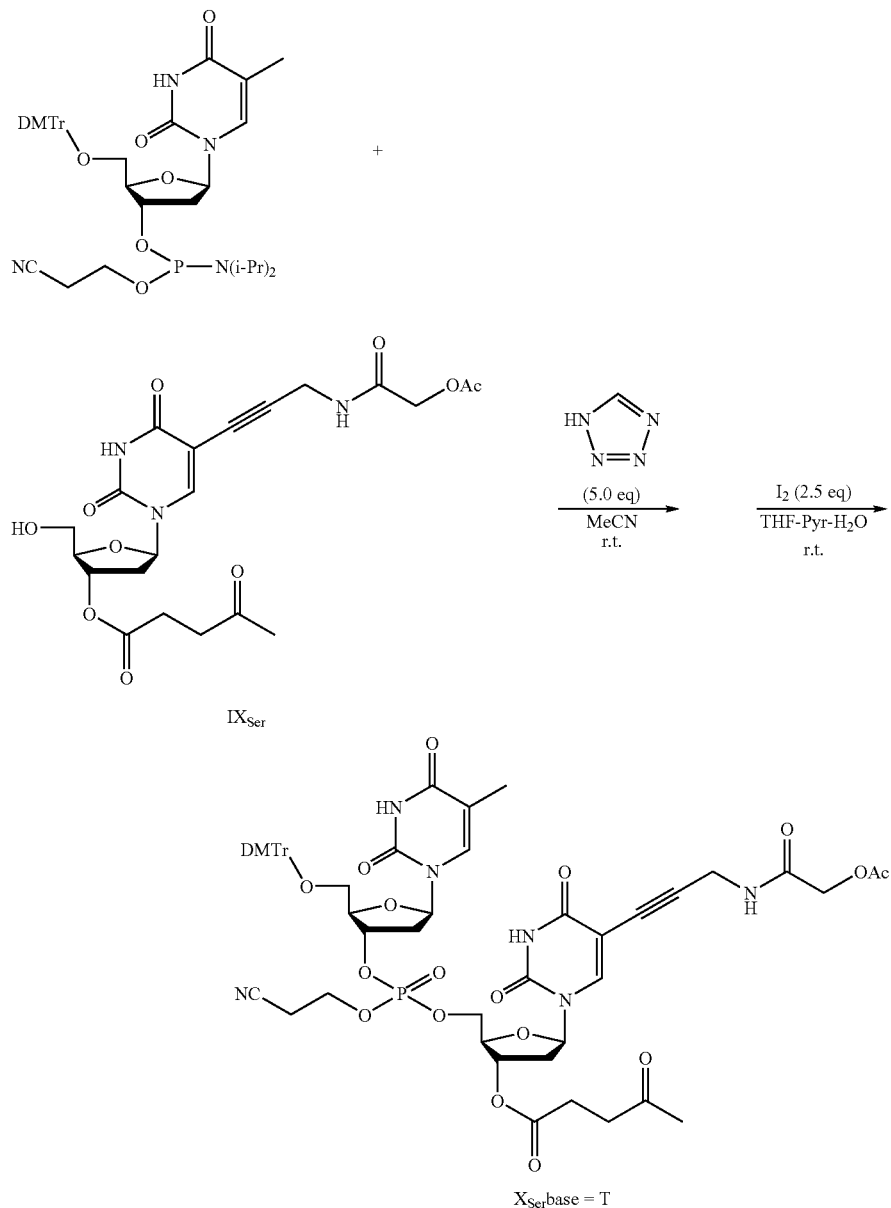

IX$_{Ser}$

X$_{Ser}$base = T

Substance IX$_{Ser}$ (1.09 g, 2.28 mmol) was azeotropically dehydrated three times with dry acetonitrile, and dried with a vacuum pump. 5'-(4,4'-dimethoxytriphenylmethyl)-thymidine-3'-(diisopropylamino)cyanoethylphosphoramidite (1.70 g, 2.29 mmol) was added, followed by 12 mL of dry acetonitrile and 0.45 mol/L of tetrazole/acetonitrile solution (25 mL, tetrazole 11.4 mmol), and the mixture was agitated for 45 minutes at room temperature. This was partitioned by addition of methylene chloride and a saturated aqueous sodium bicarbonate solution, the water layer was extracted twice with methylene chloride, and the combined methylene chloride layer was washed with a saturated aqueous sodium chloride solution, dried with anhydrous sodium sulfate, and concentrated.

The concentrated residue was dissolved in a mixed solution of 34 mL THF, 9.5 mL pyridine and 4.7 mL water, and 1.45 g (5.70 mmol) of iodine was added and agitated for 30 minutes at room temperature. After dilution with methylene chloride, 3.6 g of sodium sulfite was added and agitated for 15 minutes at room temperature. After removal of water with anhydrous sodium sulfate, this was concentrated. The concentrated residue was diluted with methylene chloride and washed in water. The water layer was extracted twice with methylene chloride, and the combined methylene chloride layer was washed with a saturated aqueous sodium chloride solution, dried with anhydrous sodium sulfate, and concentrated.

The concentrated residue was purified by intermediate pressure chromatography (dichloromethane-ethanol, volume ratio raised gradually from 1:0 to 93:7) to obtain 2.00 g of the target product, X$_{Ser}$base=T (yield 77%).

$^1$H-NMR (300 MHz, DMSO-d6) δ: 1.42 (3H, d, J=2.0 Hz), 2.06 (3H×1/2, s), 2.06 (3H, s), 2.07 (3H×1/2, s), 2.23 (1H, dd, J=6.4, 13.6 Hz), 2.43 (5H, m), 2.70 (2H, m), 2.87 (2H×1/2, t, J=5.6 Hz), 2.89 (2H×1/2, t, J=5.6 Hz), 3.21 (1H, m), 3.30 (1H, m), 3.72 (6H, s), 4.05-4.30 (8H, m), 4.44 (2H×1/2, s), 4.45 (2H×1/2, s), 5.11 (2H, m), 6.06 (1H×1/2, dd, J=6.1, 6.1 Hz), 6.09 (1H×1/2, dd, J=6.1, 6.1 Hz), 6.21 (1H, dd, J=7.0, 7.2 Hz), 6.88 (4H, d, J=8.6 Hz), 7.23 (4H, d, J=8.6 Hz), 7.20-7.40 (5H, m), 7.48 (1H, br·s), 7.95 (1H, br), 8.53 (1H, t, J=5.4 Hz), 11.39 (1H, br), 11.71, (1H, br)

$^{31}$P-NMR (BCM, 120 MHz, DMSO-d6) δ: −2.19, −2.11

MALDI-TOF MS: Calculated value (C$_{55}$H$_{59}$N$_6$NaO$_{19}$P$^+$)=1161.346 [M+Na], measured value=1161.259 [M+Na]

Example 20

Dimer Levuloyl Removal: Synthesis of Substance XI$_{Ser}$base=T, Formula 45

(45)

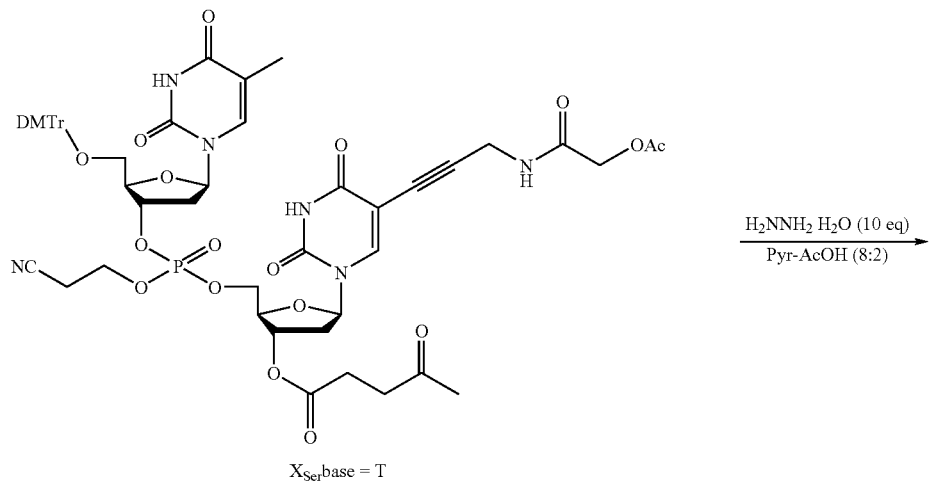

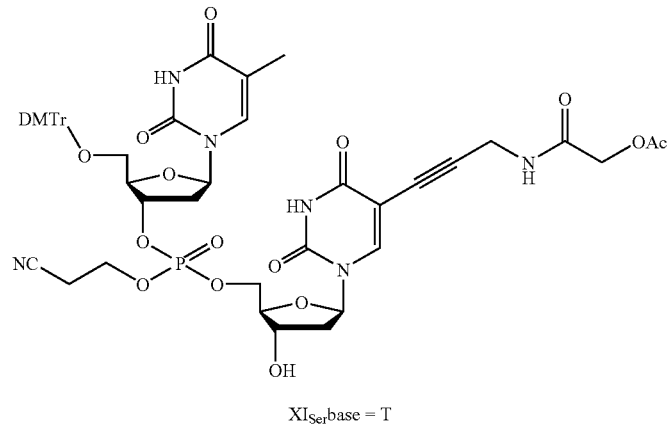

Substance X$_{Ser}$base=T (1.92 g, 1.69 mmol) was dissolved in 23 mL of pyridine, and hydrazine monohydrate (0.78 mL, 16.0 mmol) and a mixed pyridine-acetic acid solvent (volume ratio 3:2, 23 mL) were added and agitated for 5 minutes at room temperature. 17 mL of acetone was added under ice cooling. The reaction liquid was diluted with methylene chloride, followed by partitioning, and the water layer was further extracted twice with methylene chloride. The combined methylene chloride layer was washed with a saturated aqueous sodium chloride solution, dried with anhydrous sodium sulfate, and concentrated.

The concentrated residue was purified by intermediate pressure chromatography (dichloromethane-ethanol, volume ratio raised gradually from 1:0 to 93:7) to obtain 1.50 g of the target product, XI$_{Ser}$base=T (yield 86%).

$^1$H-NMR (300 MHz, DMSO-d6) δ: 1.44 (3H, d, J=3.3 Hz), 2.06 (3H, s), 2.09 (1H, m), 2.20 (1H, m), 2.50 (2H, m), 2.87 (2H×1/2, t, J=6.5 Hz), 2.89 (2H×1/2, t, J=6.5 Hz), 3.3 (2H, m), 3.73 (6H, s), 3.90 (1H, m), 4.08 (2H, m), 4.10-4.25 (5H, m), 4.44 (2H, s), 5.08 (1H, m), 5.42 (1H, d, J=4.2 Hz), 6.08 (1H, m), 6.21 (1H, dd, J=7.2, 7.3 Hz), 6.88 (4H, d, J=8.8 Hz), 7.24 (4H, d, J=8.8 Hz), 7.22-7.40 (5H, m), 7.47 (1H, br·s), 7.86 (1/2H, s), 7.87 (1/2H, s), 8.48 (1H, br), 11.34 (1H, br), 11.62 (1H, br)

$^{31}$P-NMR (BCM, 120 MHz, DMSO-d6) δ: −1.99, −1.89

MALDI-TOF MS: Calculated value (C$_{50}$H$_{53}$N$_6$NaO$_{17}$ P$^+$)=1063.310 [M+Na], measured value=1063.288 [M+Na]

Example 21

Dimer Amidite: Synthesis of Substance XII$_{Ser}$base=T, Formula 46

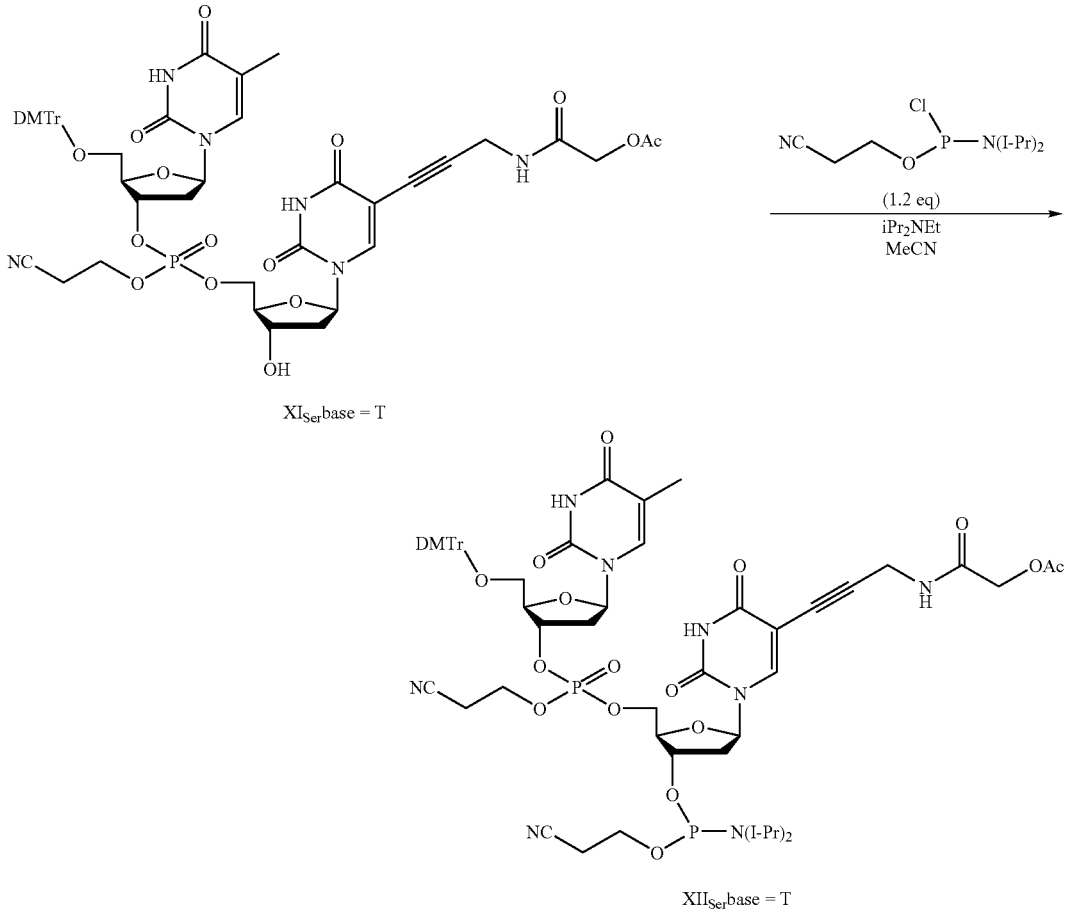

XII$_{Ser}$base = T

Substance XI$_{Ser}$base=T (1.23 mg, 1.18 mmol) was azeotropically dehydrated 3 times with dry acetonitrile, and thoroughly dried with a vacuum pump. 12 mL acetonitrile and 4 mL methylene chloride were added, and after addition of diisopropylethylamine (268 μL, 1.54 mmol) and cooling to −20° C., diisopropylchlorophosphoramidite (0.32 mL, 1.44 mmol) was added to the mixture, which was then agitated for 1 hour at room temperature.

After inactivation of the excess amidite-forming reagent by addition of 1.2 mL methanol, the concentrated residue was purified by intermediate pressure chromatography (2% by volume Et$_3$N-containing dichloromethane:ethanol, volume ratio raised gradually from 1:0 to 9:1) to obtain 1.21 g of the target product, XII$_{Ser}$base=T (yield 82%).

$^1$H-NMR (300 MHz, DMSO-d6) δ: 1.12 (12H, m), 1.41 (3H, br·s), 2.06 (3H×1/2, s), 2.06 (3H×1/2, s), 2.25 (1H, m), 2.38 (1H, m), 2.75 (2H, m), 2.85 (2H, m), 3.21 (1H, br·d, J=12 Hz), 3.30 (1H, br·d, J=12 Hz), 3.56 (2H, m), 3.72 (6H, s), 3.72 (2H, m), 4.00-4.35 (8H, m), 4.44 (2H, s), 4.44 (1H, m), 5.08

(1H, m), 6.07 (1H, m), 6.22 (1H, dd, J=7.0, 7.0 Hz), 11.40 (1H, s), 11.68 (1H, br·s)

$^{31}$P-NMR (120 MHz, DMSO-d6) δ: −2.19, 148.47

MALDI-TOF MS: Calculated value $(C_{59}H_{70}N_8NaO_8P_2^+)$=1263.4176 [M+Na], measured value=1263.293

Example 22

Synthesis of Substance at Right of Formula 47

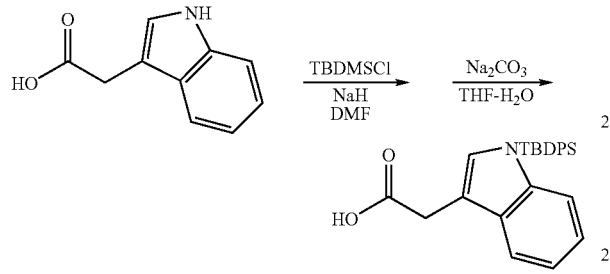

(47)

Sodium hydride (60% by weight in mineral oil, 1.52 g, 38.1 mmol) was suspended in DMF (21 mL), and a DMF solution (7 mL) of 3-indolacetic acid (2.11 g, 12.1 mmol) was dripped in at room temperature over the course of 10 minutes. 10 minutes after dripping, TBDPSCl (10 g, 36.4 mmol) was dripped in at room temperature over the course of 20 minutes. After agitation at room temperature for 1 hour, 15 minutes, water was dripped in to react the excess sodium hydride, followed by partitioning between water and ethyl acetate, and the water layer was further extracted twice with ethyl acetate. The combined ethyl acetate layer was washed with a saturated aqueous sodium chloride solution, dried with anhydrous sodium sulfate, and concentrated.

The concentrated residue was emulsified in a mixed solvent of 100 mL THF and 40 mL water, and solid sodium carbonate (12.8 g, 0.120 mmol) was added at room temperature. After 5 hours of agitation at room temperature, solid ammonium chloride was added. After the partitioning between water and ethyl acetate, the water layer was further extracted twice with ethyl acetate. The combined ethyl acetate layer was washed with a saturated aqueous sodium chloride solution, dried with anhydrous sodium sulfate, and concentrated.

The concentrated residue was suspended by addition of methanol and filtered after precipitation of silanol, and the filtrate was concentrated. The concentrated residue was purified by intermediate pressure chromatography (dichloromethane-ethanol, volume ratio gradually changed from 1:0 to 9:1) to obtain 3.46 g of the target product (yield 69%).

$^1$H-NMR (CDCl$_3$) δ: 1.15 (9H, s), 3.76 (2H, s), 6.67 (2H, dd, J=0.9, 8.4 Hz), 6.78 (1H, ddd, J=1.1, 7.2, 8.4 Hz), 7.00 (1H, ddd, J=0.9, 7.0, 7.2 Hz), 7.18 (1H, s), 7.2-7.4 (6H, m), 7.5-7.6 (5H, m)

Example 23

Monomer: Synthesis of Substance II$_{Typ}$, Formula 48

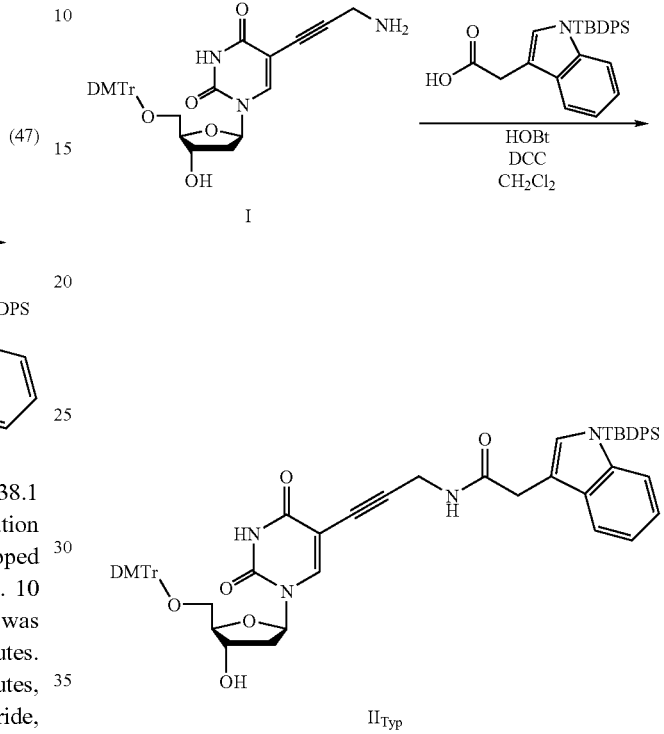

(48)

HOBT monohydrate (0.666 g, 4.35 mmol) and N-(t-butyl-diphenylsilyl)indolacetic acid (1.78 g, 4.31 mmol) were suspended in 33 mL of methylene chloride, and DCC (0.910 g, 4.41 mmol) was added. After 30 minutes of agitation at room temperature 10 mL of a methylene chloride solution of Substance I (3.14 g, purity 80% by weight, 4.31 mmol) was dripped in over the course of 15 minutes. After 70 minutes of agitation at room temperature this was filtered, and the filtrate was concentrated. Ethyl acetate was added to the concentrated residue, and after precipitation of the insoluble matter this was filtered and the filtrate was concentrated and purified by intermediate pressure chromatography (dichloromethane-ethanol, volume ratio changed gradually from 1:0 to 9:1). 3.05 g (yield 72%) of the target product, II$_{Typ}$ was obtained.

$^1$H-NMR (DMSO-d6) δ: 1.14 (9H, s), 2.22 (2H, m), 3.08 (1H, br·d, J=9.3 Hz), 3.27 (1H, m), 3.61 (2H, s), 3.70 (6H, s), 3.94 (3H, m), 4.26 (1H, m), 5.29 (1H, d, J=4.2 Hz), 6.09 (1H, dd, J=6.5, 6.5 Hz), 6.51 (1H, d, J=8.4 Hz), 6.74 (1H, dd, J=7.2, 8.1 Hz), 6.9 (4H, m), 6.94 (1H, m), 7.18 (1H, m), 7.22-7.6 (20H, m), 7.89 (1H, s), 8.43 (1H, t, J=4.9 Hz), 11.63 (1H, s)

MALDI-TOF MS: Calculated value $(C_{59}H_{58}N_4O_8Si)$= 978.410 [M]$^+$, measured value=979.919 [M+H]$^+$

Example 24

Amidite: Synthesis of Substance III$_{Typ}$, Formula 49

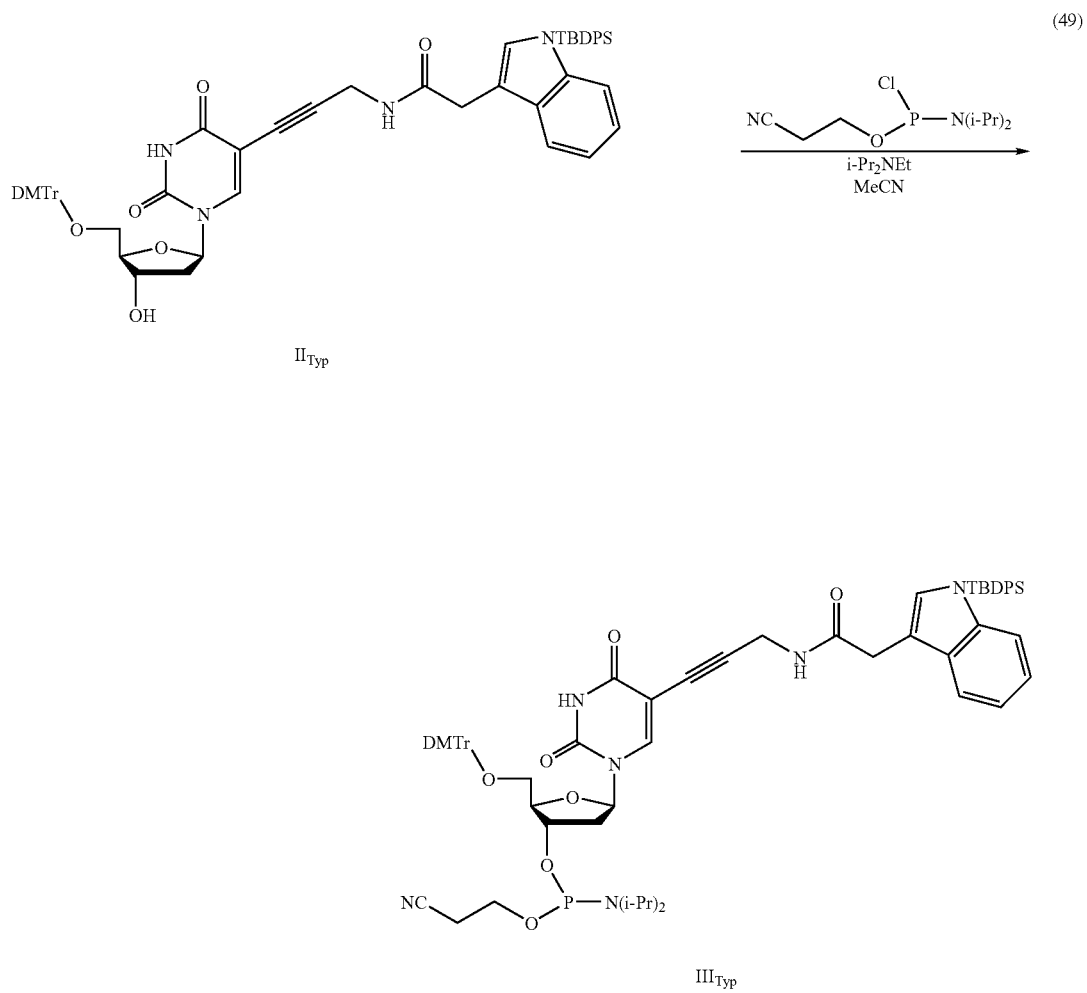

Substance II$_{Typ}$ (0.378 g, 0.386 mmol) was azeotropically dehydrated 3 times with 1 mL dry acetonitrile, and dried. This was dissolved in 1.0 mL dry acetonitrile, diisopropylethylamine (100 μL, 0.450 mmol) was added, the mixture was cooled to 0° C. and a dry acetonitrile solution (0.5 mL) of diisopropylchlorophosphoramidite (0.102 g, 0.432 mmol) was dripped in. After 1 hour of agitation and addition of methanol to inactivate the excess amidite-forming reagent, this was diluted with methylene chloride, and washed with a saturated aqueous sodium bicarbonate solution and a saturated aqueous sodium chloride solution. Purification by intermediate pressure chromatography (2% by volume Et$_3$N-containing dichloromethane:hexane, volume ratio changed gradually from 1:1 to 1:0 followed by 2% by volume Et$_3$N-containing dichloromethane:ethanol, volume ratio changed gradually from 1:0 to 19:1) yielded 0.341 g of the target product, III$_{Typ}$ (yield 75%).

$^1$H-NMR (DMSO-d6) δ: 0.98 (3H, d, J=6.8 Hz), 1.10 (6H, m), 1.14 (9H, s), 2.30 (1H, m), 2.41 (1H, m), 2.63 (1H, t, J=5.9 Hz), 2.74 (1H, t, J=5.9 Hz), 3.14 (1H, m), 3.3 (1H, m), 3.52 (2H, m), 3.60 (2H, s), 3.70 (6H, s), 3.65 (2H, m), 3.73 (2H, m), 3.96 (2H, m), 4.03 (1H, m), 4.46 (1H, m), 6.07 (1/2H, dd, J=6.6, 6.8 Hz), 6.09 (1/2H, dd, J=6.6, 6.8 Hz), 6.50 (1H, d, J=8.4 Hz), 6.74 (1H, m, dd, J=6.8, 7.2 Hz), 6.86 (2H, d, J=6.2 Hz), 6.87 (2H, d, J=6.2 Hz), 6.94 (1H, dd, J=7.5, 7.7 Hz), 7.1-7.6 (20H, m), 7.93 (1H, s), 8.44 (1H, m), 11.63 (1H, s)

$^{31}$P-NMR (BCM, DMSO-d6) δ: 147.97, 147.60

MALDI-TOF MS: Calculated value (C$_{68}$H$_{76}$N$_6$O$_9$PSi$^+$)= 1179.520 [M+H], measured value=1178.937 [M+H]

Example 25

Dimer: Synthesis of Substance $V_{Typ}$base=C, Formula 50

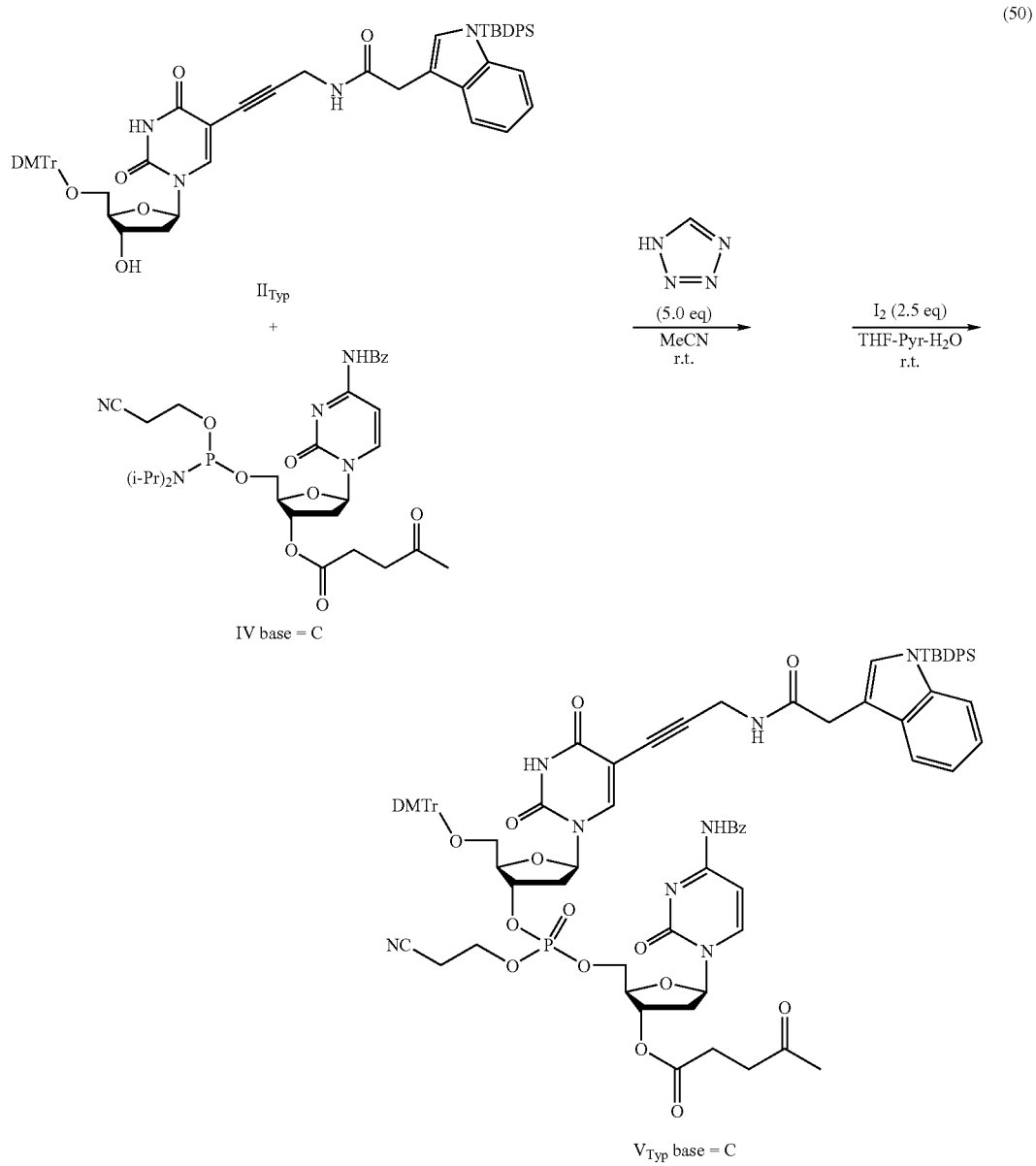

(50)

0.914 g (0.934 mmol) of Substance $II_{Typ}$ and 3'-levuloyl-4-benzoylcytidine-5'-(diisopropylamino) cyanoethylphosphoramidite (Substance IVbase=C, 0.709 g, 1.13 mmol) were measured in a 200 mL pear-shaped flask, azeotropically dehydrated three times with dry acetonitrile, and dried with a vacuum pump. After addition of 10 mL of dry acetonitrile, 0.45 mol/L of tetrazole/acetonitrile solution (10.4 mL, tetrazole 4.68 mmol) was added and agitated for 30 minutes at room temperature. After being neutralized with a saturated aqueous sodium bicarbonate solution, this was extracted three times with methylene chloride, and the combined methylene chloride layer was washed with a saturated aqueous sodium chloride solution, dried with anhydrous sodium sulfate and concentrated.

The concentrated residue was dissolved in 7 mL THF, and 0.12 mol/L iodine/THF-pyridine-water (volume ratio 2:2:1, 13 mL, iodine 2.36 mmol) was added and agitated for 30 minutes at room temperature. After dilution of the reaction system with methylene chloride, the excess iodine was reduced with a 10% by weight aqueous sodium thiosulfate solution, and the water layer was extracted three times with methylene-chloride. The combined methylene chloride layer was washed with a saturated aqueous sodium chloride solution, dried with anhydrous sodium sulfate, and concentrated.

The concentrated layer was purified by intermediate pressure chromatography (dichloromethane-ethanol, volume ratio changed gradually from 1:0 to 9:1) to obtain 1.35 g of the target product, $V_{Typ}$base=C (yield 95%).

$^1$H-NMR (DMSO-d6) δ: 1.13 (9H, s), 2.08 (3H×1/2, s), 2.09 (3H×1/2, s), 2.35 (1H, m), 2.5 (5H, m), 2.72 (2H, m), 2.88 (2H, m), 3.14 (1H, m), 3.32 (1H, m), 3.61 (2H, s), 3.68 (6H, s), 3.95 (2H, br·s), 4.1-4.4 (6H, m), 5.04 (1H, m), 6.13 (2H, m), 6.49 (1H, d, J=8.4 Hz), 6.73 (1H, dd, J=7.3, 7.9 Hz), 6.86 (4H, m), 6.94 (1H, dd, J=7.3, 7.7 Hz), 7.1-7.7 (24H, m), 7.93 (1H, s), 7.98 (2H, d, J=7.3 Hz), 8.14 (1H, m), 8.5 (1H, br·s), 11.29 (1H, br·s), 11.72 (1H, br·s)

$^{31}$P-NMR (120 MHz, DMSO-d6, BCM) δ: −2.11, −1.99

MALDI-TOF MS: Calculated value $(C_{83}H_{83}N_8NaO_{17}PSi^+)$=1545.528 [M+Na], measured value=1545.468 [M+Na]

Example 26

Dimer Levuloyl Removal: Synthesis of Substance $VI_{Typ}$base=C, Formula 51

Substance $V_{Typ}$base=C (1.20 g, 0.789 mmol) was dissolved in 7.9 mL pyridine and cooled to 0° C. 7.9 mL of a mixed pyridine-acetic acid (volume ratio 3:2) solvent solution of 385 μL of hydrazine monohydrate was added and agitated for 20 minutes at 0° C. After addition of acetone to convert excess hydrazine to azone, this was diluted with methylene chloride, and partitioned by addition of a saturated aqueous sodium bicarbonate solution. The water layer was further extracted twice with methylene chloride, and the combined methylene chloride layer was washed with a saturated aqueous sodium chloride solution, dried with anhydrous sodium sulfate, and concentrated.

The concentrated residue was purified by intermediate pressure chromatography to obtain 1.17 g of the target product, $VI_{Typ}$base=C with a yield of 84%.

$^1$H-NMR (DMSO-d6) δ: 1.13 (9H, s), 2.12 (1H, m), 2.61 (1H, m), 6.24 (1H, m), 2.88 (1/2×2H, t, J=6.1 Hz), 2.90 (1/2×2H, t, J=6.1 Hz), 3.15 (1H, m), 3.34 (1H, m), 3.61 (2H, s), 3.68 (6H, s), 3.96 (2H, br·s), 4.03 (1H, m), 4.1-4.3 (6H, m), 5.04 (1H, m), 5.51 (1H, d, J=4.2 Hz), 6.13 (2H, m), 6.50 (1H, d, J=8.3 Hz), 6.73 (1H, dd, J=7.3, 7.8 Hz), 6.85 (4H, d, J=7.9 Hz), 6.94 (1H, dd, J=7.3 Hz, 7.7 Hz), 7.1-7.7 (25H, m), 7.93

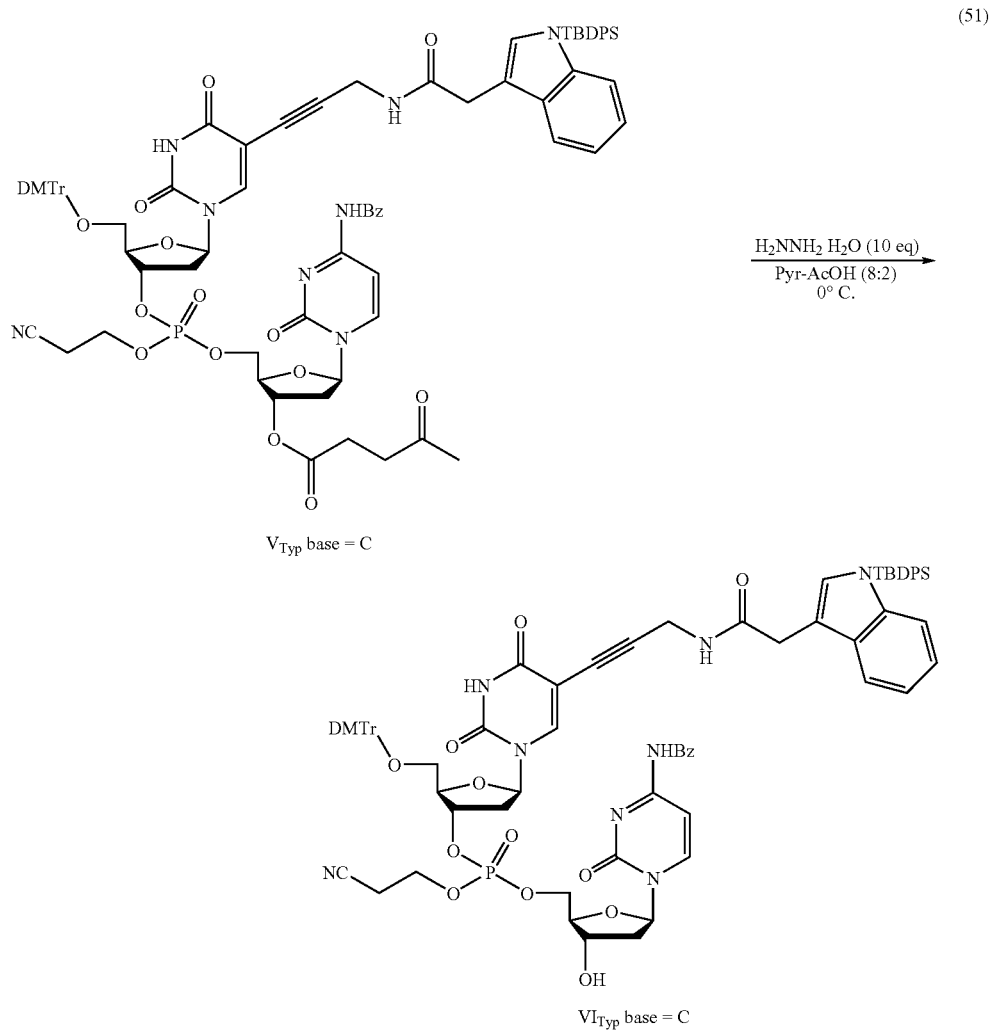

(51)

(1H, s), 7.99 (2H, d=7.3 Hz), 8.12 (1H, br·s), 8.50 (1H, br·s), 11.25 (1H, br·s), 11.71 (1H, br·s)

$^{31}$P-NMR (BCM, DMSO-d6) δ: −1.84, −2.04

MALDI-TOF MS: Calculated value $(C_{78}H_{77}N_8NaO_{15}PSi^+)$=1447.491 [M+Na], measured value=1447.296 [M+Na]

Example 27

Dimer amidite: Synthesis of Substance VII$_{Typ}$base=C, Formula 52 pressure chromatography (2% by volume Et$_3$N-containing dichloromethane:ethanol, volume ratio gradually changed from 1:0 to 9:1) to obtain 0.187 mg of the target product, VII$_{Typ}$base=C (yield 76%).

$^1$H-NMR (300 MHz, DMSO-d6) δ: 1.13 (21H, m), 2.26 (1H, m), 2.45 (1H, m), 2.52 (2H, m), 2.78 (2H, m), 2.89 (2H, m), 3.13 (1H, m), 3.33 (1H, m), 3.5-3.8 (4H, m), 3.60 (2H, s), 3.68 (6H, s), 3.95 (2H, br·d, J=3.5 Hz), 4.1-4.3 (6H, m), 4.49 (1H, m, C(3')H), 5.04 (1H, m, C(3')H), 6.13 (2H, m), 6.49 (1H, d, J=7.7 Hz), 6.49 (4H, d=8.4 Hz), 6.94 (1H, dd, J=7.3, 7.7 Hz), 6.73 (1H, dd, J=7.3, 7.7 Hz), 7.1-7.7 (25H, m), 7.99

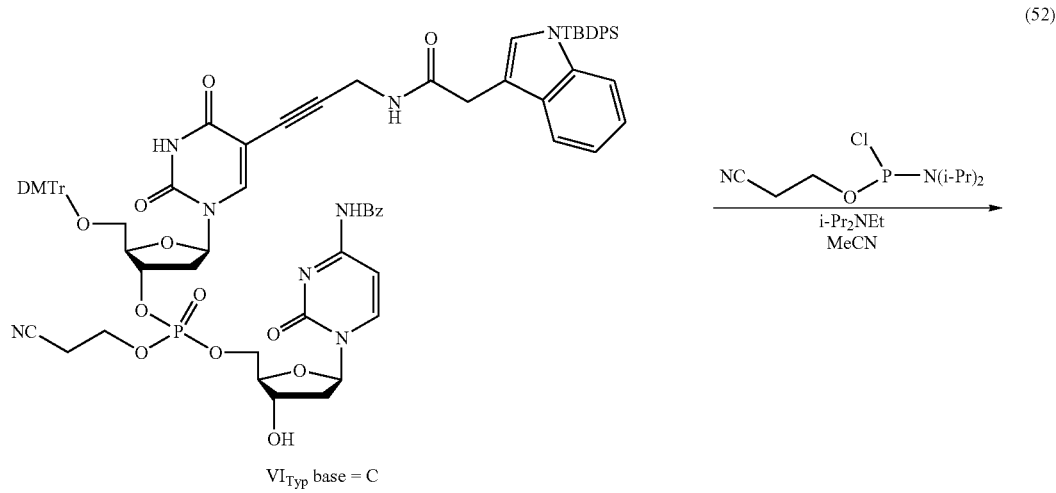

(52)

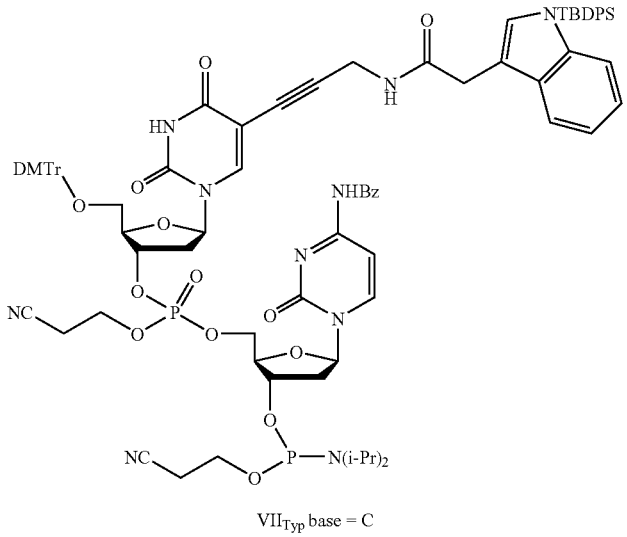

Substance VI$_{Typ}$base=C (0.214 g, 0.150 mmol) was azeotropically dehydrated three times with dry acetonitrile, and thoroughly dried with a vacuum pump. 1.5 mL of acetonitrile was added, and after addition of diisopropylethylamine (34 μL, 0.197 mmol) and cooling to 0° C., diisopropylchlorophosphoramidite (0.04 mL, 0.179 mmol) was added and agitated for 1 hour at 0° C.

After addition of 0.1 mL methanol to inactivate the excess amidite-forming reagent, this was purified by intermediate (2H, d, J=7.7 Hz), 8.11 (1/2H, br·d, J=8.4 Hz), 8.13 (1/2H, br·d, J=8.4 Hz), 8.50 (1H, br), 11.28 (1H, br·s), 11.71 (1H, br·s)

$^{31}$P-NMR (120 MHz, DMSO-d6, BCM) δ: −2.11, −2.06, −1.96, 148.45, 148.52, 148.60

MALDI-TOF MS: Calculated value $(C_{87}H_{94}N_{10}NaO_{16}P_2Si)$=1647.5991, measured value=1647.500

Example 28

Synthesis of Substance at Right of Formula 53

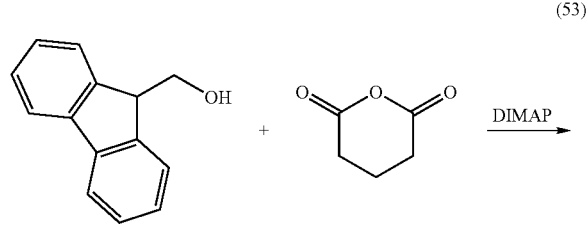

A 90 mL mixed dry methylene chloride solution comprising 5.89 g (30 mmol) 9-fluorenemethanol, 4.11 g (36 mmol) glutaric anhydride, 168 mg (1.5 mmol) DIMAP and 5.0 mL (36 mmol) triethylamine was agitated for 4 hours at room temperature. The reaction solution was washed with water, and the water layer was further extracted twice with methylene chloride. The combined methylene chloride layer was dried with anhydrous sodium sulfate, and concentrated.

The concentrated residue was purified by intermediate pressure chromatography (1% by volume acetic acid-dichloromethane solution:ethanol, volume changed gradually from 1:0 to 19:1) to obtain 8.20 g of the target product (yield 88%).

$^1$H-NMR (DMSO) δ: 1.68 (2H, tt, J=7.5, 7.3 Hz), 2.18 (2H, t, J=7.3 Hz), 2.34 (2H, t, J=7.5 Hz), 4.25 (1H, t, J=6.6 Hz), 4.39 (2H, d, J=6.6 Hz), 7.32 (2H, td, J=7.5, 1.3 Hz), 7.41 (2H, br·t, J=7.3 Hz), 7.64 (2H, br·d, J=7.3 Hz), 7.88 (2H, br·d, J=7.5 Hz), 12.03 (1H, br·s)

Example 29

Monomer: Synthesis of Substance II$_{Glu}$, Formula 54

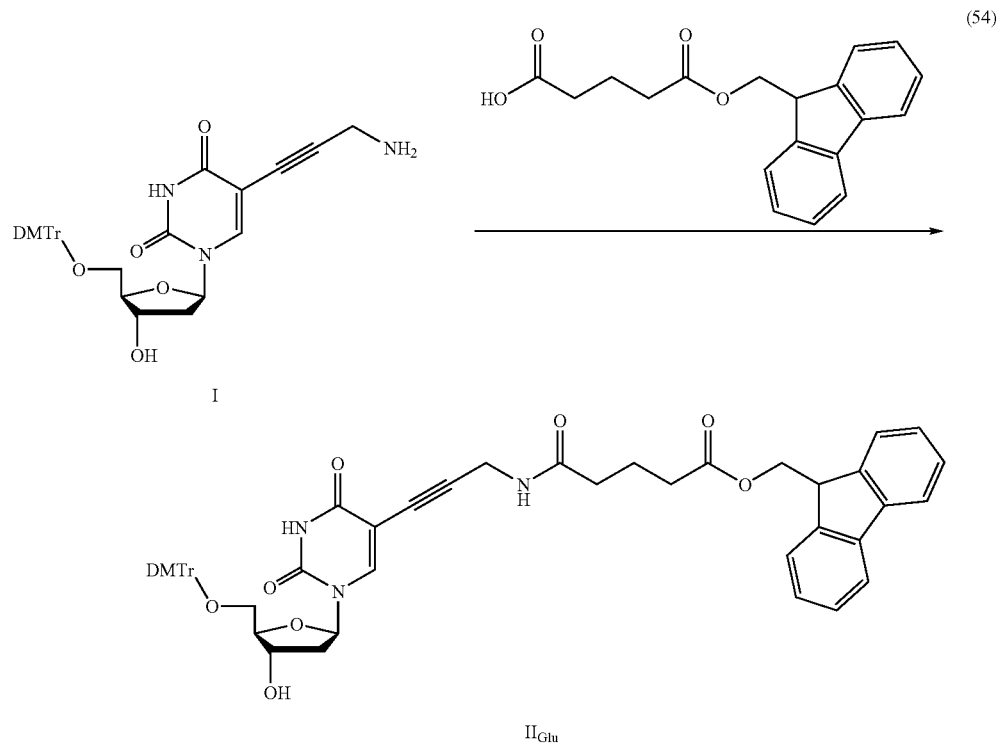

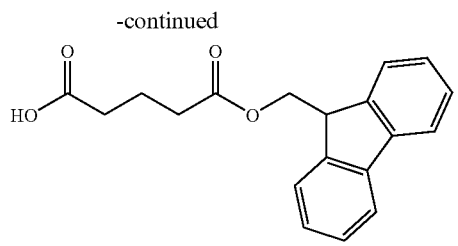

2.22 g of DCC (10.8 mmol) was added to a 50 mL dry methylene chloride solution of 3.12 g (10.5 mmol) of glutaric acid 9-fluorenemethanol half ester and 1.68 g (11.0 mmol) of HOBT monohydrate, and agitated for 30 minutes at room temperature. The reaction solution with the insoluble matter filtered out was added at 0° C. to a 100 mL dichloromethane solution of 5.84 g (10 mmol) of Substance I. The mixed solution was agitated for 1 hour at room temperature. The reaction solution was washed with water, and the water layer was further extracted twice with methylene chloride. The combined methylene chloride layer was dried with anhydrous sodium sulfate, and concentrated. The concentrated residue was purified by intermediate pressure chromatography (dichloromethane-ethanol, volume ratio changed gradually from 19:1 to 9:1) to obtain 7.31 g of the target product, $II_{Glu}$ (yield 83%).

$^1$H-NMR (300 MHz, DMSO-d6) δ: 1.69 (2H, m), 2.08 (2H, t, J=7.3 Hz), 2.18 (1H, m), 2.27 (1H, dd, J=6.8, 13.2 Hz), 2.31 (2H, t, J=7.3 Hz), 3.07 (1H, dd, J=2.9, 10.5 Hz), 3.24 (1H, dd, J=5.6, 9.4 Hz), 3.72 (6H, s), 3.89 (2H, d, J=5.0 Hz), 3.90 (1H, m), 4.24 (1H, t, J=6.6 Hz), 4.25 (1H, m), 4.36 (2H, d, J=6.6 Hz), 5.29 (1H, d, J=4.6 Hz), 6.08 (1H, dd, J=6.4, 6.8 Hz), 6.87 (2H, d, J=8.9 Hz), 6.87 (2H, d, J=8.9 Hz), 7.20-7.45 (13H, m), 7.63 (2H, d, J=7.7 Hz), 7.87 (2H, d, J=7.1 Hz), 7.88 (1H, s), 8.14 (1H, t, J=5.0 Hz), 11.62 (1H, s)

MALDI-TOF MS: Calculated value $(C_{52}H_{50}N_3O_{10}^+)$ =876.3491, measured value=876.207

Example 30

Monomer Amidite: Synthesis of Substance $III_{Glu}$, Formula 55 a saturated aqueous sodium bicarbonate solution and a saturated aqueous sodium chloride solution. Purification by intermediate pressure chromatography (2% by volume Et$_3$N-containing dichloromethane:hexane, volume ratio changed gradually from 1:1 to 1:0, followed by 2% by volume Et$_3$N-containing dichloromethane:ethanol, volume ratio changed gradually from 1:0 to 19:1) yielded 442 mg of Substance $II_{Glu}$ (yield 81%).

$^1$H-NMR (300 MHz, DMSO-d6) δ: 0.96 (3H, d, J=6.8 Hz), 1.08 (3H, d, J=6.8 Hz), 1.09 (6H, d, J=6.9 Hz), 1.69 (2H, tt, J=6.9, 6.6 Hz), 2.08 (2H, t, J=6.6 Hz), 2.31 (2H, t, J=6.9 Hz), 2.39 (2H, m), 2.65 (2H×1/2, t, J=5.8 Hz), 2.76 (2H×1/2, t, J=5.8 Hz), 3.17 (1H, m), 3.27 (1H, m), 3.53 (2H, m), 3.59 (2H, m), 3.71 (3H, s), 3.71 (3H, s), 3.89 (2H×1/2, d, J=5.4 Hz), 3.93 (2H×1/2, d, J=5.4 Hz), 4.02 (1H×1/2, m), 4.05 (1H×1/2, m), 4.24 (1H, t, J=6.6 Hz), 4.36 (2H, d, J=6.6 Hz), 4.46 (1H, m), 6.06 (1H×1/2, dd, J=7.3, 7.0 Hz), 6.08 (1H×1/2,

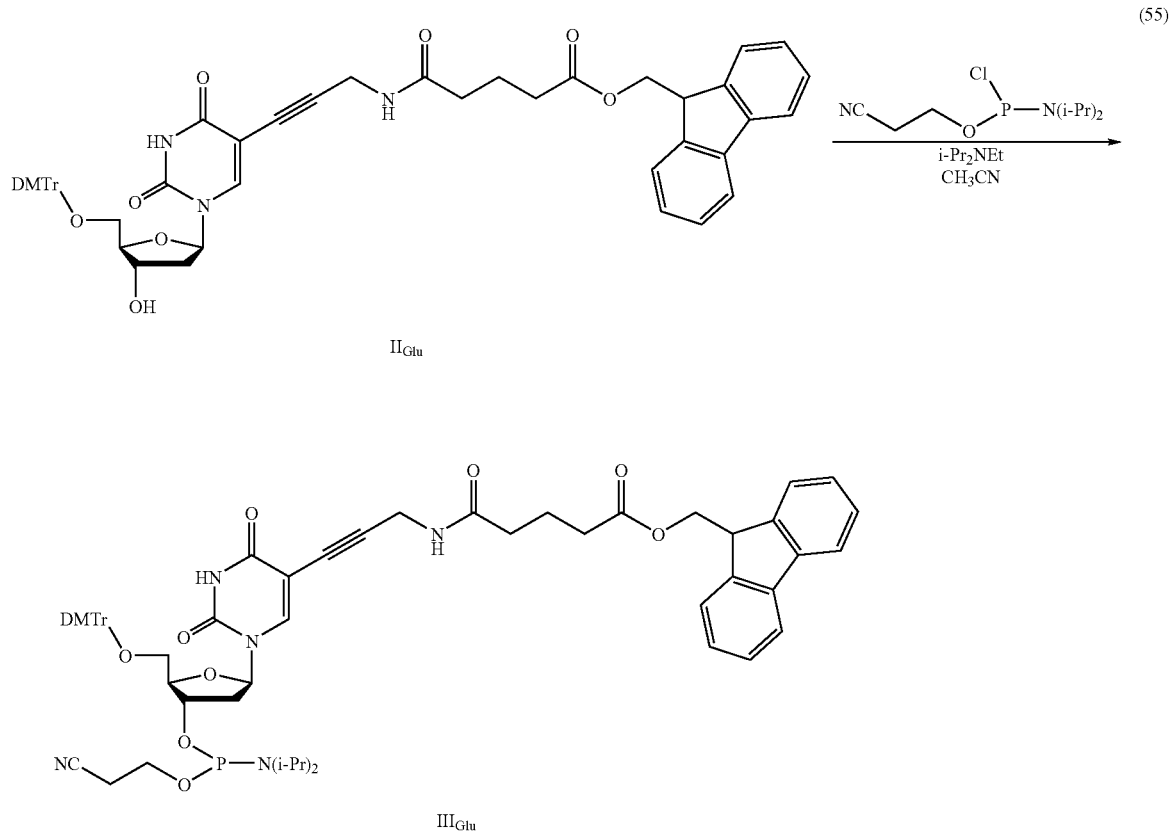

Substance $II_{Glu}$ (445 mg, 0.51 mmol) was azeotropically dehydrated 3 times in 5 mL of dry acetonitrile, and dried. This was dissolved in 11 mL of dry acetonitrile, and after addition of 106 µL (0.61 mmol) of diisopropylethylamine, diisopropylchlorophosphoramidite (124 µL, 0.56 mmol) was added under ice cooling. After 2 hours of agitation, methanol was added to inactivate the excess amidite-forming reagent, followed by dilution with methylene chloride, and washing with dd, J=7.0, 6.8 Hz), 6.85 (4H×1/2, d, J=9.0 Hz), 6.87 (4H×1/2, d, J=9.0 Hz), 7.18-7.42 (13H, m), 7.63 (2H, d, J=7.2 Hz), 7.88 (2H, d, J=7.2 Hz), 7.93 (1H×1/2, s), 7.94 (1H×1/2, s), 8.19 (1H×1/2, br·t, J=5.4 Hz), 8.21 (1H×1/2, br·t, J=5.4 Hz), 11.58 (1H, br·s)

$^{31}$P-NMR (120 MHz, DMSO-d6) δ: 147.65, 148.05

MALDI-TOF MS: Calculated value $(C_{61}H_{67}N_5O_{11}P^+)$= 1076.4569 [M+H], measured value=1075.944 [M+H]

Example 31

Levuloyl Group Introduction and DMTr Removal:
Synthesis of Substance IX$_{Glu}$, Formula 56

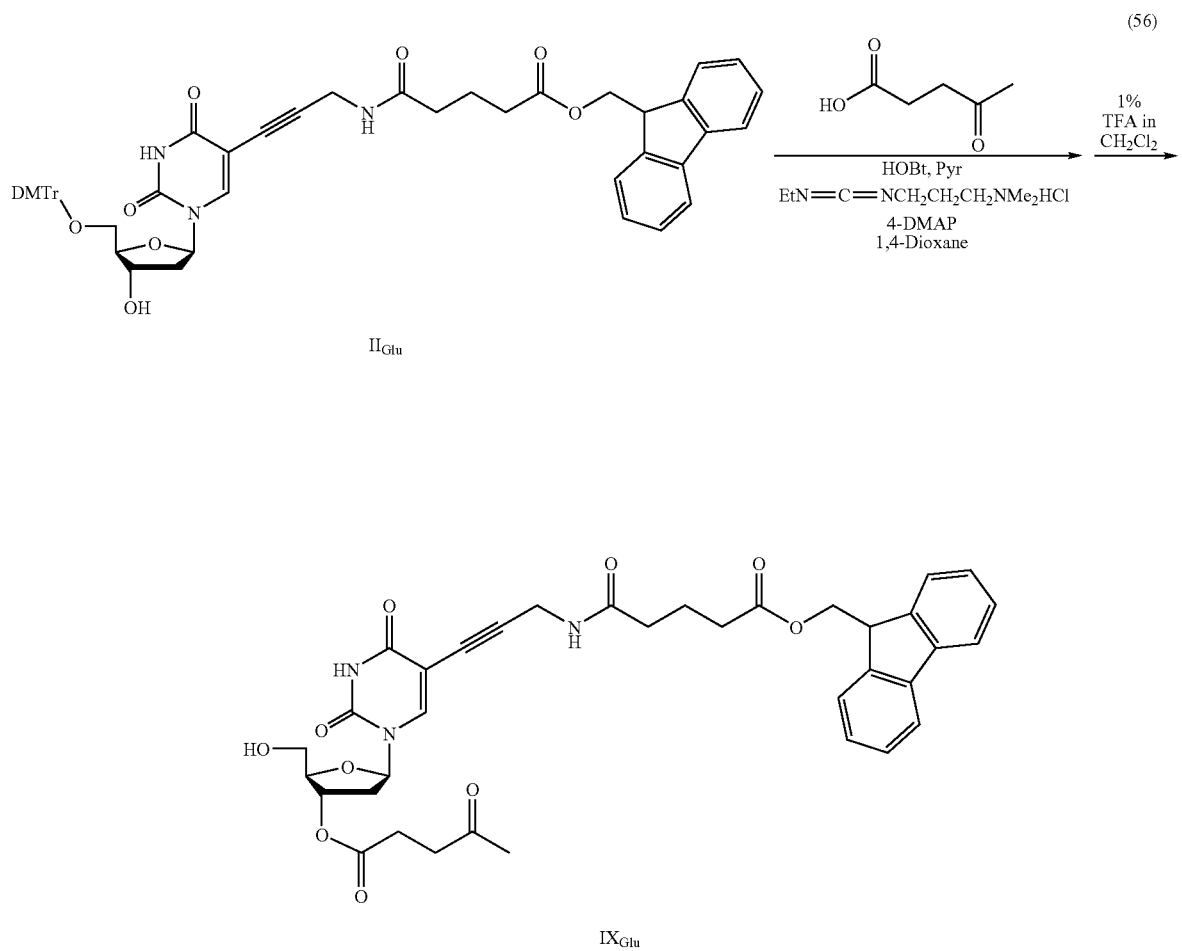

Substance II$_{Glu}$ (2.18 g, 2.49 mmol) was dissolved in 1,4-dioxane (25 mL), and pyridine (0.60 mL, 7.42 mmol), N-ethyl-N'-(dimethylaminopropyl)carbodiimide hydrochloride (1.18 g, 6.18 mmol), 4-dimethylaminopyridine (0.0316 g, 0.259 mmol) and levulinic acid (0.51 mL, 4.96 mmol) were added successively at room temperature. After 5 hours and 20 minutes of agitation at room temperature, this was partitioned between with methylene chloride and a saturated sodium bicarbonate aqueous solution, and then extracted twice with methylene chloride. The combined methylene chloride layer was washed with a saturated aqueous sodium chloride solution, dried with anhydrous sodium sulfate, and concentrated.

The concentrated residue was dissolved in 57 mL methylene chloride and ice cooled, and trifluoracetic acid (550 µL) was added and agitated for 1 hour at 0° C. After neutralization of most of the trifluoracetic acid by addition of a sodium bicarbonate powder this was filtered and concentrated. The concentrated residue was purified by intermediate pressure chromatography (dichloromethane-ethanol, volume ratio gradually changed from 1:0 to 9:1) to obtain 1.30 g of the target product, IX$_{Glu}$ (yield 78%).

$^1$H-NMR (300 MHz, DMSO-d6) δ: 1.71 (2H, m), 2.07 (2H, m), 2.1 (3H, s), 2.25 (2H, m), 2.33 (2H, t, J=7.4 Hz), 2.49 (2H, m), 2.73 (2H, m), 3.61 (2H, dd, J=3.5, 4.5 Hz), 3.99 (1H, m), 4.07 (2H, d, J=5.5 Hz), 4.25 (1H, t, J=6.6 Hz), 4.37 (1H, d, J=6.6 Hz), 5.19 (1H, m), 6.12 (1H, dd, J=6.4, 7.7 Hz), 7.32 (2H, ddd, J=1.1, 7.3, 7.5 Hz), 7.41 (2H, dd, J=7.3, 7.5 Hz), 7.64 (2H, d, J=7.3 Hz), 7.88 (2H, d, J=7.5 Hz), 8.15 (1H, s), 8.27 (1H, 5, J=5.5 Hz)

MALDI-TOF MS: Calculated value ($C_{36}H_{38}N_3O_{10}^+$)= 672.2552 [M+H], measured value 672.382

Example 32

Dimer: Synthesis of Substance $X_{Glu}$base=G, Formula 57

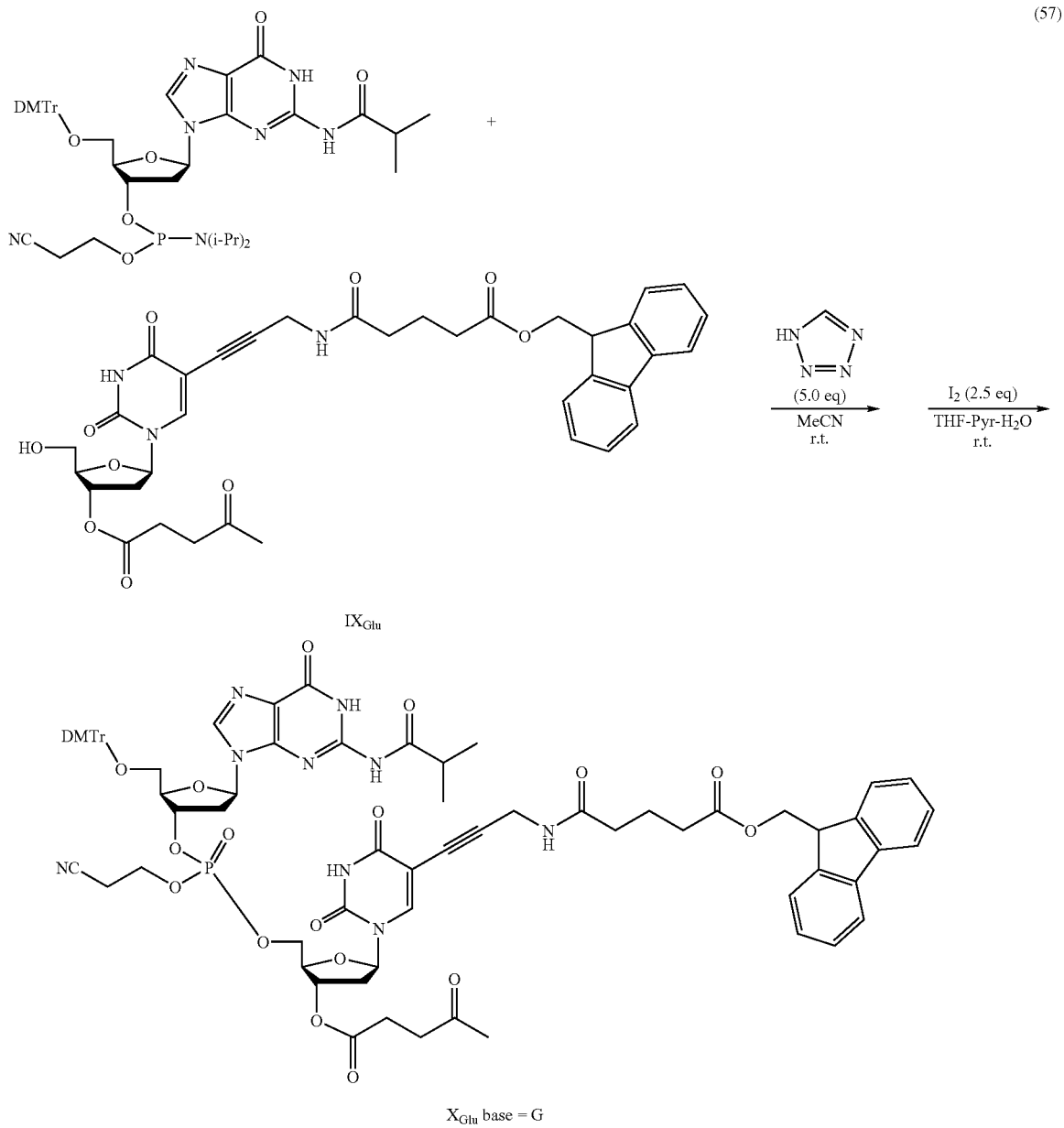

$X_{Glu}$ base = G

Substance $IX_{Glu}$ (1.48 g, 2.20 mmol) was azeotropically dehydrated three times with dry acetonitrile, and dried with a vacuum pump. 5'-(4,4'-dimethoxytriphenylmethyl)-guanosine-3'-(diisopropylamino)cyanoethylphosphoramidite (2.25 g, 2.68 mmol) was added thereto, followed by 12 mL of dry acetonitrile, and an 0.45 mol/L tetrazole/acetonitrile solution (25 mL, tetrazole 11.3 mmol) was added and agitated for 45 minutes at room temperature. This was partitioned by addition of methylene chloride and a saturated aqueous sodium bicarbonate solution, the water layer was extracted twice with methylene chloride, and the combined methylene chloride layer was washed with a saturated aqueous sodium chloride solution, dried with anhydrous sodium sulfate, and concentrated.

The concentrated residue was diluted with 23 mL THG, and 23 mL of an 0.12 mol/L iodine/THF-pyridine-water (volume ratio 2:2:1) solution was added at room temperature and agitated for 30 minutes. After dilution with methylene chloride, a 10% by weight aqueous sodium thiosulfate solution was added to reduce the excess iodine, the water layer was extracted twice with methylene chloride, and the combined methylene chloride layer was washed with a saturated aqueous sodium chloride solution, dried with anhydrous sodium sulfate, and concentrated.

The concentrated residue was purified by intermediate pressure chromatography (dichloromethane-ethanol, volume ratio changed gradually from 1:0 to 9:1) to obtain 2.66 g of the target product, X$_{Glu}$base=G (yield 85%).

$^1$H-NMR (300 MHz, DMSO-d6) δ: 1.11 (6H, d, J=6.6 Hz), 1.70 (2H, m), 2.07 (3H, s), 2.09 (2H, m), 2.23 (1H, m), 2.32 (2H, m), 2.46 (1H, m), 2.49 (2H, m), 2.70 (2H, m), 2.73 (1H, m), 2.74 (1H, m), 2.89 (2H, m), 3.02 (1H, m), 3.17 (1H, m), 3.29 (1H, m), 3.70 (6H, s), 4.04 (2H, m), 4.1-4.30 (7H, m), 4.36 (2H, d, J=6.6 Hz), 5.13 (2H, m), 6.09 (1H, m), 6.26 (1H, m), 6.78 (2H, d, J=8.3 Hz), 6.80 (2H, d, J=8.3 Hz), 7.1-7.5 (13H, m), 7.93 (1/2H, s), 7.95 (1/2H, s), 8.08 (1/2H, s), 8.09 (1/2H, s), 8.25 (1H, br), 11.55 (1H, br), 11.67 (1H, br), 12.05 (1H, br)

$^{31}$P-NMR (DMSO-d6) δ: −2.31

MALDI-TOF MS: Calculated value (C$_{74}$H$_{76}$N$_9$NaO$_{19}$P$^+$)=1448.489 [M+Ns], measured value=1448.443 [M+Na]

Example 33

Dimer Levuloyl Removal: Synthesis of Substance XI$_{Glu}$base=G, Formula 58

Substance X$_{Glu}$base=G (2.66 g, 1.86 mmol) was dissolved in 19 mL pyridine and cooled to 0° C., and a mixed pyridine-acetic acid (volume ratio 3:2) solvent solution (19 mL) of hydrazine monohydrate (0.91 mL, 18.7 mmol) was dripped in. After completion of dripping this was agitated at 0° C. for 45 minutes, and 2 mL of acetone was added to convert excess hydrazine to azone. The reaction liquid was diluted with methylene chloride, and after neutralization of the acetic acid with a saturated aqueous sodium bicarbonate solution and partitioning, the water layer was extracted twice with methylene chloride. The combined methylene chloride layer was washed with a saturated aqueous sodium chloride solution, dried with anhydrous sodium sulfate, and concentrated.

The concentrated residue was purified by intermediate pressure chromatography (dichloromethane-ethanol, volume ratio changed gradually from 1:0 to 9:1) to obtain 1.95 g of the target product, XI$_{Glu}$base=G (yield 81%).

$^1$H-NMR (300 MHz, DMSO-d6) δ: 1.11 (6H, d, J=6.6 Hz), 1.69 (2H, m), 2.07 (2H, m), 2.07 (1H, m), 2.21 (1H, m), 2.31 (2H, m), 2.72 (2H, m), 2.90 (2H, m), 3.02 (1H, m), 3.18 (1H, m), 3.28 (1H, m), 3.70 (6H, s), 3.91 (1H, m), 4.04 (2H, m), 4.1-4.3 (6H, m), 4.35 (1H, d, J=6.6 Hz), 5.10 (1H, m), 5.45

(58)

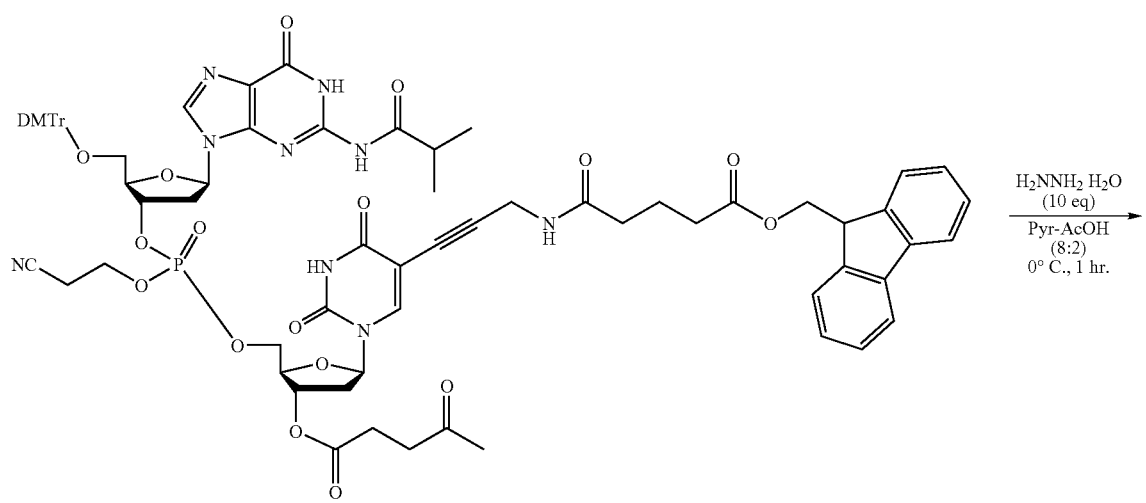

X$_{Glu}$ base = G

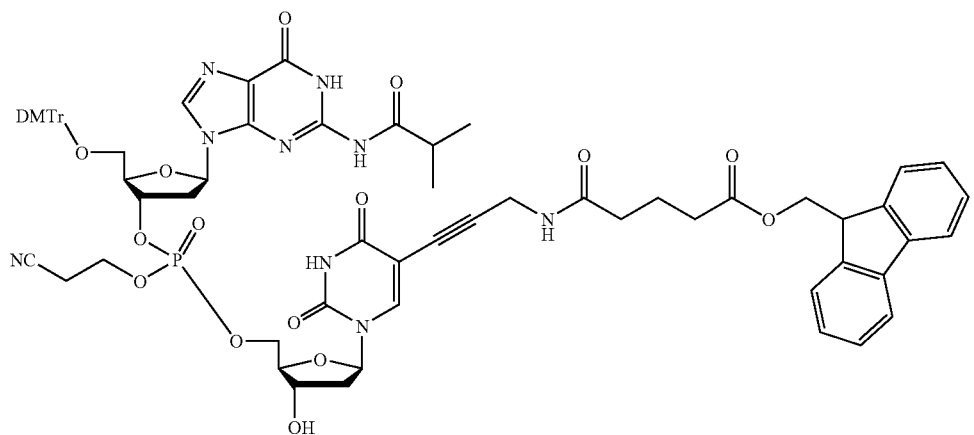

XI$_{Glu}$ base = G (1H, m), 6.10 (1H, m), 6.26 (1H, m), 6.78 (2H, d, J=8.3 Hz, 4H of DMTr), 6.80 (2H, d, J=8.3 Hz), 7.1-7.35 (1H, m), 7.39 (2H, t, J=7.3 Hz), 7.62 (2H, d, J=7.3 Hz), 7.87 (2H, d, J=7.3 Hz), 7.88 (1H, m), 8.10 (1/2H, s), 8.11 (1/2H, s), 8.29 (1H, br), 11.59 (1H, br), 11.66 (1H, br), 12.06 (1H, br)

$^{31}$P-NMR (BCM, DMSO-d6) δ: −1.96, −2.01

MALDI-TOF MS: Calculated value $(C_{69}H_{70}N_9NaO_{17}P^+)$=1350.4519 [M+Na], measured value=1350.411 [M+Na]

Example 34

Dimer Amidite: Synthesis of Substance XII$_{Glu}$base=G, Formula 59

Substance XI$_{Glu}$base=G (203 mg, 0.153 mmol) was azeotropically dehydrated three times with dry acetonitrile, and thoroughly dried with a vacuum pump. 1.5 mL of acetonitrile was added, diisopropylethylamine (34 μL, 0.197 mmol) was added, and the mixture was cooled to 0° C. and agitated for 2 hours at 0° C. after addition of diisopropylchlorophosphoramidite (0.04 mL, 0.179 mmol).

After addition of 0.1 mL methanol to inactivate the excess amidite-forming reagent, this was purified by intermediate pressure chromatography (2% by volume Et$_3$N-containing dichloromethane:ethanol, volume ratio changed gradually from 1:0 to 9:1) to obtain 124 mg of the target product, XII$_{Glu}$base=G (yield 53%).

$^1$H-NMR (300 MHz, DMSO-d6) δ: 1.10 (18H, m), 1.68 (2H, m), 2.07 (2H, t, J=7.3 Hz), 2.2 (1H, m), 2.31 (2H, t, J=7.3 Hz), 2.4 (1H, m), 2.7 (2H, m), 2.75 (2H, m), 2.88 (2H, m),

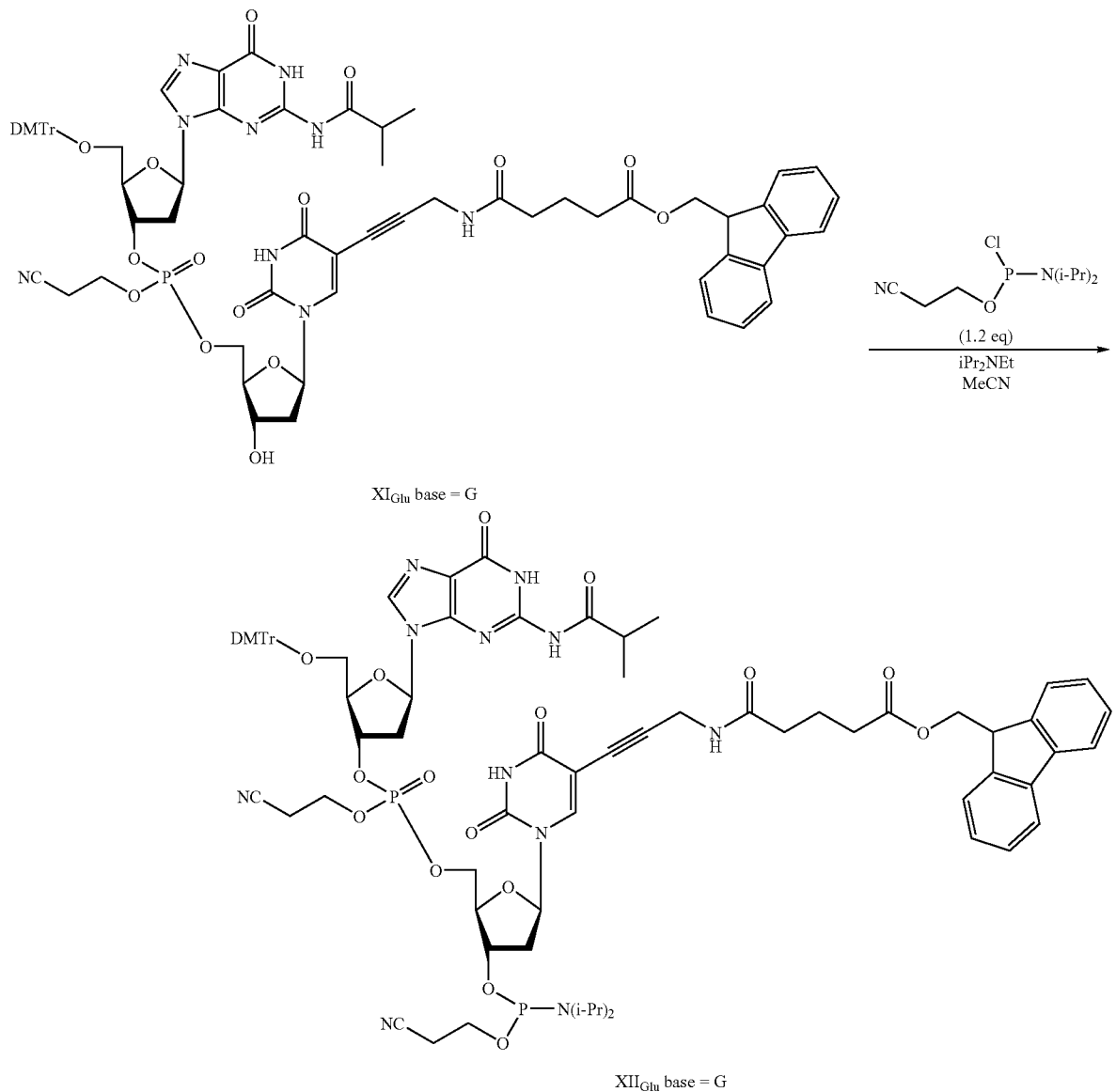

XI$_{Glu}$ base = G

XII$_{Glu}$ base = G (59)

3.03 (1H, m), 3.15 (1H, m), 3.28 (1H, m), 3.54 (2H, m), 3.70 (6H, s), 3.70 (2H, m), 4.03 (2H, m), 4.0-4.3 (7H, m), 4.35 (2H, d, J=6.6 Hz, 2H), 4.45 (1H, br), 5.10 (1H, m), 6.08 (1H, m), 6.25 (1H, m), 6.77 (4H×1/2, d, J=6.9 Hz), 6.79 (4H×1/2, d, J=6.9 Hz), 7.1-7.25 (7H, m), 7.3 (4H, m), 7.39 (2H, dd, J=7.2, 7.3 Hz), 7.62 (2H, dd, J=7.3 Hz), 7.87 (2H, d, J=7.3 Hz), 7.90 (1/4H, s), 7.91 (1/4H, s), 7.92 (1/4H, s), 7.93 (1/4H, s), 2.92 (1/2H, s), 8.11 (1/4H, s), 8.11 (1/4H, s), 8.29 (1H, br), 11.58 (1H, br), 11.67 (1H, br), 12.06 (1H, br)

$^{31}$P-NMR (120 MHz, DMSO-d6) δ: −2.06, −1.99, 148.47

MALDI-TOF MS: Calculated value $(C_{78}H_{88}N_{10}O_{18}P_2+$ [M+H]$^+$)=1528.578, measured value=1528.492

Example 35

Monomer: Synthesis of Substance II$_{Leu}$, Formula 60

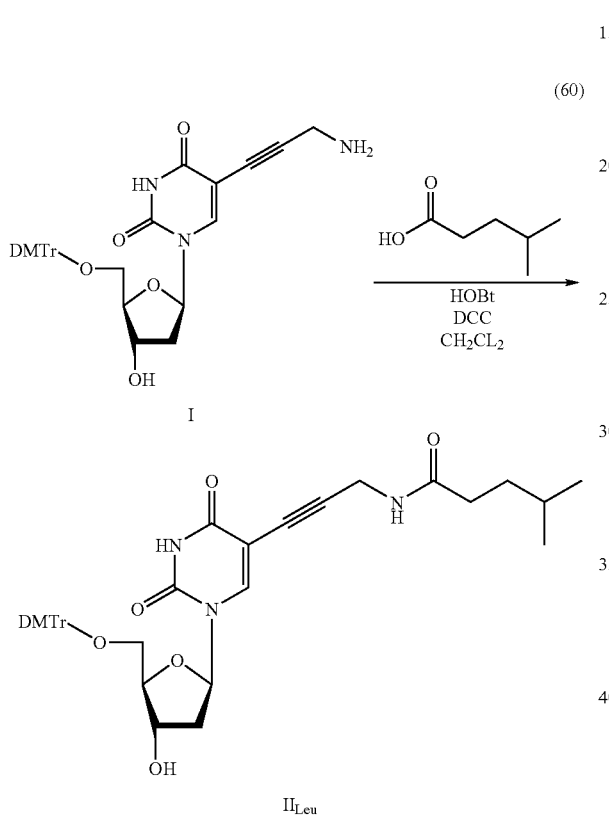

1.86 g (9.0 mmol) of DCC was added to a 43 mL dry methylene chloride solution of 1.13 mL (9.0 mol) valeric acid and 1.44 g (9.4 mmol) HOBT monohydrate, and agitated for 30 minutes at room temperature. The reaction solution with the insoluble matter filtered out was added to a dichloromethane solution (86 mL) of Substance I (6.27 g, 80% by weight, 8.6 mmol) at 0° C. The mixed solution was agitated for 1 hour at room temperature. The reaction solution was washed in water, and the water layer was extracted twice with methylene chloride. The combined methylene chloride layer was dried with anhydrous sodium sulfate, and concentrated. The concentrated residue was purified by intermediate pressure chromatography (dichloromethane-ethanol, volume ratio changed gradually from 19:1 to 9:1) to obtain 4.46 g of the target product, III$_{Leu}$ (yield 73%).

$^1$H-NMR (DMSO-d6) δ: 0.83 (6H, d, J=6.4 Hz), 1.35 (2H, m), 1.47 (1H, m), 2.06 (2H, t, J=7.9 Hz), 2.24 (2H, m), 3.07 (1H, br·d, J=7.7 Hz), 3.3 (1H, m), 3.73 (6H, s), 3.89 (3H, m), 4.25 (1H, m), 5.29 (1H, d, J=4.5 Hz), 6.09 (1H, d, J=6.6 Hz, OH), 6.88 (4H, d, J=7.9 Hz), 7.2-7.5 (9H, m), 7.87 (1H, s), 8.12 (1H, br), 11.62 (1H, br)

MALDI-TOF MS: Calculated value $(C_{39}H_{44}N_3O_8^+)=$ 682.312 [M+H]$^+$, measured value=682.098 [M+H]$^+$ Example 36

Monomer Amidite: Synthesis of Substance III$_{Leu}$, Formula 61

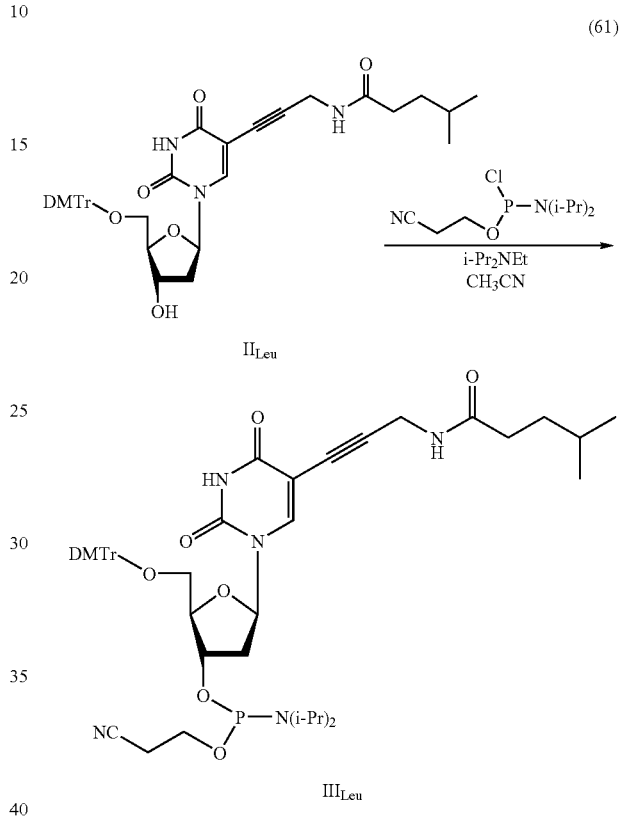

Substance II$_{Leu}$ (341 mg, 0.50 mmol) was azeotropically dehydrated three times in 5 mL of dry acetonitrile, and dried. This was dissolved in 10 mL of dry acetonitrile, and after addition of 104 μL (0.60 mmol) diisopropylethylamine, diisopropylchlorophosphoramidite (122 μL, 0.55 mmol) was added under ice cooling. After 2 hours of agitation, methanol was added to inactivate the excess amidite-forming reagent, followed by dilution with methylene chloride, and washing with a saturated aqueous sodium bicarbonate solution and a saturated aqueous sodium chloride solution. Purification by intermediate pressure chromatography (2% by volume Et$_3$N-containing dichloromethane:hexane, volume ratio changed gradually from 1:1 to 1:0, followed by 2% by volume Et$_3$N-containing dichloromethane:ethanol, volume ratio changed gradually from 1:0 to 19:1) yielded 407 mg of Substance III$_{Leu}$ (yield 92%).

$^1$H-NMR (300 MHz, DMSO-d6) δ: 0.83 (6H, d, J=6.4 Hz), 0.97 (3H, d, J=6.8 Hz), 1.09 (6H, d, J=7.2 Hz), 1.12 (3H, d, J=7.2 Hz), 1.37 (2H, m), 1.46 (1H, m), 2.06 (2H, t, J=7.4 Hz), 2.30 (1H, m), 2.40 (1H, m), 2.64 (2H×1/2, t, J=5.3 Hz), 2.75 (1H×1/2, t, J=5.7 Hz), 3.14 (1H, m), 3.28 (1H, m), 3.52 (2H, m), 3.62 (2H, m), 3.73 (6H, s), 3.89 (2H×1/2, d, J=5.3 Hz), 3.92 (2H×1/2, d, J=5.3 Hz), 4.03 (1H, m), 4.48 (1H, m), 6.07 (1H, m), 6.86 (2H, d, J=8.6 Hz), 6.88 (2H, d, J=8.6 Hz), 7.20-7.35 (7H, m), 7.39 (2H, d, J=7.3 Hz), 7.93 (1H, br), 8.15 (1/2H, t, J=5.3 Hz), 8.17 (1/2H, t, J=5.3 Hz)

$^{31}$P-NMR (120 MHz, DMSO) δ: 147.80, 148.20
MLDI-TOF: Calculated value $(C_{48}H_{61}N_5O_9P+)=$ 882.4201
$[M+H]^+$, measured value=882.277

Example 37

Monomer Levuloyl Group Introduction and DMTr removal: Synthesis of Substance IX$_{Leu}$, Formula 62

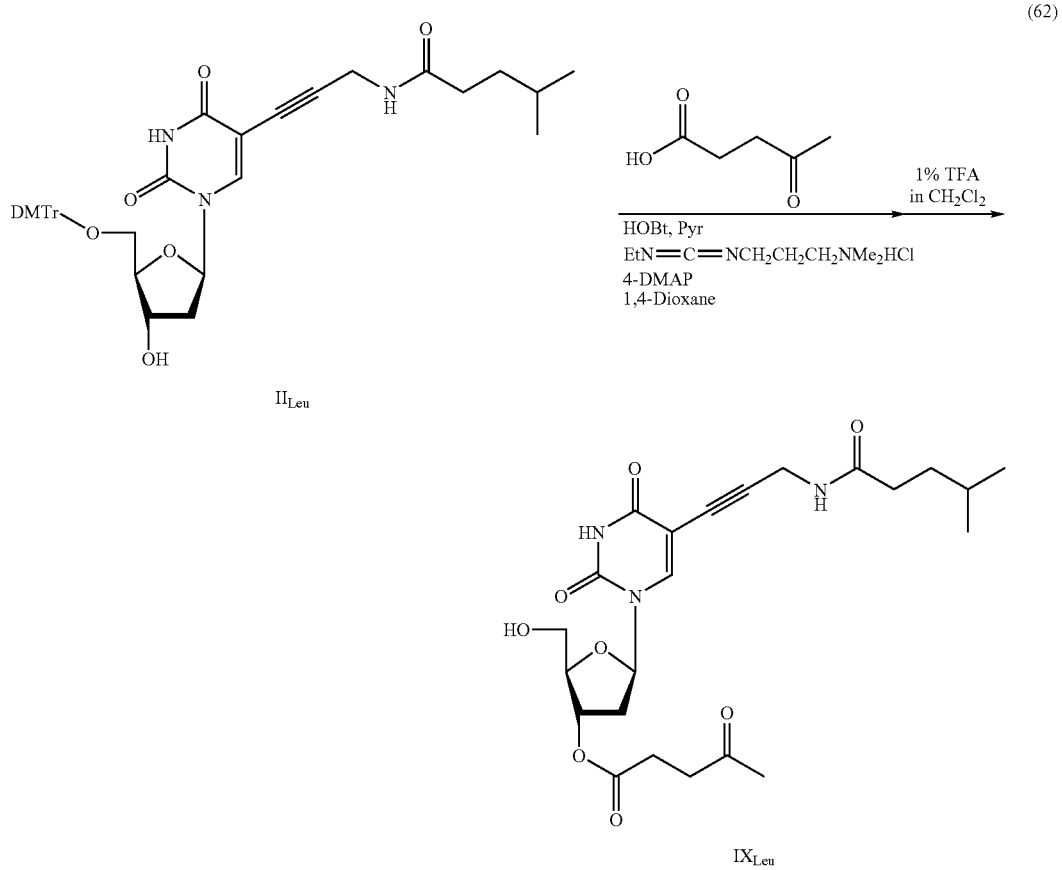

Substance II$_{Leu}$ (1.40 g, 2.05 mmol) was dissolved in 1,4-dioxane (20 mL), and pyridine (0.50 mL, 6.18 mmol), N-ethyl-N'-(dimethylaminopropyl)carbodiimide hydrochloride (0.999 g, 5.21 mmol), 4-dimethylaminopyridine (0.0260 g, 0.213 mmol) and levulinic acid (0.42 mL, 4.09 mmol) were added successively at room temperature. After 2 hours and 50 minutes of agitation at room temperature, this was partitioned between methylene chloride and a saturated aqueous sodium bicarbonate solution, and then extracted twice with methylene chloride. The combined methylene chloride layer was washed with a saturated aqueous sodium chloride solution, dried with anhydrous sodium sulfate, and concentrated.

The concentrated residue was dissolved in 47 mL of methylene chloride, ice cooled, and agitated for 30 minutes at 0° C. after addition of trifluoracetic acid (470 μL). Sodium bicarbonate powder was added to neutralize most of the trifluoracetic acid, followed by filtration and concentration. The concentrated residue was purified by intermediate pressure chromatography (dichloromethane-ethanol, volume ratio changed gradually from 1:0 to 9:1) to obtain 0.759 g of the target product, IX$_{Leu}$ (yield 77%).

$^1$H-NMR (DMSO-d6) δ: 0.84 (6H, d, J=6.4 Hz), 1.39 (2H, m), 1.47 (1H, m), 2.10 (3H, s), 2.10 (2H, m), 2.26 (2H, m), 2.73 (2H, brat, J=6.3 Hz), 2.49 (2H, m), 3.61 (2H, m), 3.99 (1H, m), 4.05 (2H, br·d, J=5.3 Hz), 5.19 (1H, br), 6.12 (1H, dd, J=6.6, 7.5 Hz), 8.14 (1H, s) 8.27 (1H, br), 11.64 (1H, s)

MALDI-TOF MS: Calculated value $(C_{23}H_{32}N_3O_8^+)=$ 478.2184 $[M+H]^+$, measured value=478.276

Example 38

Dimer: Synthesis of Substance X$_{Leu}$base=A, Formula 63

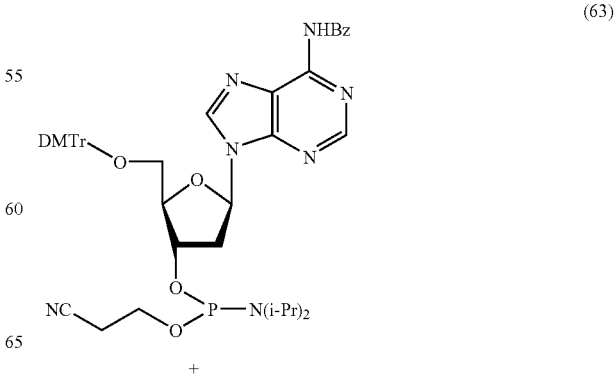

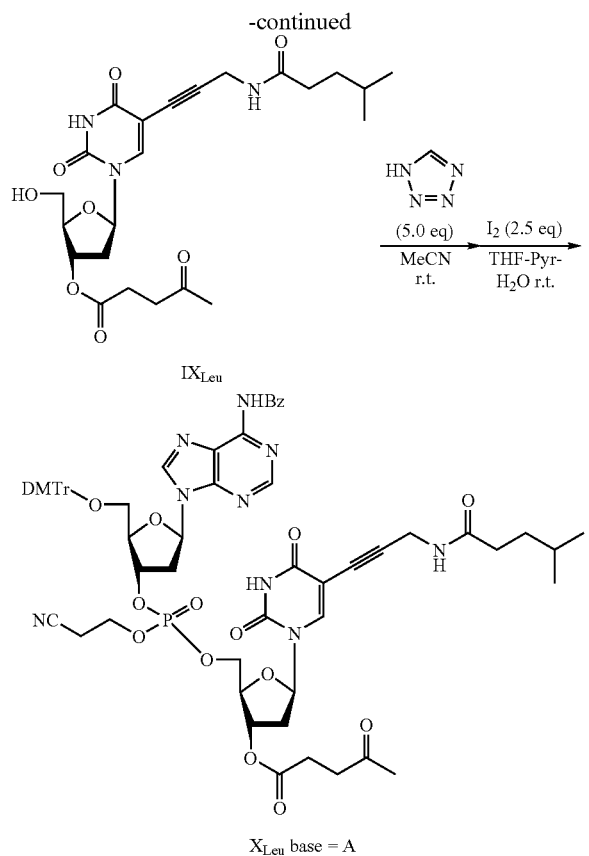

Substance IX$_{Leu}$ (1.27 g, 2.66 mmol) was azeotropically dehydrated three times with dry acetonitrile, and dried with a vacuum pump. 5'-(4,4'-dimethoxytriphenylmethyl)-4-benzoyladenosine-3'-(diisopropylamino) cyanoethylphosphoramidite (2.75 g, 3.21 mmol) was added thereto, 15 mL of dry acetonitrile was added, and a 0.45 mol/L tetrazole/acetonitrile solution (30 mL, tetrazole 11.3 mmol) was added and the mixture was agitated for 45 minutes at room temperature. After partitioning by addition of methylene chloride and a saturated aqueous sodium bicarbonate solution, the water layer was extracted twice with methylene chloride, and the combined methylene chloride layer was washed with a saturated aqueous sodium chloride solution, dried with anhydrous sodium sulfate, and concentrated.

The concentrated residue was diluted in 28 mL of THF, and 23 mL of an 0.12 mol/L iodine/THF-pyridine-water (volume ratio 2:2:1) solution (iodine 6.72 mmol) was added at room temperature and agitated at room temperature for 30 minutes. After dilution with methylene chloride, a 10% by weight aqueous sodium thiosulfate solution was added to reduce the excess iodine, the water layer was then extracted twice with methylene chloride and the combined methylene chloride layer was washed with a saturated aqueous sodium chloride solution, dried with anhydrous sodium sulfate, and concentrated.

The concentrated residue was purified by intermediate pressure chromatography (dichloromethane-ethanol, volume ratio changed gradually from 1:0 to 9:1) to obtain 2.65 g of the target product, X$_{Leu}$base=A (yield 80%).

$^{1}$H-NMR (300 MHz, CDCl$_3$) δ: 0.74 (3H, d, J=6.2 Hz), 0.75 (3H, d, J=6.1 Hz), 1.39 (3H, m), 2.06 (3H×1/2, s), 2.07 (3H×1/2, s), 2.1 (2H, m), 2.23 (1H, m), 2.38 (1H, m), 2.47 (2H, t, J=5.5 Hz), 2.67 (2H, t, J=5.5 Hz), 2.73 (2H, t, J=5.5 Hz), 2.75 (1H, m), 3.13 (1H, m), 3.37 (2H, m), 3.67 (6H×1/3, s), 3.68 (6H×1/3, s), 3.69 (6H×1/3, s), 3.68 (1H, m), 4.0-4.5 (7H, m), 5.25 (2H, m), 6.12 (1H, m), 6.44 (1H, m)

$^{31}$P-NMR (BSM, 120 MHz, DMSO-d6) δ: −2.31

MALDI-TOF MS: Calculated value (C$_{64}$H$_{68}$N$_9$NaO$_{16}$ P$^+$)=1272.4414, measured value=1272.669

Example 39

Dimer Levuloyl Removal: Synthesis of Substance XI$_{Leu}$base=A, Formula 64

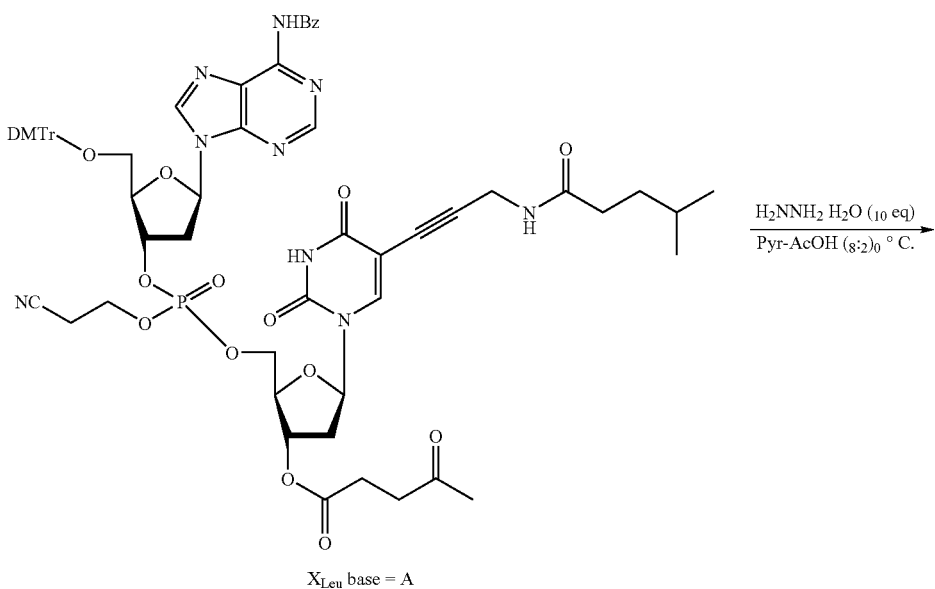

(64)

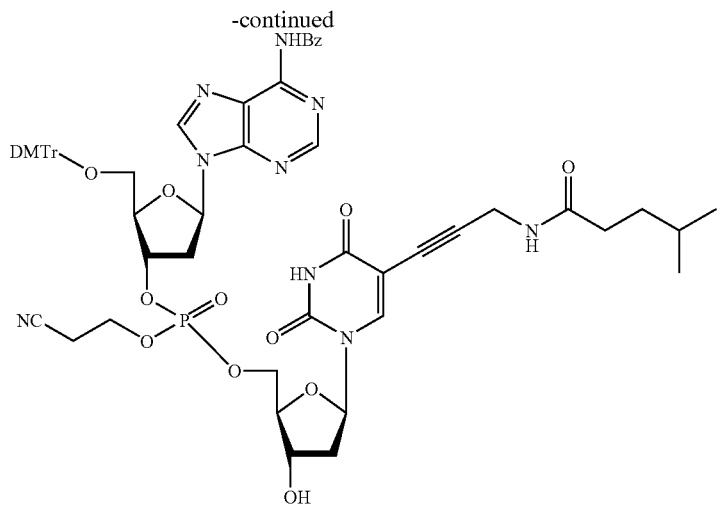

XI$_{Leu}$ base = A

Substance X$_{Leu}$base=A (2.65 g, 2.12 mmol) was dissolved in 21 mL pyridine and cooled to 0° C., and hydrazine monohydrate (1.03 mL, 18.7 mmol) and 21 mL of a mixed pyridine-acetic acid solvent (volume ratio 3:2) were dripped in. After completion of dripping this was agitated for 1 hour at 0° C., and 2 mL acetone was added to convert the excess hydrazine to azone. The reaction liquid was diluted with methylene chloride, and after neutralization of the acetic acid with a saturated aqueous sodium bicarbonate solution and partitioning, the water layer was extracted two times with methylene chloride. The combined methylene chloride layer was washed with a saturated aqueous sodium chloride solution, dried with anhydrous sodium sulfate, and concentrated.

The concentrated residue was purified by intermediate pressure chromatography (dichloromethane-ethanol, volume ratio changed gradually from 1:0 to 9:1) to obtain 2.13 g of the target product, XI$_{Leu}$base=A (yield 87%).

$^1$H-NMR (300 MHz, DMSO-d6) δ: 0.81 (6H, d, J=6.2 Hz), 1.35 (2H, m), 1.44 (1H, m), 2.06 (2H, t, J=7.5 Hz), 2.10 (1H, m), 2.23 (1H, m), 2.77 (1H, m), 2.92 (2H, m), 3.29 (3H, m), 3.71 (6H, s), 3.99 (1H, m), 4.03 (2H, m), 4.15-4.30 (5H, m), 4.35 (1H, m), 5.28 (1H, m), 5.43 (1H, m), 6.11 (1H, m), 6.52 (1H, m), 6.80 (4H×1/2, d, J=8.8 Hz), 6.81 (4H×1/2, d, J=8.6 Hz), 7.10-7.3 (7H, m), 7.33 (2H, d, J=7.5 Hz), 7.54 (2H, dd, J=7.2, 7.5 Hz, Bz), 7.64 (1H, dd, J=7.2, 7.5 Hz), 7.88 (1H, s), 8.03 (2H, d, J=7.5 Hz), 8.55 (1H×1/2, s), 8.22 (1H, br·t, J=5.1 Hz), 8.57 (1H×1/2, s), 11.15 (1H, br), 11.62 (1H, br)

$^{31}$P-NMR (BCM, 120 MHz, DMSO-d6) δ: −1.99, −1.89

MALDI-TOF MS: Calculated value (C$_{59}$H$_{62}$N$_9$NaO$_{14}$P$^+$)=1174.4046 [M+Na]$^+$, measured value=1174.308

Example 40

Dimer Amidite: Synthesis of Substance XII$_{Leu}$base=A, Formula 65

(65)

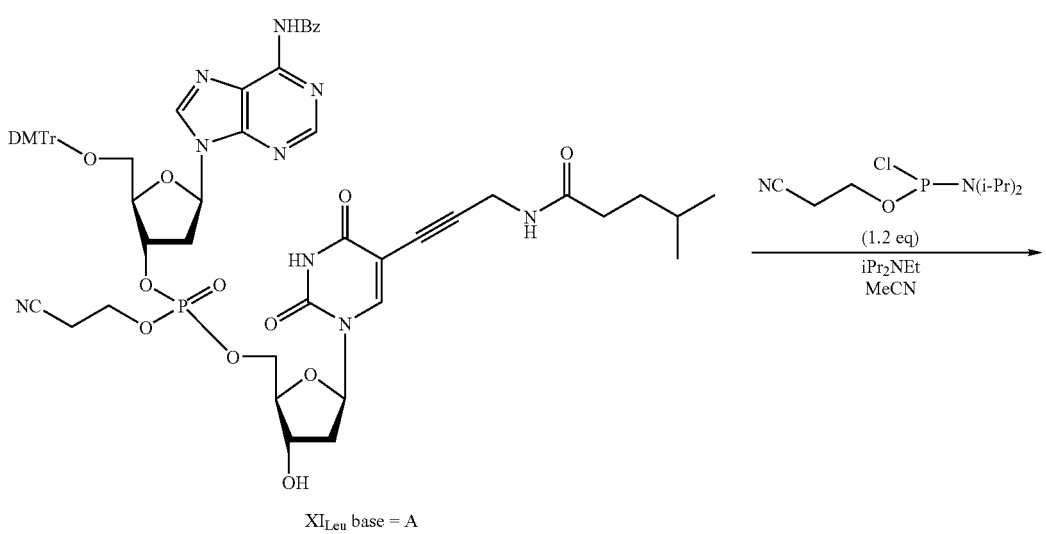

XI$_{Leu}$ base = A

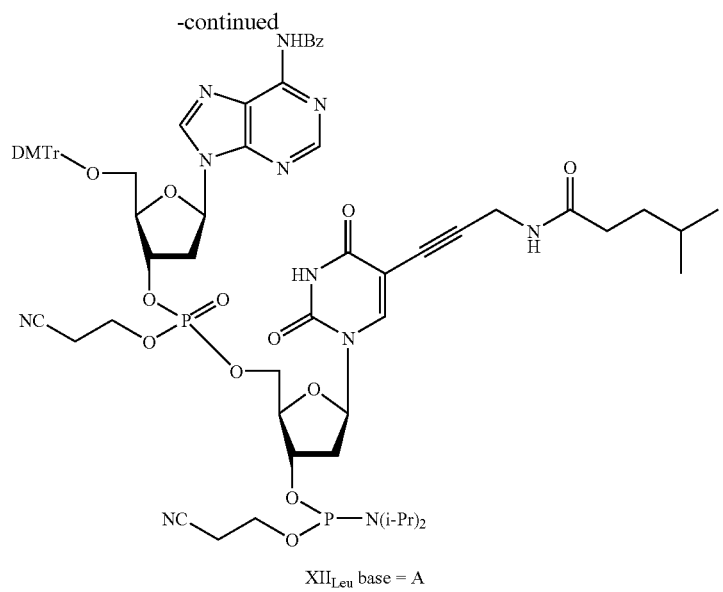

XII$_{Leu}$ base = A

Substance XI$_{Leu}$base=A (0.200 g, 0.174 mmol) was azeotropically dehydrated three times with dry acetonitrile and dissolved in 1.7 mL of dry acetonitrile, and diisopropylethylamine (41 μL, 0.229 mmol) was added. Cyanoethylchlorodiisopropylphosphoramidite (47 μL, 0.211 mmol) was then added and agitated for 1 hour at room temperature. After addition of MeOH to react the excess chloroamidite, this was purified by intermediate pressure chromatography (2% by volume Et$_3$N-containing dichloromethane-ethanol, volume ratio changed gradually from 1:0 to 9:1) to obtain 0.148 g of the target product, XII$_{Leu}$base=A (yield 63%).

$^1$H-NMR (300 MHz, DMSO-d6) δ: 0.81 (6H, d, J=6.4 Hz), 1.11 (12H, m), 1.35 (2H, m), 1.44 (1H, m), 2.06 (1H, m), 2.06 (2H, t, J=6.6 Hz), 2.27 (1H, m), 2.40 (1H, m), 2.74 (3H, m), 2.91 (2H, m), 3.28 (3H, m), 3.55 (2H, m), 3.70 (2H, m), 4.03 (2H, m), 4.1-4.4 (5H, m), 4.49 (1H, m), 5.27 (1H, m), 6.10 (1H, m), 6.52 (1H, m), 6.79 (4H×1/2, d, J=8.2 Hz), 6.81 (4H×1/2, d, J=8.2 Hz), 7.20 (7H, m), 7.33 (2H, d, J=6.8 Hz), 7.54 (2H, dd, J=7.1, 7.5 Hz), 7.64 (1H, dd, J=7.5, 7.5 Hz), 7.92 (1H×1/2, s), 7.94 (1H×1/2, s), 8.03 (2H, d, J=7.1 Hz), 8.26 (1H, br), 8.56 (1H×1/2, s), 8.56 (1H×1/2, s), 11.20 (1H, br), 11.67 (1H, br)

$^{31}$P-NMR (120 MHz, BCM, DMSO) δ: −2.01, −1.94, 148.69, 148.79

MALDI-TOF MS: Calculated value (C$_{68}$H$_{79}$N$_{11}$NaO$_{15}$P$_2^+$)=1374.5125 [M+Na]$^+$, measured value=1374.329 [M+Na]+

Example 41

Monomer: Synthesis of Substance II$_{Phe}$, Formula 66

(66)

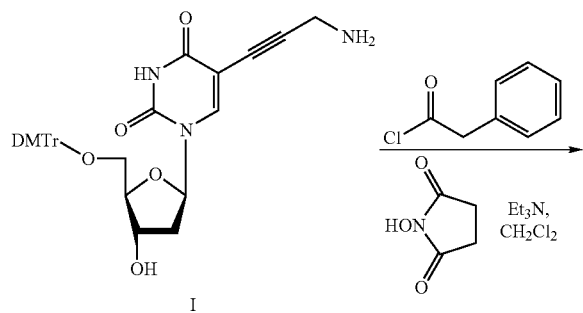

II$_{Phe}$ 1.21 mL of phenylacetylchloride was added to a 50 mL dry methylene chloride solution of 1.27 g (11 mol) N-hydroxysuccinic acid imide and 1.68 mL triethylamine (12 mmol), and agitated for 15 minutes at room temperature. The reaction solution with the insoluble matter filtered out was added at 0° C. to a dichloromethane solution (50 mL) of 7.10 g of Substance I (10 mmol equivalent). The mixed solution was agitated for 3 hours at room temperature, and for a further 30 minutes after addition of 1 mL pyridine. The reaction solution was washed with water, and the water layer was extracted twice with methylene chloride. The combined methylene chloride layer was dried with anhydrous sodium sulfate and concentrated. The concentrated residue was purified by intermediate pressure chromatography (dichloromethane-ethanol, volume ratio changed gradually from 1:0 to 93:7) to obtain 6.47 g of the target product, II$_{Phe}$ (yield 92%).

$^1$H-NMR (300 MHz, DMSO-d6) δ: 2.18 (1H, m), 2.25 (1H, m), 3.07 (1H, br·d, J=7.3 Hz), 3.25 (1H, m), 3.41 (2H, s), 3.72 (6H, s), 3.90 (2H, d, J=5.0 Hz), 4.26 (1H, m), 6.09 (1H, dd, J=6.4, 6.8 Hz), 6.88 (4H, d, J=6.8 Hz), 6.15-6.35 (7H, m), 7.38 (2H, br·d, J=7.5 Hz), 7.89 (1H, s), 8.45 (1H, br)

MALDI-TOF MS: Calculated value (C$_{41}$H$_{40}$N$_3$O$_8^+$)= 702.281 [M+H], measured value=701.901

Example 42

Monomer Amidite: Synthesis of Substance III$_{Phe}$, Formula 67

(67)

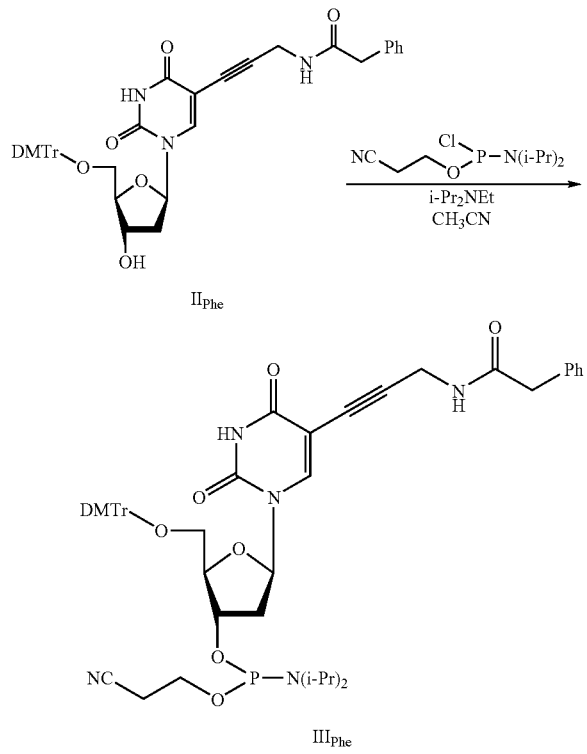

Substance II$_{Phe}$ (351 mg, 0.50 mmol) was azeotropically dehydrated three times in 5 mL of dry acetonitrile, and dried. This was dissolved in 10 mL of dry acetonitrile, and after addition of 104 μL diisopropylethylamine (0.60 mmol), diisopropylchlorophosphoramidite (122 μL, 0.55 mmol) was added under ice cooling. After 2 hours of agitation, methanol was added to inactivate the excess amidite-forming reagent, and the mixture was diluted with methylene chloride, and washed with a saturated aqueous sodium bicarbonate solution and a saturated aqueous sodium chloride solution. Purification by intermediate pressure chromatography (2% by volume Et$_3$N-containing dichloromethane:hexane, volume ratio gradually changed from 1:1 to 1:0, followed by 2% by volume Et$_3$N-containing dichloromethane:ethanol, volume ratio gradually changed from 1:0 to 19:1) yielded 393 mg of Substance III$_{Phe}$ (yield 87%).

$^1$H-NMR (300 MHz, DMSO-d6) δ: 0.98 (3H, d, J=6.8 Hz), 1.10 (3H, d, J=6.8 Hz), 1.10 (3H, d, J=6.8 Hz), 1.12 (3H, d, J=6.8 Hz), 2.30 (1H, m, C(2')H), 2.40 (1H, m, C(2')H), 2.64 (2H×1/2, t, J=5.9 Hz), 2.75 (2H×1/2, t, J=5.9 Hz), 3.14 (1H, m), 3.30 (1H, m), 3.41 (2H, s), 3.51 (2H, m), 3.62 (2H, m), 3.72 (6H, s), 3.91 (2H×1/2, d, J=5.3 Hz), 3.94 (2H×1/2, d, J=5.3 Hz), 4.01 (1/2H, m), 4.07 (1/2H, m), 4.48 (1H, m), 6.07 (1H, m), 6.85 (2H, d, J=8.5 Hz), 7.15-7.35 (7H, m), 7.38 (2H, br·d, J=5.9 Hz), 7.93 (1/2H, s), 7.94 (1/2H), 7.94 (1/2H, s), 8.45 (1/2H, t, J=5.3 Hz), 8.47 (1/2H, t, J=5.3 Hz)

$^{31}$P-NMR (120 MHz) δ: 147.77, 148.17

MALDI-TOF MS: Calculated value (C$_{50}$H$_{57}$N$_5$O$_9$P$^+$)=902.3888, measured value=901.994

Example 43

Levuloyl Group Introduction and DMTr Removal: Synthesis of Substance IX$_{Phe}$, Formula 68

(68)

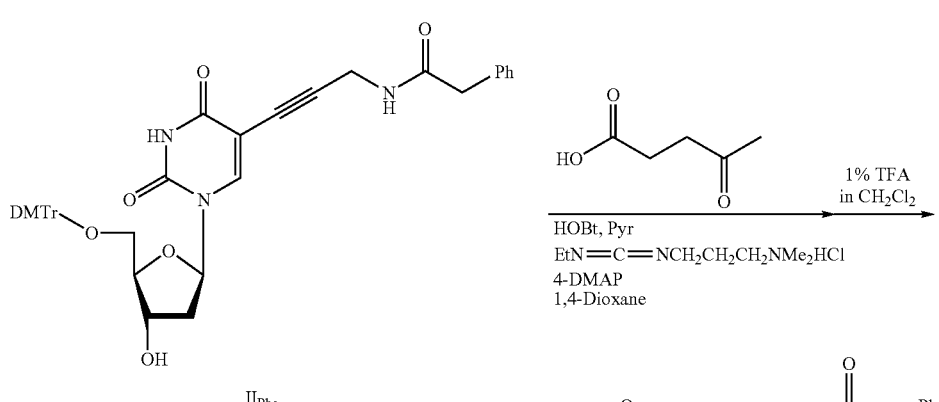

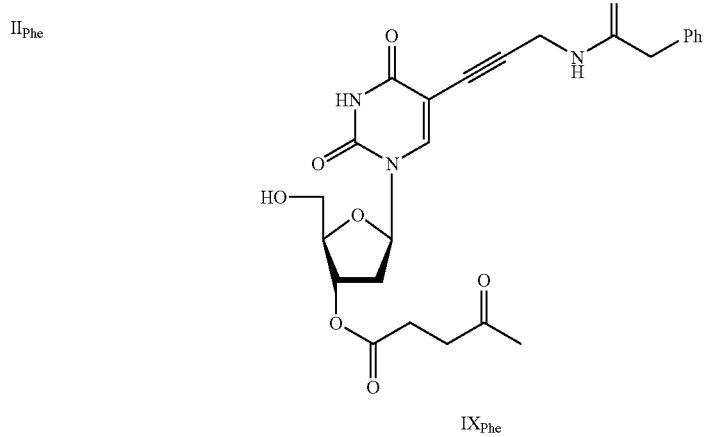

4.20 g of Substance II$_{Phe}$ (6.0 mmol) was dissolved in 30 mL of dry dioxane, and 58 mg (0.48 mmol) DIMAP, 2.48 g (12 mmol) DCC and 1.22 mL (12 mmol) levulinic acid were added and agitated for 30 minutes at room temperature. 3 mL of methanol was then added and agitated for 15 minutes. The insoluble matter was filtered out and the filtrate was concentrated and dried. The residue was dissolved in 42 mL of dry methylene chloride and ice cooled, and 0.88 mL of trifluoroacetic acid was added and agitated for 30 minutes at 0° C. This reaction solution was directly loaded onto silica gel and purified by intermediate pressure chromatography (dichloromethane-ethanol, volume ratio changed gradually from 19:1 to 9:1) to obtain 2.67 g of the target product, IX$_{Phe}$ (yield 88%).

$^1$H-NMR (300 MHz, DMSO-d6) δ: 2.10 (3H, s, Lev), 2.27 (2H, m), 2.49 (2H, m), 2.73 (2H, t, J=6.2 Hz), 3.43 (2H, s), 3.62 (2H, br), 3.99 (1H, m), 4.08 (2H, d, J=5.3 Hz), 5.19 (1H, m), 5.24 (1H, t, J=4.9 Hz), 6.12 (1H, dd, J=6.6, 7.3 Hz), 7.15-7.35 (5H, m, Ph), 8.16 (1H, s), 8.56 (1H, t, J=5.3 Hz)

Example 44

Dimer Synthesis: Synthesis of Substance

X$_{Phe}$base=C, Formula 69

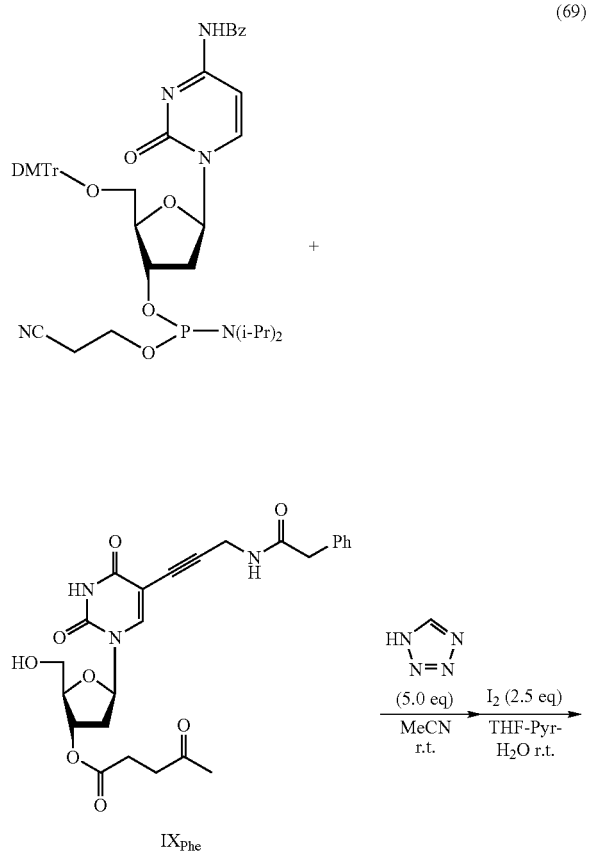

(69)

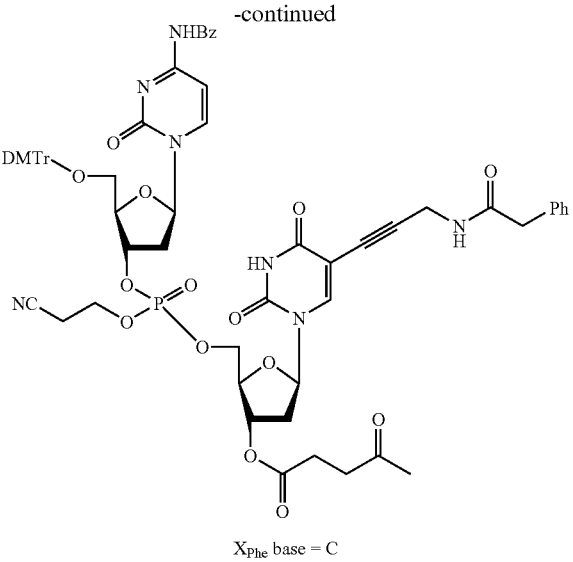

X$_{Phe}$ base = C 1.28 g (2.58 mmol) of Substance IX$_{Phe}$ was dissolved in dry acetonitrile, and the operation of removing the moisture content by distilling off the acetonitrile under reduced pressure was performed three times. The residue was dissolved in 13 mL of a dry acetonitrile solution of 2.48 g (2.97 mmol) of 5'-(4,4'-dimethoxytriphenylmethyl)-cytidine-3'-(diisopropylamino)cyanoethylphosphoramidite. 0.91 g (12.9 mmol) of tetrazole was added to the solution, which was then agitated for 1 hour at room temperature. Next, 1 mL of methanol was added and agitated for 15 minutes. The reaction solution was diluted in 60 mL of methylene chloride and washed with water, and the water layer was further extracted twice with methylene chloride. The combined methylene chloride layer was dried with anhydrous sodium sulfate, and concentrated. The concentrated residue was dissolved in a mixed solution of 50 mL THF, 14 mL pyridine and 7 mL water, and agitated for 30 minutes at room temperature after addition of 2.26 g (8.92 mmol) iodine. After dilution with methylene chloride, 5.6 g of sodium sulfite was added and agitated for 15 minutes at room temperature. After removal of the water content using anhydrous sodium sulfate, this was concentrated. The concentrated residue was diluted in methylene chloride and washed with water. The water layer was extracted twice with methylene chloride, and the combined methylene chloride layer was washed with a saturated aqueous sodium chloride solution, dried with anhydrous sodium sulfate, and concentrated.

The concentrated residue was purified by intermediate pressure chromatography (dichloromethane-ethanol, volume ratio changed gradually from 1:0 to 93:7) to obtain 3.19 g of the target product, X$_{Phe}$base=C (yield 99%).

$^1$H-NMR (300 MHz, DMSO-d6) δ: 2.08 (3H, s), 2.26 (1H, m), 2.45 (4H, m), 2.71 (3H, m), 2.86 (2H×1/2, t, J=5.9 Hz), 2.88 (2H×1/2, t, J=5.9 Hz), 3.32 (2H, m), 3.42 (2H, s), 3.72 (6H, s), 4.00-4.35 (8H, m), 5.03 (1H, m), 5.15 (1H, m), 6.09 (1H, m), 6.16 (1H, dd, J=5.5, 6.6 Hz), 6.87 (4H, d, J=8.6 Hz), 7.15-7.40 (14H, m), 7.50 (2H, dd, J=7.7, 7.9 Hz), 7.62 (1H, t, J=7.7 Hz), 7.94 (1H, s), 7.99 (2H, d, J=7.9 Hz), 8.13 (1H, br), 8.50 (1H, br), 11.21 (1H, br), 11.65 (1H, br)

$^{31}$P-NMR (120 MHz, DMSO-d6) δ: −2.41, −2.34

Example 45

Dimer Levuloyl Removal: Synthesis of Substance XI$_{Phe}$base=C, Formula 70

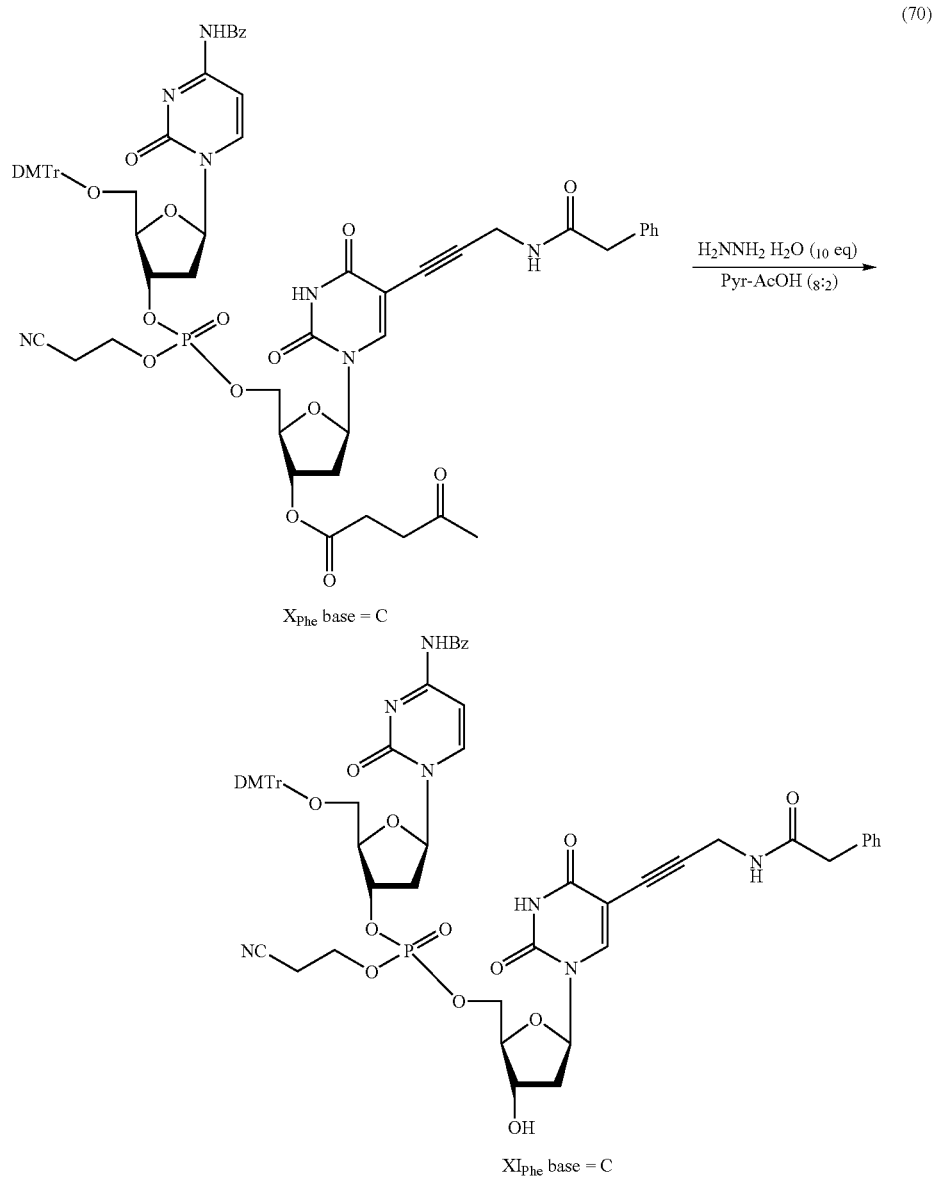

Substance X$_{Phe}$base=C (3.19 g, 2.56 mmol) was dissolved in 26 mL pyridine, and hydrazine monohydrate (1.03 mL, 18.7 mmol) and a mixed pyridine-acetic acid solvent (volume ratio 3:2, 34 mL) were added and agitated for 5 minutes at room temperature. 26 mL of acetone was added under ice cooling. The reaction liquid was diluted with methylene chloride and partitioned, and the water layer was further extracted twice with methylene chloride. The combined methylene chloride layer was washed with a saturated aqueous sodium chloride solution, dried with anhydrous sodium sulfate, and concentrated.

The concentrated residue was purified by intermediate pressure chromatography (dichloromethane-ethanol, volume ratio changed gradually from 1:0 to 93:7) to obtain 2.39 g of the target product, XI$_{Phe}$base=C (yield 82%).

$^1$H-NMR (300 MHz, DMSO-d6) δ: 2.12 (1H, m), 2.21 (1H, m), 2.47 (1H, m), 2.72 (1H, m), 2.86 (2H×1/2, t, J=5.9 Hz), 2.88 (2H×1/2, t, J=5.9 Hz), 3.33 (2H, m), 3.41 (2H, s), 3.72 (6H, s), 3.91 (1H, m), 4.0-4.40 (8H, m), 5.03 (1H, m), 5.43 (1H, d, J=4.2 Hz), 6.09 (1H, m), 6.19 (1H, dd, J=6.2, 6.6 Hz), 6.88 (4H, d, J=8.8 Hz), 7.15-7.40 (14H, m), 7.50 (2H, dd, J=7.3, 7.5 Hz), 7.62 (1H, t, J=7.5 Hz), 7.87 (1/2H, s), 7.88 (1/2H, s), 8.00 (1H, d, J=7.3 Hz), 8.10 (1H, br), 8.50 (1H, br), 11.23 (1H, br), 11.62 (1H, brw)

$^{31}$P-NMR (120 MHz, DMSO-d6) δ: −2.04, −1.94

MALDI-TOF MS: Calculated value (C$_{60}$H$_{58}$N$_7$NaO$_{15}$P)= 1170.3626 [M+Na]$^+$, measured value=1170.559

Example 46

Dimer Amidite: Synthesis of Substance XII$_{Phe}$base=T, Formula 71

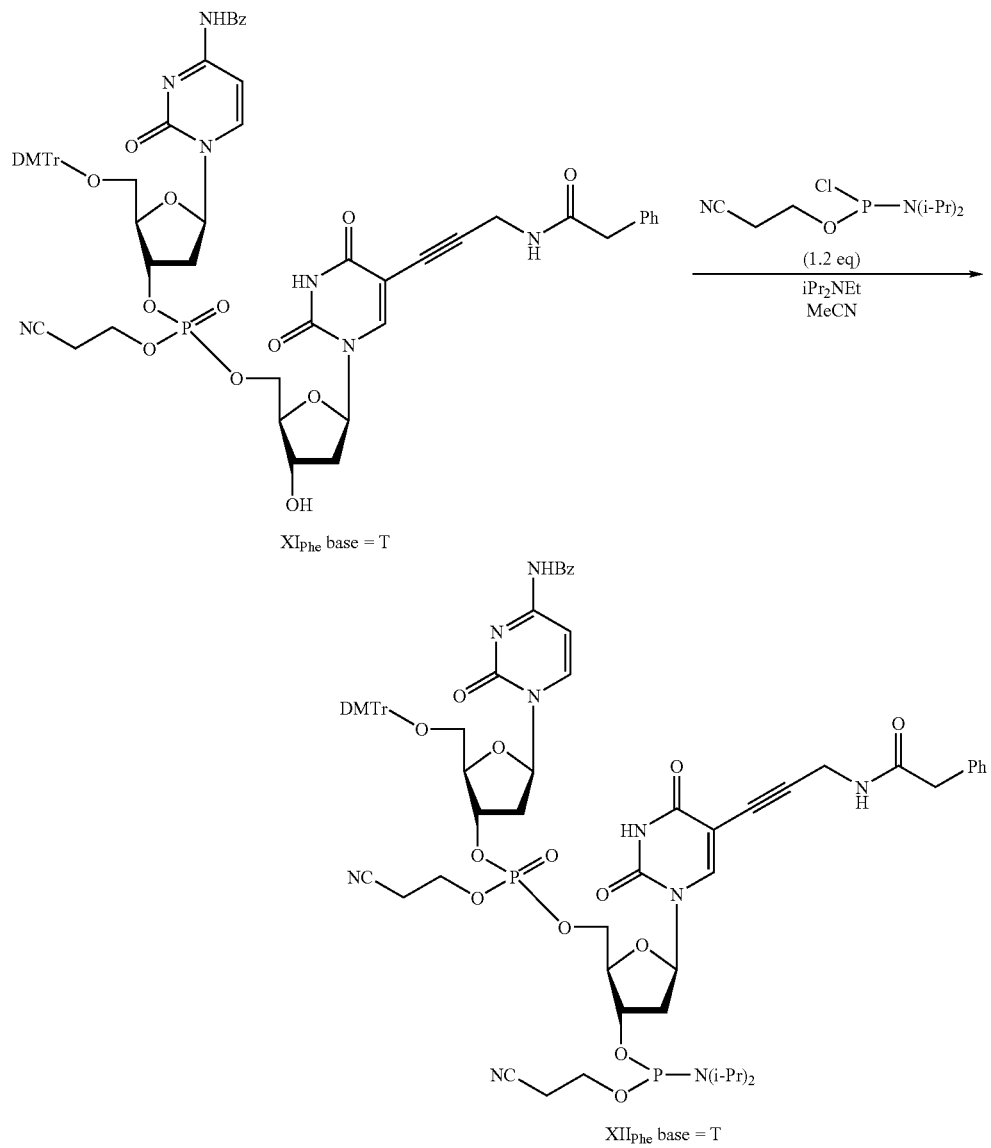

Substance XI$_{Phe}$base=T (0.493 g, 0.430 mmol) was azeotropically dehydrated three times with dry acetonitrile and dissolved in 4.3 mL of mixed dry acetonitrile-methylene chloride (1:1) solvent, and diisopropylethylamine (96 μL, 0.558 mmol) was added. Cyanoethylchlorodiisopropyl phosphoramidite (115 μL, 0.516 mmol) was added thereto and agitated for 1 hour at room temperature. After addition of MeOH to react the excess chloroamidite, this was partitioned between methylene chloride and water, and the organic layer was dried with anhydrous sodium sulfate, and concentrated.

The residue was separated and purified by intermediate pressure chromatography (2% by volume Et$_3$N-containing dichloromethane:ethanol, volume ratio changed gradually from 1:0 to 9:1) to obtain 0.363 of the target product, XII$_{Phe}$base=T (yield 63%).

$^1$H-NMR (300 MHz, DMSO-d6) δ: 1.12 (12H, d, J=6.6 Hz), 2.26 (1H, m), 2.42 (2H, m), 2.75 (3H, m), 2.87 (2H, m), 3.33 (2H, m), 3.42 (2H, s), 3.54 (2H, m), 3.71 (6H, s), 3.71 (2H, m), 4.06 (2H, br), 4.1-4.3 (6H, m), 4.47 (1H, m), 5.03 (1H, m), 6.09 (1H, m), 6.16 (1H, m), 6.88 (4H, d, J=8.6 Hz), 7.2-7.4 (14H, m), 7.50 (2H, dd, J=7.5, 7.6 Hz), 7.62 (1H, t, J=7.6 Hz), 7.93 (1H, m), 7.99 (2H, d, J=7.5 Hz), 8.15 (1H, br), 8.55 (1H, br), 11.28 (1H, m, br), 11.67 (1H, m, br)

$^{31}$P-NMR (BCM, 120 MHz, DMSO-d6) δ: −2.01, 148.55, 148.67

MALDI-TOF MS: Calculated value (C$_{69}$H$_{75}$N$_9$NaO$_{16}$P$_2^+$)=1370.470, measured value=1370.559

Example 47

Preparation of Random DNA Mix

TABLE 1

| Table 1 | | A | G | C | T | X |
|---|---|---|---|---|---|---|
| | | | | 3' | | |
| 5' | A | — | — | — | — | Leu |
| | G | — | — | — | — | Glu |
| | C | — | — | — | — | Phe |
| | T | — | — | — | — | Ser |
| | X | Lys | Tyr | Trp | — | — |

TABLE 2

| Table 2 | | A | G | C | T | Y |
|---|---|---|---|---|---|---|
| | | | | 3' | | |
| 5' | A | — | — | — | — | Leu |
| | G | — | — | — | — | Glu |
| | C | — | — | — | — | Phe |
| | T | — | — | — | — | Ser |
| | Y | Lys | Tyr | Trp | — | — | ttatcaacaaaatactccaattg(NpNp)$_{25}$gaaagatcccaacgaaaag was synthesized with an automated DNA synthesizer (Applied 391A). The NpNp part was synthesized using the mixed amidites of the dimer amidite table, Table 1 or 2.

Figure 6:
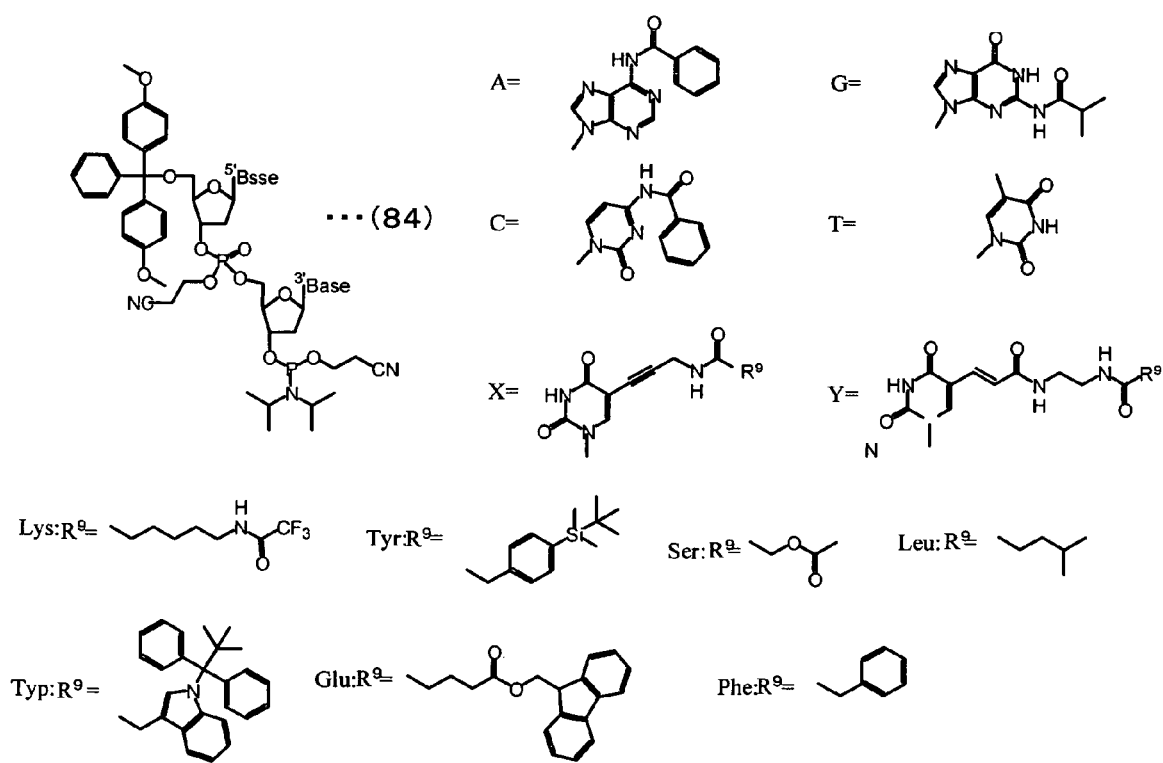
FIG. 6 explains the symbols in Tables 1 and 2.
Figure 7:
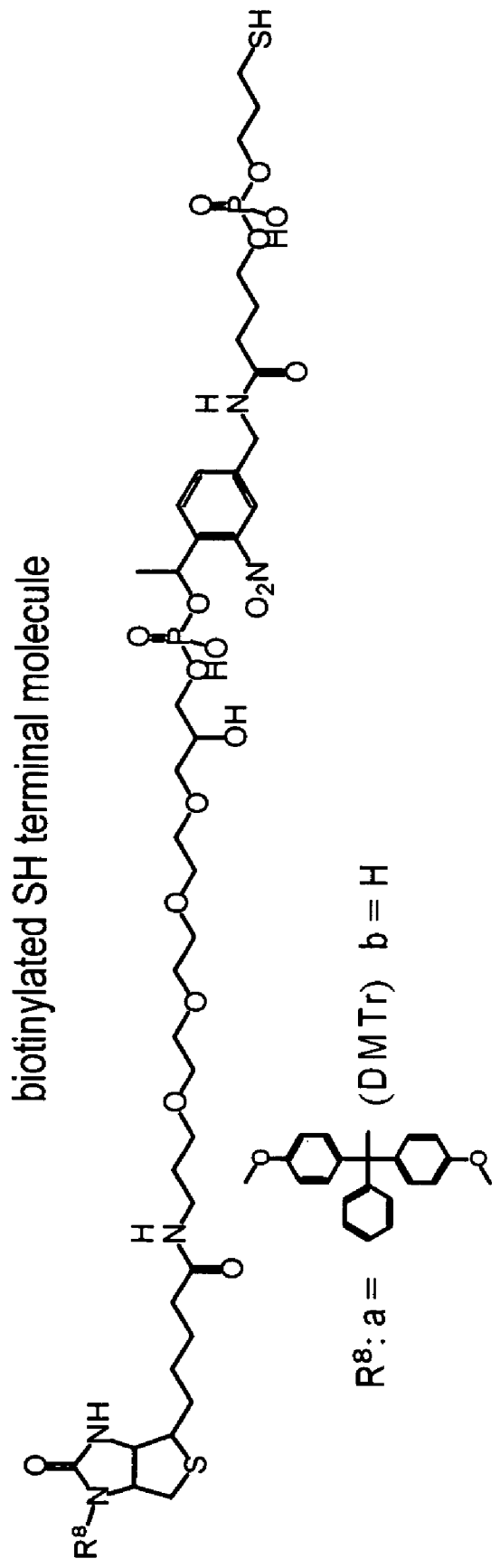
FIG. 7 shows the structures of the biotinylated SH terminal molecule and $R^8$.

The symbols in the Tables are explained in FIG. 6. The structure of the dimer amidite obtained with the combination in the tables is shown in Formula 84 in FIG. 6. A, G, C, T, X and Y indicate groups modifying the base of the dinucleotide represented by Formula 84 in FIG. 6. 3' and 5' in the tables signify that A, G, C, T, X or Y is bound as the base indicated by 3' Base or 5' Base in Formula 84. Lys, Tyr, Trp, Leu, Glu or Ser signifies that $R^9$ in X or Y is Lys, Tyr, Trp, Leu, Glu or Ser. For example, a dinucleotide obtained from a combination of the A of 3' and the X of 5' in the tables is one in which A is bound as the 3' Base and X as the 5' Base of the structure shown in Formula 84, with the $R^9$ of X being Lys.

For the synthesized random DNA mix, the FMOC group of the amidite was deprotected on a solid-phase support using DBU on a solid-phase resin, the amidite DNA was cleaved using ammonia according to established methods, and the remaining protective groups were deprotected. The ammonia was removed by evaporation, and a GL Sciences SNPsi was used to synthesize an affinity resin from pCAATTGGAG-TATTTTGTTGATAA, TTATCAACAAAATACTCCAAT-TGAACCACTGCTT using DNA ligase. Using this resin, double strands complementary to the synthesized DNA random mix X (from Table 1) or Y (from Table 2) were formed and purified by serially raising the temperature of the resin. The concentration was determined using a UV absorbtiometer.

(Avidin Affinity Purification of Aptamers from Random Mixes)

A biotin-modified resin (cysteine capped) was prepared using a Pierce MicroLink Peptide Coupling Kit on a resin according to the attached protocols. The structure a in FIG. 7 was used as the $R^8$ of the biotinylated SH terminal molecule in FIG. 7, followed by a TFA treatment. After the amount of modification had been identified by DMTr$^+$ coloration the b of FIG. 7 was applied to the $R^8$ of the biotinylated SH terminal molecule to prepare a biotin-modified resin.

Using this resin (25% by weight slurry, 400 µL), 200 µL of 10 mg/mL streptavidin was reacted for 2 hours at room temperature under shaded conditions to prepare a streptavidin-biotin modified resin.

This resin was washed 10 times or more at 50° C. with 1 mL of (0.5 M NaCl, 0.05% Tween-20, 10 mM Tris-HCl, pH 8.5).

Next, 200 µL (50 nmol) of the aforementioned random mix X or Y was reacted overnight at room temperature under shaded conditions to prepare a modified nucleic acid-streptavidin-biotin modified resin and washed 10 times or more at 50° C. in 1 mL of (50 mM NaCl, 1 mM MgCl$_2$, 0.05% Tween-20, 10 mM Tris-HCl, pH=8.5), and the absence of the modified nucleic acid in the wash liquid was confirmed by quantitative PCR.

Next the resin was wetted with (50 mM KCl, 1 mM MgCl$_2$, 10 mM Tris-HCl, pH 8.5), exposed to light at 366 nm for 10 minutes, and washed with 100 µL of (50 mM KCl, 1 mM MgCl$_2$, 10 mM Tris-HCl, pH=8.5).

Using these solutions X and Y PCR was performed to amplify the DNA using TTATCAACAAAATACTC-CAATTG and CTTTTCGTTGGGATCTTTC as the primers. The product was cloned according to established methods, and the sequences of 100 clones determined.

After decoding by the block code method, modified nucleic acids were synthesized using a DNA synthesizer, and the binding-dissociation constant of each with streptavidin was determined.

As a result, it was confirmed that 20 sequences from X had a Kd of $10^{-7}$ or less while 3 sequences from Y had a Kd of $10^{-7}$ or less, indicating that the triple bond linker used in X is more useful than the double bond linker used in Y.

---

What is claimed is:

1. A modified nucleotide n-mer where n=1 with a structure represented by Formula 18 below, comprising a nucleoside unit with a substituent group introduced into the base, wherein said substituent group is bound to said base via a triple bond

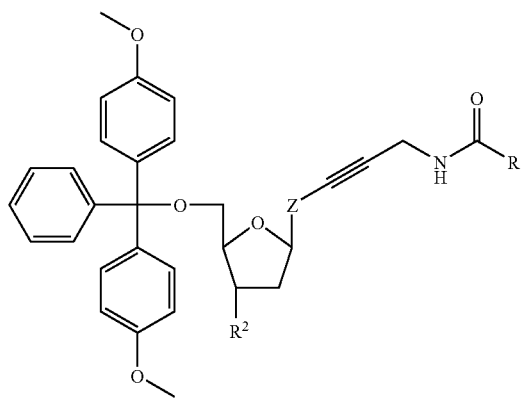
(18)

where Z represents a group comprising a 7-deazaadenine skeleton, 7-deazaguanine skeleton, cytosine skeleton or uracil skeleton independently of the other formulae, and R represents hydrogen or a functional group having 0 to 100 carbon atoms independently of the other formulae, and $R^2$ represents a hydroxy group, O-β-cyanoethoxy-diisopropylaminophosphine group, O-methoxy-diisopropylaminophosphine group or H-phosphonate group independently of the other formulae, wherein the substituent group is a group selected from the groups represented by Formulae 13-17

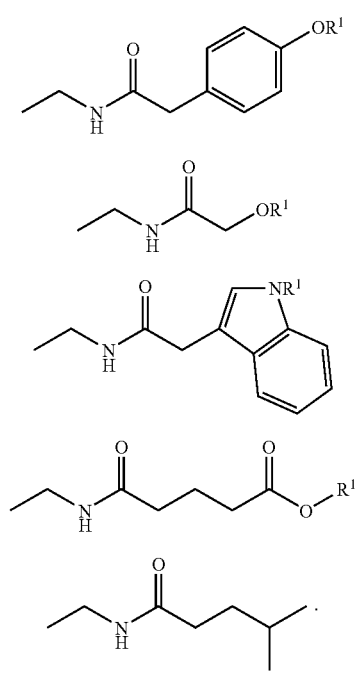

2. A modified nucleotide m-mer where m represents an integer of 2 or more comprising the modified nucleotide n-mer according to claim 1 as a constituent element.

3. A modified nucleotide n-mer where n represents an integer of 2 or more comprising a nucleoside unit having a substituent group introduced into the base, wherein said substituent group is bound to said base via a triple bond, wherein the substituent group is a group selected from the groups represented by Formulae 12-17

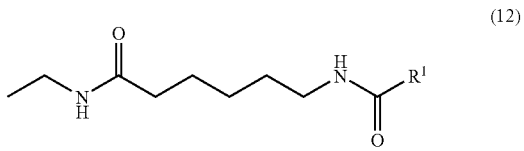
(12)

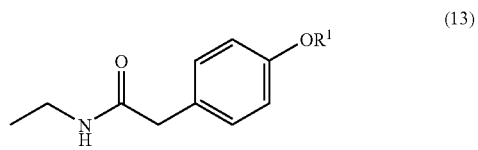
(13)

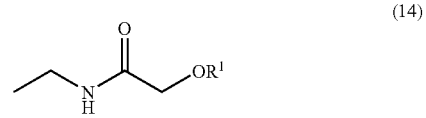
(14)

(15)

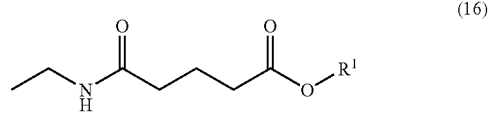
(16)

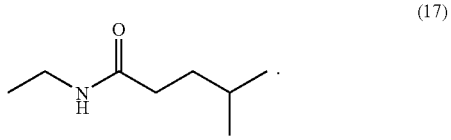
(17)

4. The modified nucleotide n-mer according to claim 3, wherein said base has a 7-deazaadenine skeleton, 7-deazaguanine skeleton, cytosine skeleton or uracil skeleton.

5. The modified nucleotide n-mer according to claim 3, wherein n is an integer from 2 to 4.

6. A modified nucleotide sequence comprising the structure of a modified nucleotide m-mer according to claim 2.

7. A modified nucleotide sequence comprising the structure of a modified nucleotide n-mer according to claim 3.

8. A modified nucleotide sequence comprising the structure of a modified nucleotide n-mer according to claim 4.

* * * * *

SEQUENCE LISTING

```
<160> NUMBER OF SEQ ID NOS: 5

<210> SEQ ID NO 1
<211> LENGTH: 92
<212> TYPE: DNA
<213> ORGANISM: artificial sequence
<220> FEATURE:
<223> OTHER INFORMATION: Random mix sequence for selection
<220> FEATURE:
<221> NAME/KEY: modified_base
<222> LOCATION: (24)..(73)
<220> FEATURE:
<221> NAME/KEY: misc_feature
```

-continued

```
<222> LOCATION: (24)..(73)
<223> OTHER INFORMATION: n is a, c, g, or t

<400> SEQUENCE: 1
ttatcaacaa aatactccaa ttgnnnnnnn nnnnnnnnnn nnnnnnnnnn nnnnnnnnnn      60
nnnnnnnnnn nnngaaagat cccaacgaaa ag                                   92

<210> SEQ ID NO 2
<211> LENGTH: 23
<212> TYPE: DNA
<213> ORGANISM: artificial sequence
<220> FEATURE:
<223> OTHER INFORMATION: Complementary sequence for ligation
<220> FEATURE:
<221> NAME/KEY: misc_difference
<222> LOCATION: (1)..(1)
<220> FEATURE:
<221> NAME/KEY: misc_feature
<222> LOCATION: (1)..(1)
<223> OTHER INFORMATION: n is a, c, g, or t

<400> SEQUENCE: 2
naattggagt attttgttga taa                                             23

<210> SEQ ID NO 3
<211> LENGTH: 34
<212> TYPE: DNA
<213> ORGANISM: artificial sequence
<220> FEATURE:
<223> OTHER INFORMATION: primer

<400> SEQUENCE: 3
ttatcaacaa aatactccaa ttgaaccact gctt                                 34

<210> SEQ ID NO 4
<211> LENGTH: 23
<212> TYPE: DNA
<213> ORGANISM: artificial sequence
<220> FEATURE:
<223> OTHER INFORMATION: primer

<400> SEQUENCE: 4
ttatcaacaa aatactccaa ttg                                             23

<210> SEQ ID NO 5
<211> LENGTH: 19
<212> TYPE: DNA
<213> ORGANISM: artificial sequence
<220> FEATURE:
<223> OTHER INFORMATION: primer

<400> SEQUENCE: 5
cttttcgttg ggatctttc                                                  19
```